(12) United States Patent (10) Patent No.: US 9,549,988 B2
McCraith (45) Date of Patent: Jan. 24, 2017

(54) PHARMACEUTICAL COMPOUNDS TARGETED BY MIF AFFINITY-TETHERED MOIETIES

(71) Applicant: RJS Biologics LLC, Seattle, WA (US)

(72) Inventor: Stephen McCraith, Seattle, WA (US)

(73) Assignee: RJS Biologics, Seattle, WA (US)

( * ) Notice: Subject to any disclaimer, the term of this patent is extended or adjusted under 35 U.S.C. 154(b) by 150 days.

(21) Appl. No.: 14/298,952

(22) Filed: Jun. 8, 2014

(65) Prior Publication Data

US 2015/0352217 A1 Dec. 10, 2015

Related U.S. Application Data

(60) Provisional application No. 61/832,879, filed on Jun. 9, 2013.

(51) Int. Cl.
*A61K 31/704* (2006.01)
*A61K 31/366* (2006.01)
*A61K 47/48* (2006.01)
*A61K 49/10* (2006.01)
*A61K 39/395* (2006.01)
*A61K 31/54* (2006.01)

(52) U.S. Cl.
CPC ....... *A61K 47/48061* (2013.01); *A61K 31/366* (2013.01); *A61K 31/54* (2013.01); *A61K 31/704* (2013.01); *A61K 39/3955* (2013.01); *A61K 49/106* (2013.01)

(58) Field of Classification Search
CPC .............................. A61K 31/704; A61K 31/366
See application file for complete search history.

(56) References Cited

U.S. PATENT DOCUMENTS

| 2003/0195194 A1 | 10/2003 | Gaeta et al. |
| 2007/0219189 A1 | 9/2007 | Billich et al. |
| 2008/0317744 A1 | 12/2008 | Boyce et al. |
| 2010/0190770 A1 | 7/2010 | Li et al. |
| 2010/0280030 A1 | 11/2010 | Schadt et al. |
| 2012/0016131 A1 | 1/2012 | Lei et al. |

FOREIGN PATENT DOCUMENTS

WO WO2010021693 2/2010

OTHER PUBLICATIONS

Lubetsky et al. (2002). "The tautomerase active site of macrophage migration inhibitory factor is a potential target for discovery of novel anti-inflammatory agents." J. Biol. Chem. 277(28): 24976-82.
Rosengren et al. (1997). "The macrophage migration inhibitory factor MIF is a phenylpyruvate tautomerase." FEBS Lett. 417(1): 85-8.
Rosengren et al. (1996). "The immunoregulatory mediator macrophage migration inhibitory factor (MIF) catalyzes a tautomerization reaction." Mol. Med. 2(1): 143-9.
El-Sabbagh "Synthesis of some new benzisothiazolone and benzenesulfonamide derivatives of biological interest starting from saccharin sodium." Arch. Pharm. (Weinheim) 346(10): 733-42, 2013.
Crichlow et al. (2009). "Structural and kinetic analyses of macrophage migration inhibitory factor active site interactions." Biochemistry 48(1): 132-9.
Mitchell et al., "Stromal-dependent tumor promotion by MIF family members." Cell Signal 26(12): 2969-2978.
Jorgensen (2004). "The many roles of computation in drug discovery." Science 303(5665): 1813-8.
Jorgensen1 et al. "Receptor agonists of macrophage migration inhibitory factor." Bioorg. Med. Chem. Lett. 20(23): 7033-6.
Lubetsky2 et al. (1999). "Pro-1 of macrophage migration inhibitory factor functions as a catalytic base in the phenylpyruvate tautomerase activity." Biochemistry 38(22): 7346-54.
Hare et al. "Optimization of N-benzyl-benzoxazol-2-ones as receptor antagonists of macrophage migration inhibitory factor (MIF)." Bioorg. Med. Chem. Lett. 20(19): 5811-4.
Leng et al. (2003). "MIF signal transduction initiated by binding to CD74." J Exp Med 197(11): 1467-76.
Stamps et al. (2000). "Mechanism of the phenylpyruvate tautomerase activity of macrophage migration inhibitory factor: properties of the P1G, P1A, Y95F, and N97A mutants." Biochemistry 39(32): 9671-8.
Dios, et al. (2002). "Inhibition of MIF bioactivity by rational design of pharmacological inhibitors of MIF tautomerase activity." J. Med. Chem. 45(12): 2410-6.
Senter et al. (2002). "Inhibition of macrophage migration inhibitory factor (MIF) tautomerase and biological activities by acetaminophen metabolites." Proc. Natl. Acad. Sci. U S A 99(1): 144-9.
Zhang (1999). "Inhibition of macrophage migration inhibitory factor (MIF) tautomerase activity by dopachrome analogs." Bioorg. Med. Chem. Lett. 9(22): 3193-8.
Courina et al. (2009). "Discovery of human macrophage migration inhibitory factor (MIF)-CD74 antagonists via virtual screening." J. Med. Chem. 52(2): 416-24.
Liu et al. "Design, synthesis and evaluation of 1,2-benzisothiazol-3-one derivatives as potent caspase-3 inhibitors." Bioorg. Med. Chem. 21(11): 2960-7.

(Continued)

*Primary Examiner* — Shawquia Jackson
(74) *Attorney, Agent, or Firm* — Jeffrey B. Oster

(57) ABSTRACT

There is disclosed a compound, a pharmaceutical composition and a method of treatment using a pharmaceutical composition comprising a tethering moiety that is capable of binding to a macrophage migration inhibitory factor (MIF) polypeptide, optionally linked to a linker moiety and further covalently bound to a drug moiety or imaging agent. More specifically, there is disclosed a genus of affinity-tethering moieties covalently bound to a drug moiety or imaging agent either directly or optionally via a linker moiety to covalently link the tethering moiety to a drug moiety. Without being bound by theory, the disclosed pharmaceutical compounds are targeted to cancer cells or immune cells via an affinity-tethering moiety that hitch-hikes to or into its target cell while bound to endogenous MIF.

15 Claims, 27 Drawing Sheets

(56) References Cited

OTHER PUBLICATIONS

Sun et al. (1996). "Crystal structure at 2.6-A resolution of human macrophage migration inhibitory factor." Proc. Natl. Acad. Sci. U S A 93(11): 5191-6.
Cheng et al. (2006). "Critical modifications of the ISO-1 scaffold improve its potent inhibition of macrophage migration inhibitory factor (MIF) tautomerase activity." Bioorg. Med. Chem. Lett. 16(13): 3376-9.
Orita et al. (2001). "Coumarin and chromen-4-one analogues as tautomerase inhibitors of macrophage migration inhibitory factor: discovery and X-ray crystallography." J. Med. Chem. 44(4): 540-7.
Jorgensen3 et al. "Benzisothiazolones as modulators of macrophage migration inhibitory factor." Bioorg. Med. Chem. Lett. 21(15): 4545-9.
Dagia, N. M., D. V. Kamath, et al. (2009). "A fluorinated analog of ISO-1 blocks the recognition and biological function of MIF and is orally efficacious in a murine model of colitis." Eur. J. Pharmacol. 607(1-3): 201-12.

Comparison of cellular uptake of Amine Tethered-Dox
(RJS004_5) vs Doxorubicin using flow cytometry Affinity-tethering Dox changes the intracellular localization of Doxorubicin in leukemia cell lines.

Affinity-tethering Dox changes the intracellular localization of Doxorubi
cancer cells.

5-Me-Benzoxazolone

6-OH-Benzoxazolone

5-F, 6-OH-Benzoxazolone

PHARMACEUTICAL COMPOUNDS TARGETED BY MIF AFFINITY-TETHERED MOIETIES

CROSS REFERENCE TO RELATED APPLICATION

This patent application claims priority from U.S. provisional patent application 61/832,879 filed on 9 Jun. 2013.

TECHNICAL FIELD

The present disclosure provides compounds, pharmaceutical compositions and methods of treatment using a pharmaceutical composition comprising a tethering moiety that binds to a macrophage migration inhibitory factor (MIF) polypeptide, optionally linked to a linker moiety and further covalently bound to a drug moiety. More specifically, the present disclosure provides a pharmaceutical composition and method of treatment comprising a genus of affinity-tethering moieties covalently bound to a drug moiety either directly or optionally via a linker moiety to covalently link the affinity-tethering moiety to a drug substance. Further still, the present disclosure provides a compound, pharmaceutical composition and method of treatment comprising a tethering moiety that competes with ISO-1 ((S,R)-3-(4-hydroxyphenyl)-4,5-dihydro-5-isoxazole acetic acid methyl ester) for binding to the tautomerase site of MIF. Further still, the present disclosure provides a, pharmaceutical composition and method of treatment comprising a teathering moiety that bind to the tautomerase site of MIF with a dissociation constant between 10 mM and 1 pM.

BACKGROUND

Macrophage migration inhibitory factor (MIF) is a pro-inflammatory cytokine that contains both thiol-protein oxidoreductase activity and tautomerase/isomerase activity. MIF is released by T-cells and macrophages and modulates not only macrophage functions, but also T cell functions (Kitaichi et al., *Immunobiology*, 2000. 201 (3-4): p. 356-67). MIF is viewed to play a role in a wide range of diseases including, cancer, rheumatoid arthritis, sepsis, atherosclerosis, colitis, lupus, asthma, acute respiratory distress syndrome and acute graft-versus-host disease. MIF is involved in cellular proliferation and differentiation and has been demonstrated to have protumorigenic activity. MIF expression in tumors is thought enhance the aggressiveness and metastatic potential of tumor cells. MIF is overexpressed in many tumors, including breast, ovarian, colon and prostate cancer, melanoma, cervical cancer, gastric cancers, hepatocellular carcinoma, and glioblastomas (Hagemann et al., 2007, *Mol. Cancer Ther.*, 6, 7, 1993-2002; Akbar et al., 2001, *Cancer Lett.*, 171, 2, 125-32, Kamimura et al., 2000, *Cancer*, 89, 2, 334-41; Xu et al., 2008, *Cancer Lett.*, 261, 2, 147-57; Munaut et al., 2002, *Neuropathol Appl. Neurobiol.*, 28, 6, 452-60; Bacher et al., 2003, *Am. J. Pathol.*, 162, 1, 11-7; and Meyer-Siegler et al., 2002, *Cancer*, 94, 5, 1449-56).

The over-expression of macrophage migration inhibitory factor (MIF), and/or MIF receptor/s (CD74 and CXCR4) is observed in premalignant, malignant, and metastatic tumors. This over-expression is observed in cancers including non-small cell lung cancers (Gamez-Pozo et al., *PLoS One*, 7, 3, e33752; and McClelland et al., 2009, *Am. J. Pathol.*, 174, 2, 638-46). Cancer cells over-expressing CD74 can import approximately ~$10^7$ molecules of an anti-CD74 mAb (LL1) per cell per day (Hansen et al., 1996, *Biochem. J.*, 320 (Pt 1), 293-300). The surface half-life of the CD74 may be less than ten minutes (Starlets et al., 2006, *Blood*, 107, 12, 4807-16).

Analyses of an MIF knockout mouse model and the use of anti-MIF antibodies to modulate MIF levels have demonstrated MIF involvement in cancer and inflammation. MIF may play a role in the progression to more invasive tumors and MIF may control the tumor spectrum mediating a shift in frequency between T-cell lymphomas, fibrosarcomas and B-cell lymphomas (Bernhagen et al *Nature Med.*, 2007. 13(5): p. 587-96 and Taylor et al. *BMC Cancer*, 2007. 7: p. 135.). De Jong and associates showed that Murine colitis is dependent on continuous MIF production by the immune system. Both ulcerative colitis (UC) and Crohn's colitis patients are at increased risk of developing colorectal cancer (De Jong et al. *Nature Immunol.*, 2001. 2(11): p. 1061-6 and Itzkowitz and Yio, *Am. J. Physiol Gastrointest. Liver Physiol.*, 2004. 287(1): p. G7-17) used mice knocked out both for MIF and a second gene causing T-cell deficiency. Colitis was shown to be dependent on MIF produced by non-lymphocyte hematopoetic cells.

MIF circulates normally in human plasma at high levels of 2-6 ng/ml (Stosic-Grujicic et al. *Autoimmun. Rev.*, 2009. 8(3): p. 244-9) and these levels can be increased in disease states including many cancers. In sepsis, levels of MIF may be elevated more than 100 fold over basal level (Emonts et al., *Clin. Infect. Dis.*, 2007. 44(10): p. 1321-8).

A major problem in most forms of cancer chemotherapy is the severe non-specific toxicity chemotherapeutic drugs may also have against rapidly-dividing cells and healthy tissues. These side effects often result in dose reduction, treatment delay or discontinuance of therapy. Targeted drug delivery systems have been developed to try to circumvent these side effects, using targeting agents such as receptor ligands, sugars, lectins, antibodies, antibody fragments, hormones, and hormone analogues. Therefore, there is a need in the art to better target cytotoxic moieties into those areas of cancer cells where the toxic moiety can better exert its pharmacologic influence.

SUMMARY

The present disclosure provides compounds, pharmaceutical compositions and methods of treatment using a pharmaceutical composition comprising a tethering moiety that is capable of binding to a macrophage migration inhibitory factor (MIF) polypeptide, optionally linked to a linker moiety and further covalently bound to a drug or imaging moiety. Preferably, the tethering moiety comprises a moiety from formula (1)

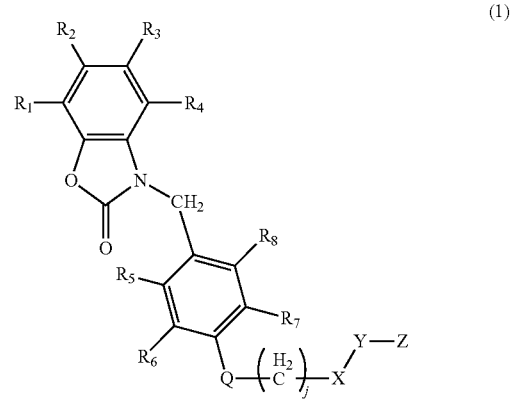

(1)

wherein Q is selected from the group consisting of O, S, N(R9), and C(R9)R10;

X is selected from the group consisting of nothing, O, S, N(R9), N(R9)N(R10), (CH$_2$)k-(OCH2CH$_2$)l, CR9R10-CR11R12, and C(O);

Y is selected from the group consisting of nothing, O, S, N(R11), N(R11)N(R12), —N=, C(O), C(O)O—, C(O)N (R9)-, C(O)N(R9)N(R10)-, C(O)N(R9)N=, C(O)(CH$_2$)m-S—, and C(O)(CH$_2$)m-S—S—;

R1, R2, R3, R4, R5, R6, R7 and R8 are each independently selected from the group consisting of H, hydroxyl, C1-C8 alkyl, alkenyl, alkynyl, substituted C1-C8 alkyl, alkenyl, alkynyl, C1-C8 acyl, substituted C1-C8 acyl, C1-C8 alkoxy, substituted C1-C8 alkoxy, C1-C8 ester, substituted C1-C8 ester, $(CH_2)n$-phenyl, substituted $(CH_2)n$-phenyl, $(CH_2)n$-heterocycle, substituted $(CH_2)n$-heterocycle, halogen, cyano, nitro, amino, $(CH_2)n$-monoalkylamine, substituted $(CH_2)n$-monoalkylamine, $(CH_2)n$-dialkylamine, substituted $(CH_2)n$-dialkylamine, carboxylic acid, $(CH_2)n$-dialkylamine, $(CH_2)n$-monoalkylamide, substituted $(CH_2)n$-monoalkylamide, $(CH_2)n$-dialkylamide, and substituted $(CH_2)n$-dialkylamide; wherein the substitutions are selected from the group consisting of C1-8 alkyl, C1-8 alkenyl, halo-substituted aryl, aryl, hydroxyl, hydrogen, C1-8 alkoxy, and combinations thereof.

R9, R10, R11, and R12 are each independently selected from the group consisting of H, hydroxyl, C1-C8 alkyl, substituted C1-C8 alkyl, alkenyl, alkynyl, $(CH_2)_n$-phenyl, substituted $(CH_2)n$-phenyl, $(CH_2)n$-heterocycle, and substituted $(CH_2)_n$-heterocycle; wherein the substitutions are selected from the group consisting of C1-8 alkyl, C1-8 alkenyl, halo-substituted aryl, aryl, hydroxyl, hydrogen, C1-8 alkoxy, and combinations thereof.

j, m, and n are each integers independently from 0 to 8, k is an integer from 0 to 2, l is an integer from 1 to 8; and Z represents the drug or imaging moiety.

Preferably the tether moiety is selected from the group consisting of:

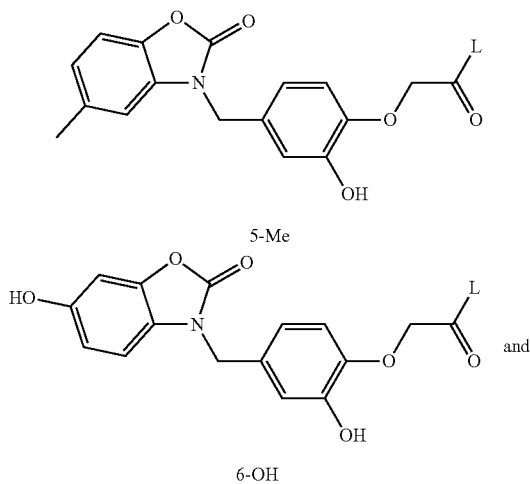

5-Me

6-OH and

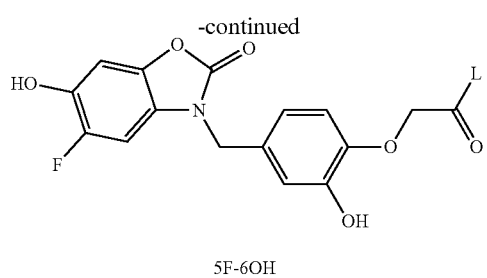

5F-6OH wherein L is an optional linker or spacer unit. More preferably, L comprises a linear or branched chain comprising a plurality of linking groups Lm, wherein m is an integer from 0 to about 50.

Preferably, Q is O; j is 1; X is C(O); Y is nothing; R1, R4, R5, R7, and R8 are hydrogen; R3 is methyl; R6 is hydroxyl and Z is Doxorubicin. Preferably, the compound N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[d]oxazol-3(2H)-yl)methyl)phenoxy)acetamide is:

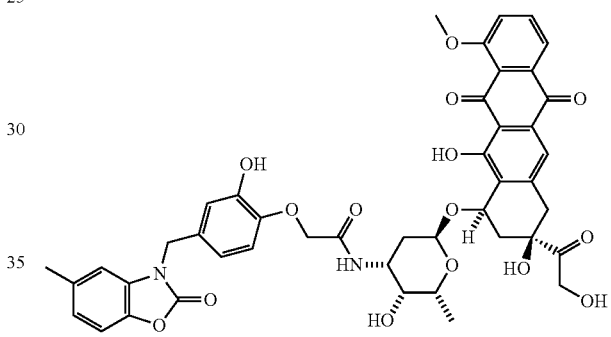

Preferably, Q is O; j is 1; X is nothing; Y is C(O)N(R9)N=; R1, R2, R4, R5, R7, R8, and R9 are hydrogen; R3 is methyl; R6 is hydroxyl; and Z is Doxorubicin. Preferably, the compound is N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide:

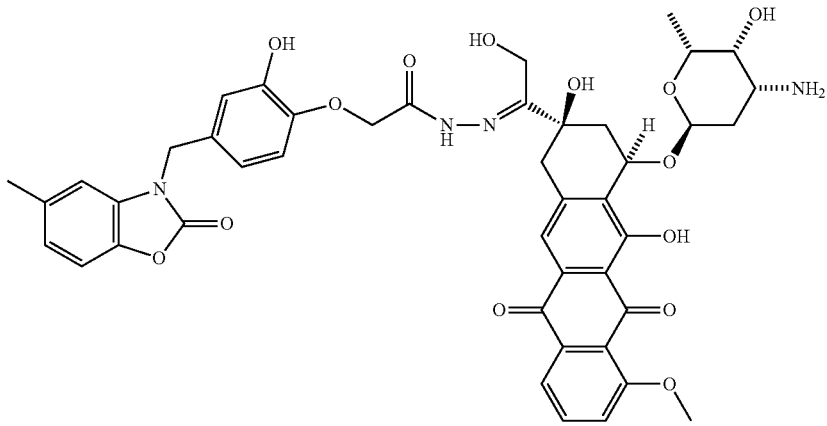

Preferably, Q is O; j is 1; X is C(O); Y is nothing; R1, R2, R4, R5, R7, and R8 are hydrogen; R3 is methyl; R6 is hydroxyl and Z is artemisinin. Preferably, the compound is:

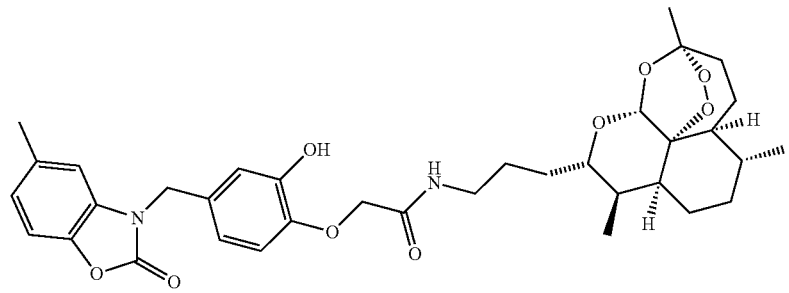 [SMILES: Cc1ccc2oc(=O)n(Cc3ccc(OCC(=O)NCCC[C@@H]4O[C@@H]5O[C@@]6(C)CC[C@H]7[C@H](C)CC[C@@H]([C@H]4C)[C@@]57OO6)c(O)c3)c2c1]

The present disclosure further provides a genus of novel affinity-tethering moieties covalently bound to a drug moiety or to an imaging moiety, either directly or optionally via a linker moiety, to covalently link the affinity-tethering moiety to a drug substance or to an imaging moiety. Further still, the present disclosure provides a therapeutic compound comprising a tethering moiety that competes with ISO-1 ((S,R)-3-(4-hydroxyphenyl)-4,5-dihydro-5-isoxazole acetic acid methyl ester) for binding to a tautomerase site of MIF, covalently bound to a drug moiety or to an imaging moiety, optionally via a linking moiety, wherein the therapeutic compound is able to block at least 50% of the binding of ISO-1 to the tautomerase site of MIF. The dissociation constant of ISO-1 is 14.5 µM.

Further still, the present disclosure provides a therapeutic compound comprising a teathering moiety capable of binding to a tautomerase site of MIF with a dissociation constant of between 10 mM and 1 pM, and covalently bound to a drug moiety, optionally via a linking moiety. Without being bound by theory, the disclosed pharmaceutical compounds are targeted to cancer cells or immune cells via the tethering moiety, wherein the tethering moiety hitch-hikes to or into its target cell while bound to endogenous MIF.

The present disclosure provides compounds, pharmaceutical compositions and methods of treatment using a pharmaceutical composition, comprising a tethering moiety that is capable of binding to a macrophage migration inhibitory factor MIF polypeptide, optionally linked to a linker moiety and further covalently bound to a therapeutic agent or imaging agent. More specifically, the present disclosure provides a genus of novel tethering moieties covalently bound to pharmacologic cytotoxic agents or imaging agents, either directly or optionally via a linker moiety, to covalently link the tethering moiety to the cytotoxic agent. The disclosed cytotoxic pharmaceutical compounds and imaging agents are targeted to preferentially gain cellular access into target cells via the MIF tethering moiety as an express pathway to a cellular nucleus without degradation on cellular lysozymes.

methyl)phenoxy)acetamide (compound 9) anticancer activity against three cultured lung cancer cell lines as measured by a Sulforhodamine B (SRB) assay. This assay measures anti-proliferative activity of a drug by quantifying the rate of total protein synthesis in response to pharmaceutical compounds.

Figure 1:
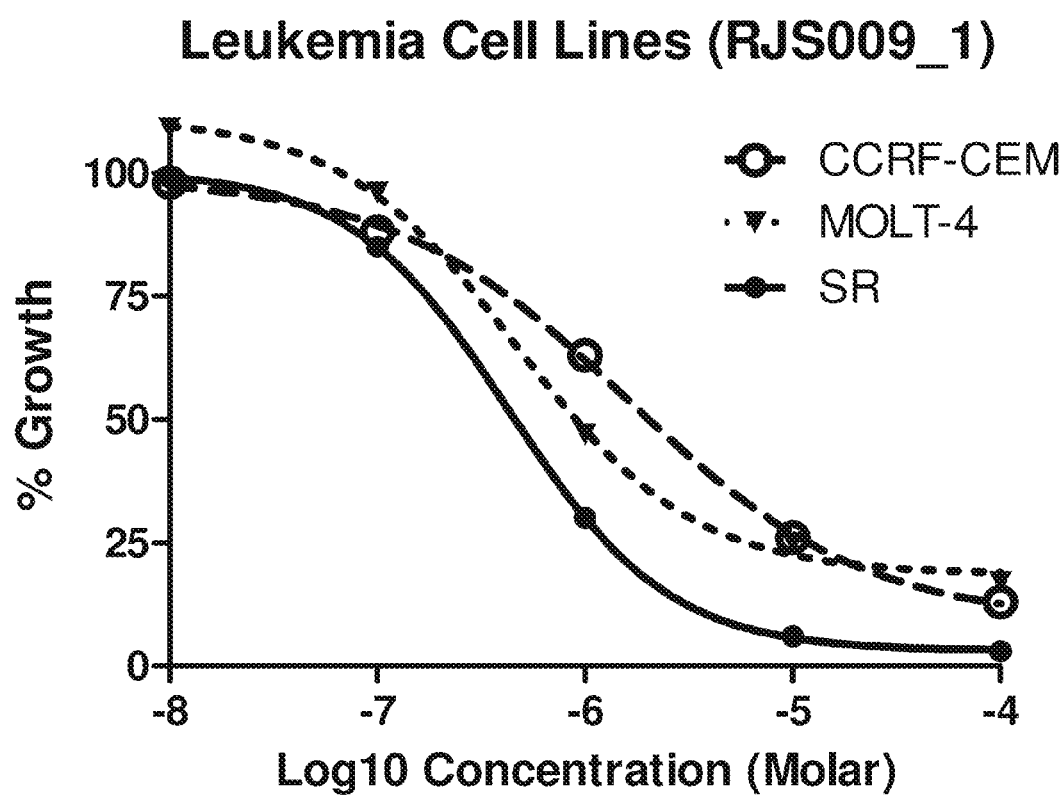
FIG. 1 shows a graph demonstrating N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide (compound 18) anticancer activity against three cultured leukemia and lymphoma cell lines, as measured by a Sulforhodamine B (SRB) assay. This assay measures anti-proliferative activity of a drug by quantifying the rate of total protein synthesis in response to pharmaceutical compounds.
Figure 2:
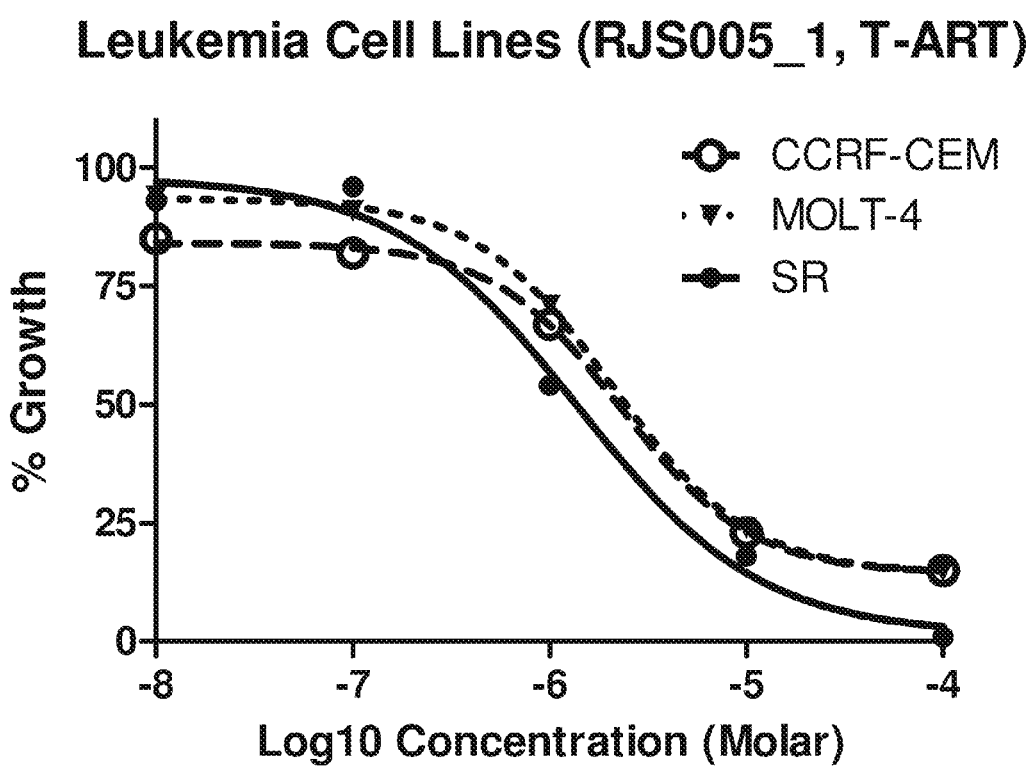
FIG. 2 shows a graph demonstrating 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyl-decahydro-12H-3,12-epoxy[1,2]dioxepino[4,3-i]isochromen-10-yl)propyl)acetamide (compound 11) anticancer activity against three cultured leukemia and lymphoma cell lines as measured by a Sulforhodamine B (SRB) assay. This assay measures anti-proliferative activity of a drug by quantifying the rate of total protein synthesis in response to pharmaceutical compounds.
Figure 3:
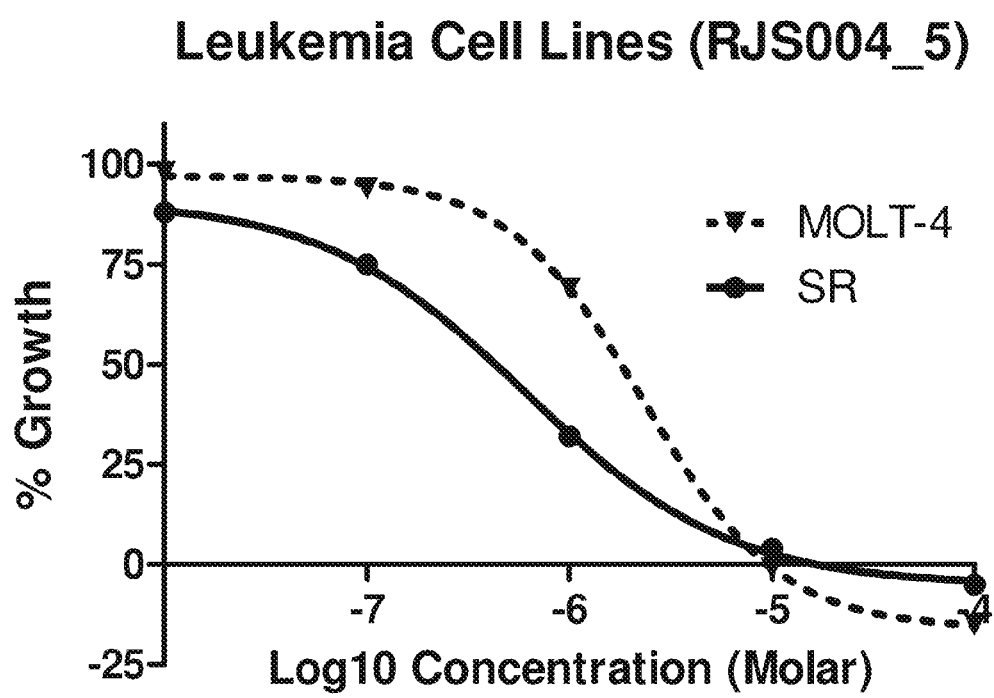
FIG. 3 shows a graph demonstrating N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) anticancer activity against two cultured leukemia and lymphoma cell lines as measured by a Sulforhodamine B (SRB) assay. This assay measures anti-proliferative activity of a drug by quantifying the rate of total protein synthesis in response to pharmaceutical compounds.
Figure 4:
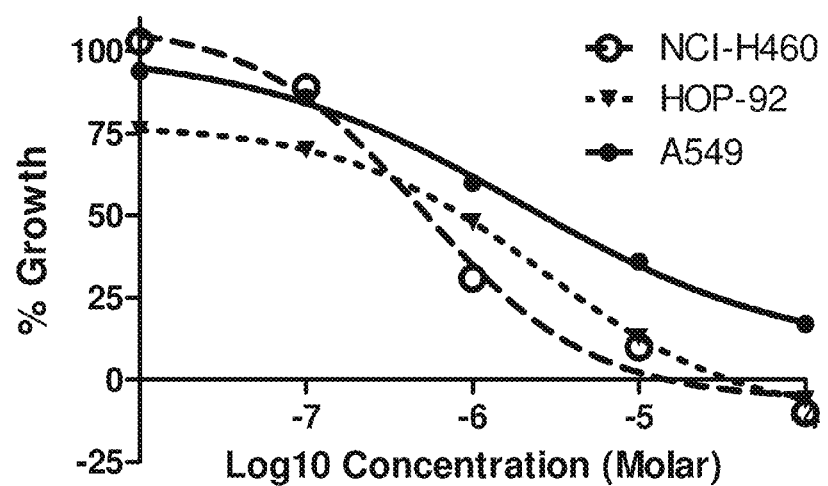
FIG. 4 shows a graph demonstrating N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide (compound 18) anticancer activity against three cultured lung cancer cell lines as measured by a Sulforhodamine B (SRB) assay. This assay measures anti-proliferative activity of a drug by quantifying the rate of total protein synthesis in response to pharmaceutical compounds.
Figure 5:
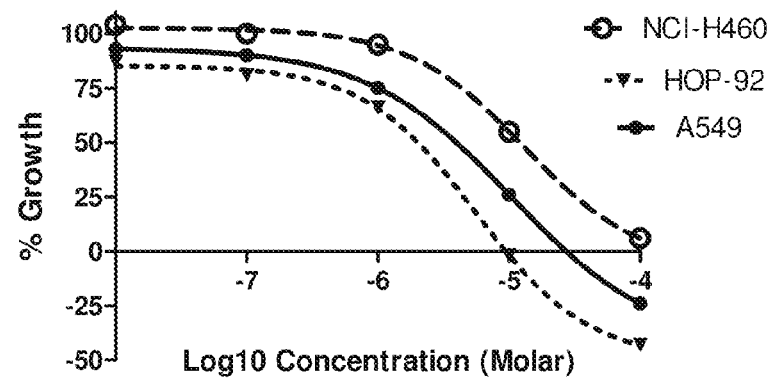
FIG. 5 shows a graph demonstrating 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyl-decahydro-12H-3,12-epoxy[1,2]dioxepino[4,3-i]isochromen-10-yl)propyl)acetamide (compound 11) anticancer activity against three cultured lung cancer cell lines as measured by a Sulforhodamine B (SRB) assay. This assay measures anti-proliferative activity of a drug by quantifying the rate of total protein synthesis in response to pharmaceutical compounds.
Figure 6:
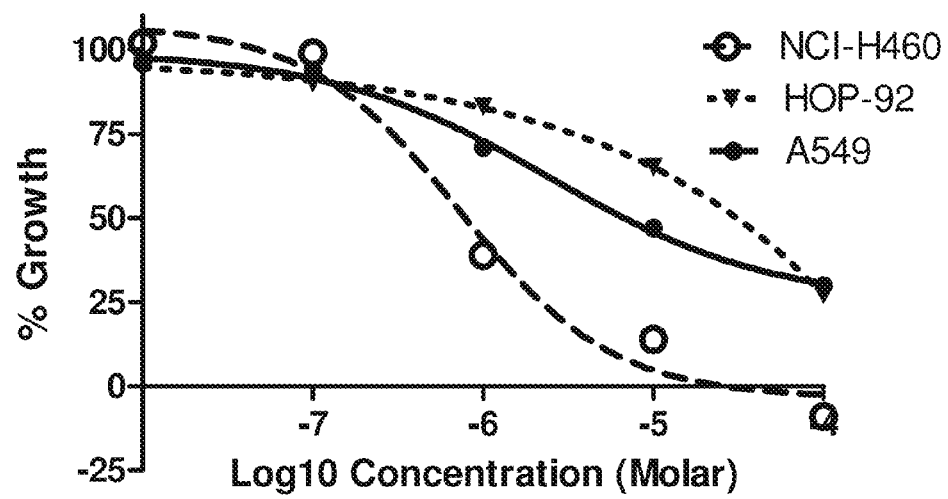
FIG. 6 shows a graph demonstrating N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3  (2H)-yl)
Figure 7:
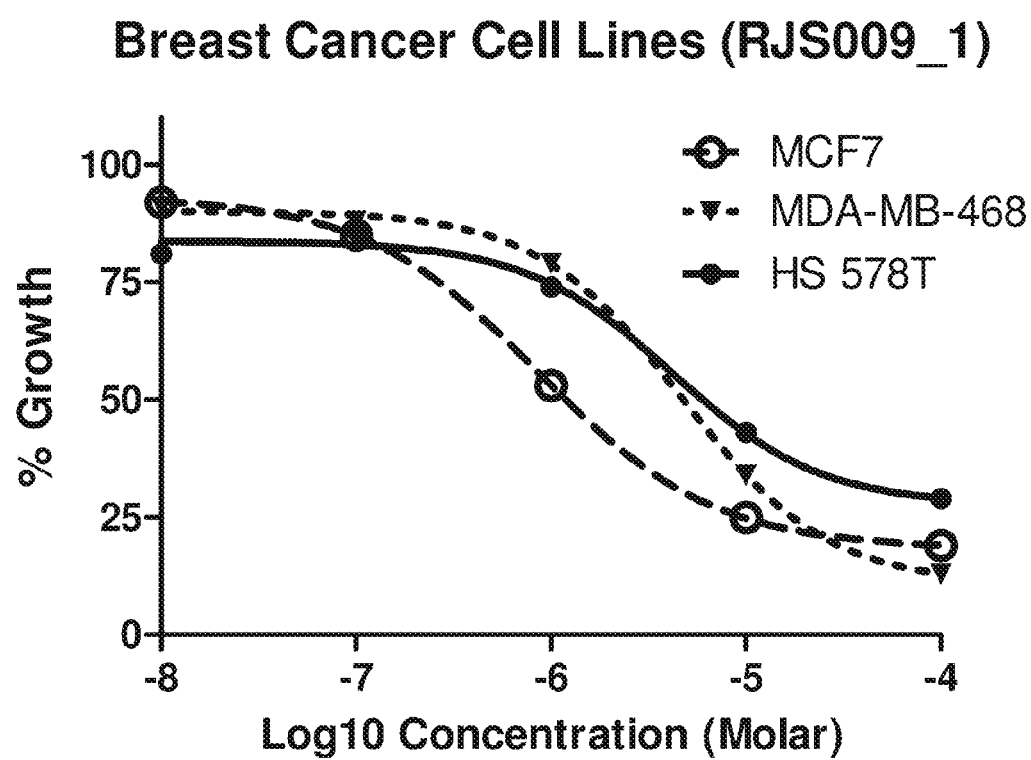

FIG. 7 shows a graph demonstrating N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide (compound 18) anticancer activity against three cultured breast cancer cell lines as measured by a Sulforhodamine B (SRB) assay. This assay measures anti-proliferative activity of a drug by quantifying the rate of total protein synthesis in response to pharmaceutical compounds.

Figure 8:
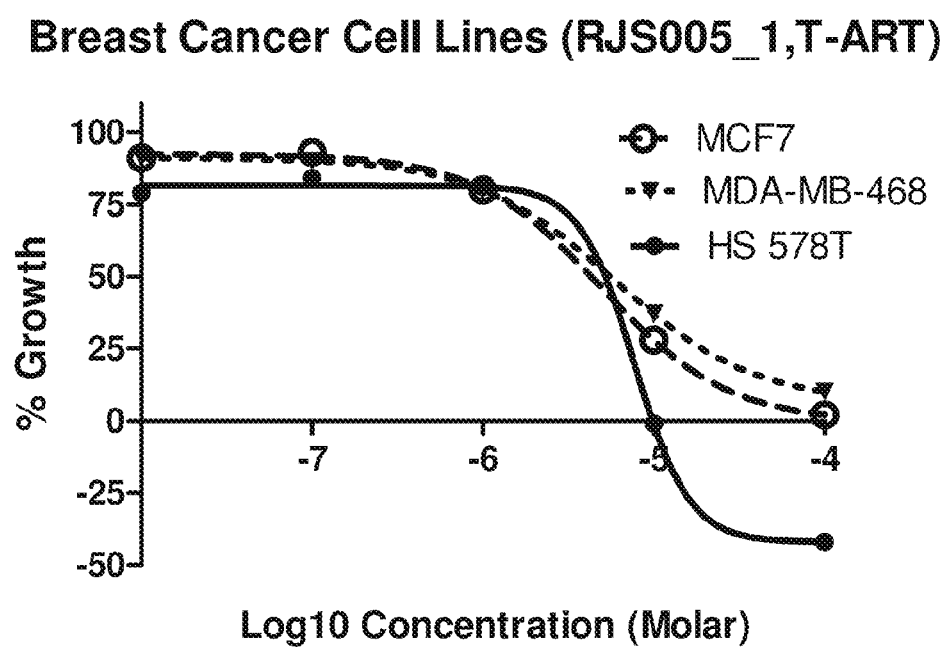

FIG. 8 shows a graph demonstrating 2-(2-hydroxy-4-((5-methyl-2-oxobenzo[d]oxazol-3(2H)-yl)methyl)phenoxy)-N-(3-43R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11) anticancer activity against three cultured breast cancer cell lines as measured by a Sulforhodamine B (SRB) assay. This assay measures anti-proliferative activity of a drug by quantifying the rate of total protein synthesis in response to pharmaceutical compounds.

Figure 9:
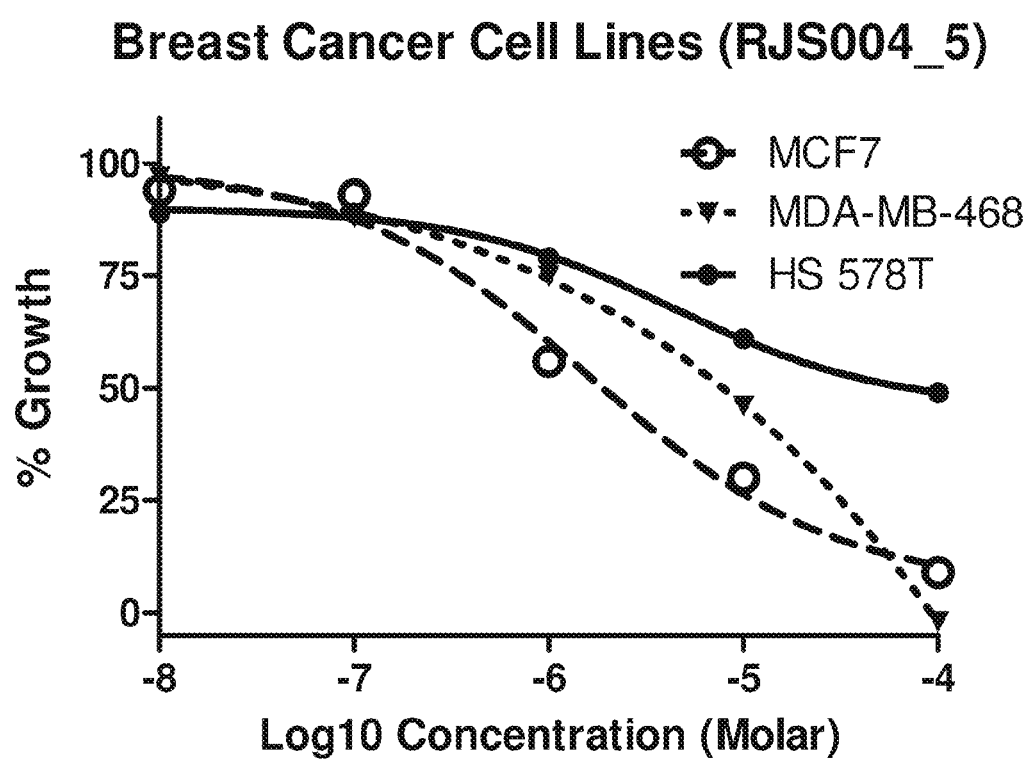

FIG. 9 shows a graph demonstrating N-((2R,3R,4R,6R)-6-4(1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) anticancer activity against three cultured breast cancer cell lines as measured by a Sulforhodamine B (SRB) assay. This assay measures anti-proliferative activity of a drug by quantifying the rate of total protein synthesis in response to pharmaceutical compounds.

Figure 10:
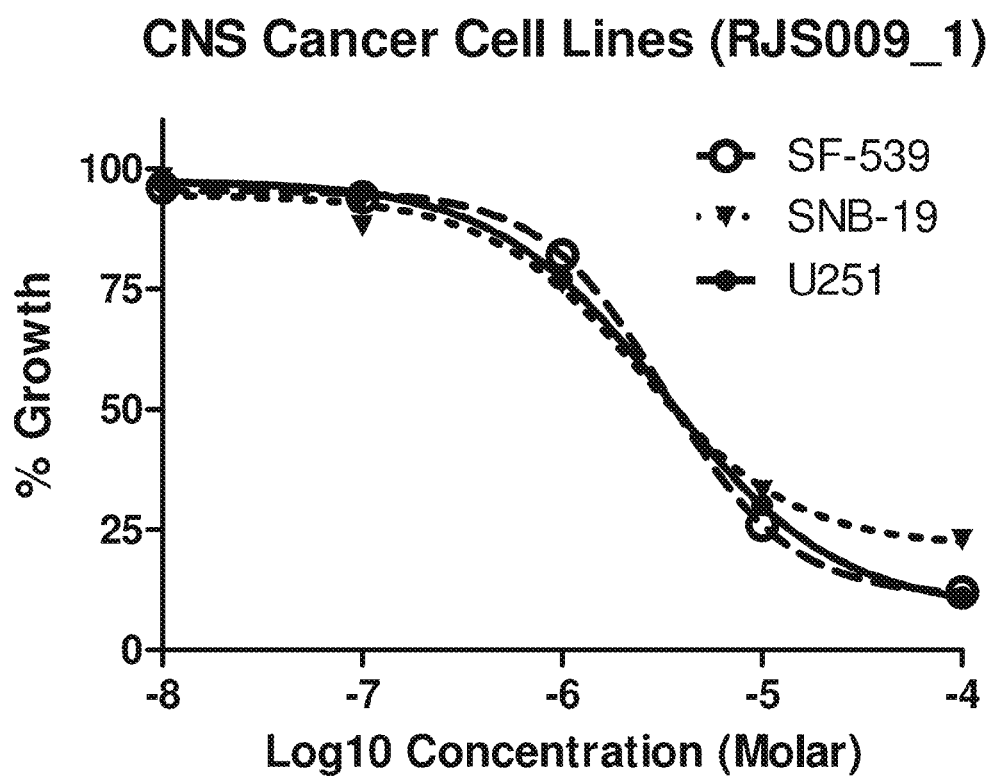

FIG. 10 shows a graph demonstrating N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide (compound 18) anticancer activity against three cultured CNS cancer cell lines as measured by a Sulforhodamine B (SRB) assay. This assay measures anti-proliferative activity of a drug by quantifying the rate of total protein synthesis in response to pharmaceutical compounds.

Figure 11:
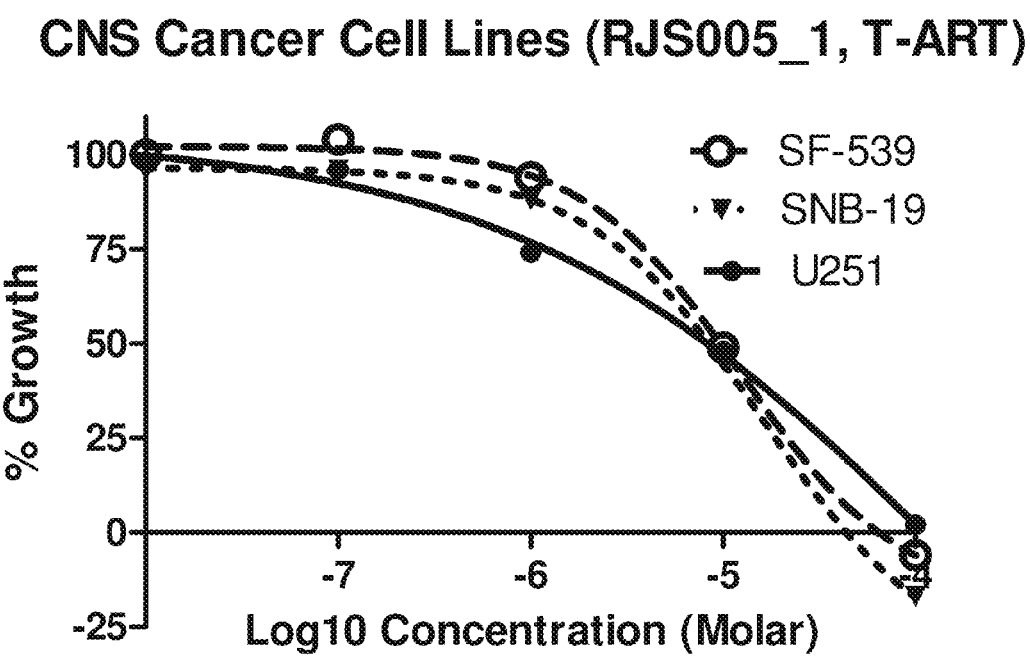

FIG. 11 shows a graph demonstrating 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11) anticancer activity against three cultured CNS cancer cell lines as measured by a Sulforhodamine B (SRB) assay. This assay measures anti-proliferative activity of a drug by quantifying the rate of total protein synthesis in response to pharmaceutical compounds.

Figure 12:
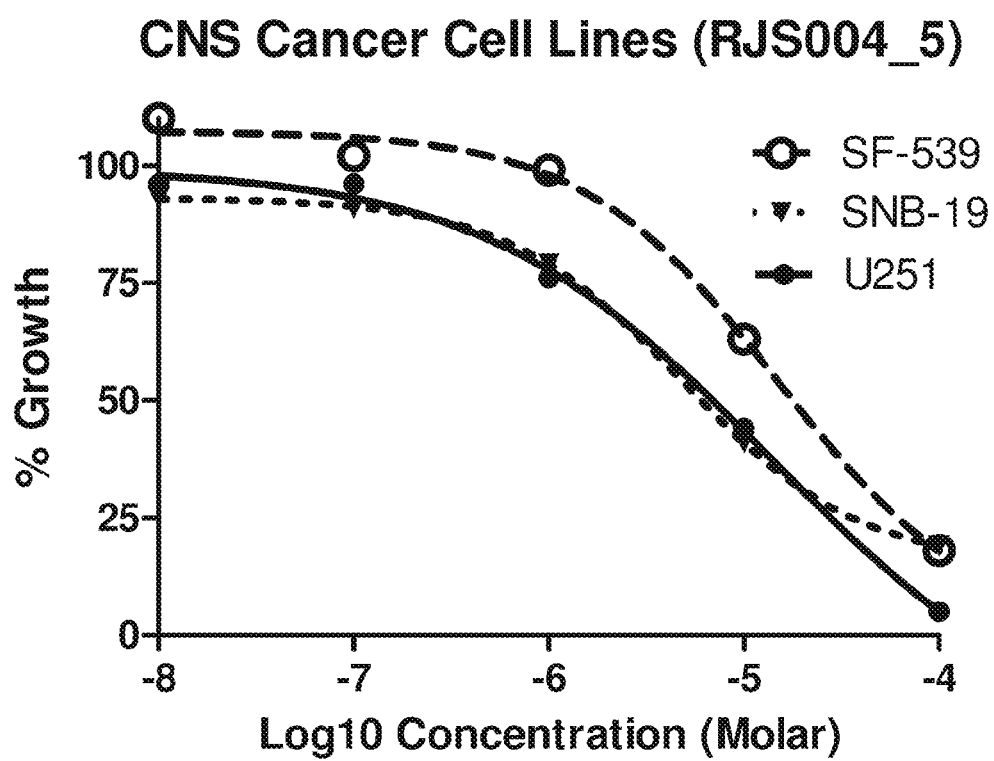

FIG. 12 shows a graph demonstrating N-((2R,3R,4R,6R)-6-4(1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) anticancer activity against three cultured CNS cancer cell lines as measured by a Sulforhodamine B (SRB) assay. This assay measures anti-proliferative activity of a drug by quantifying the rate of total protein synthesis in response to pharmaceutical compounds.

Figure 13:
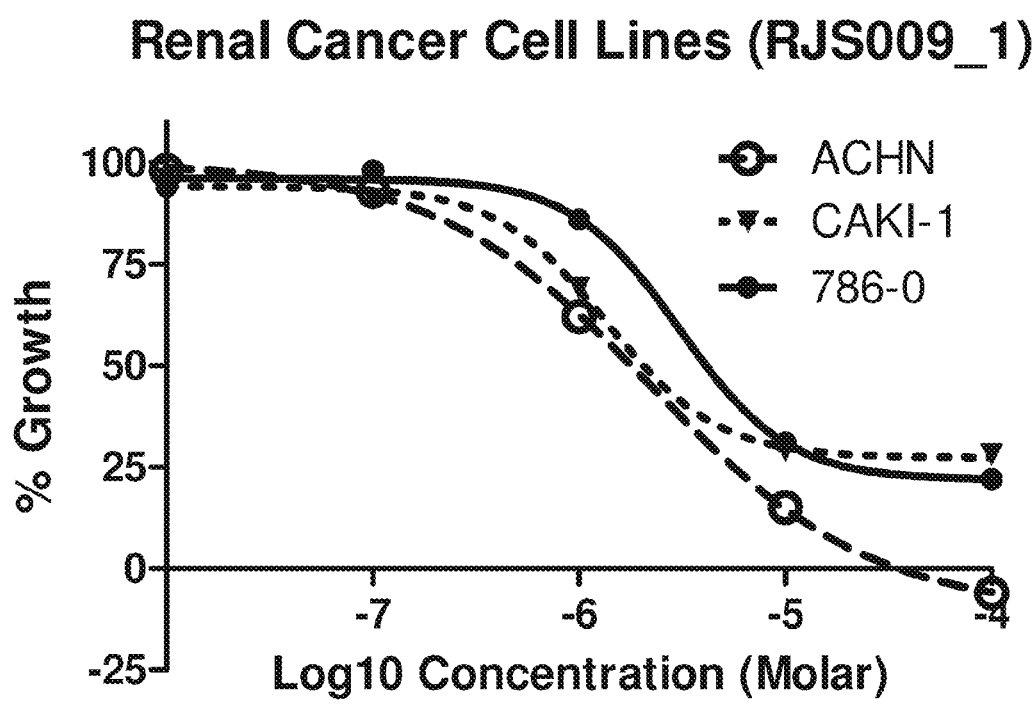

FIG. 13 shows a graph demonstrating N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide (compound 18) anticancer activity against three cultured renal cancer cell lines as measured by a Sulforhodamine B (SRB) assay. This assay measures anti-proliferative activity of a drug by quantifying the rate of total protein synthesis in response to pharmaceutical compounds.

Figure 14:
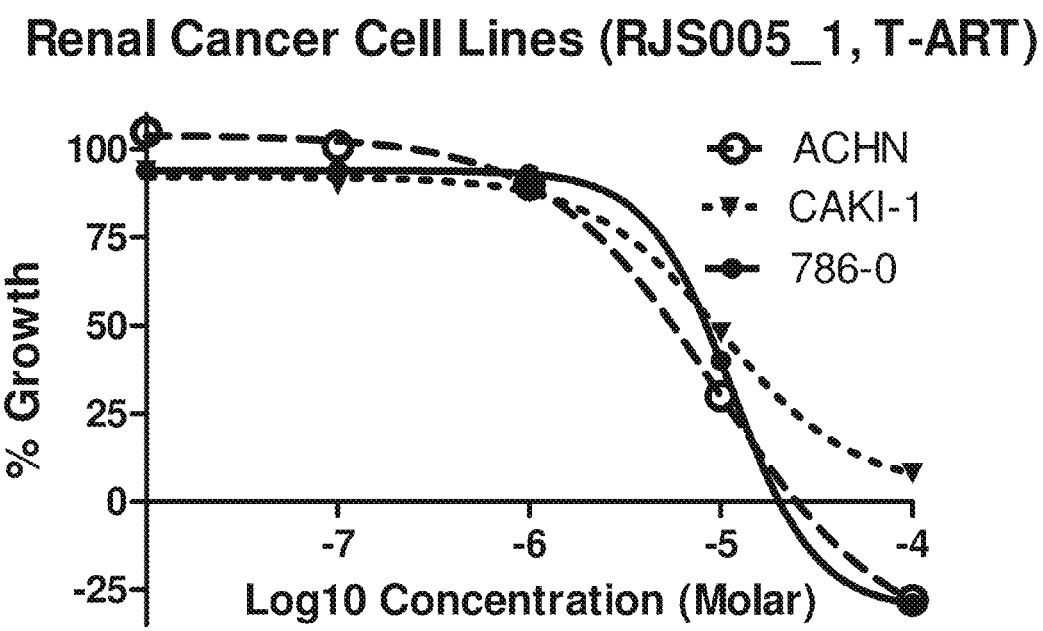

FIG. 14 shows a graph demonstrating 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11) anticancer activity against three cultured renal cancer cell lines as measured by a Sulforhodamine B (SRB) assay. This assay measures anti-proliferative activity of a drug by quantifying the rate of total protein synthesis in response to pharmaceutical compounds.

Figure 15:
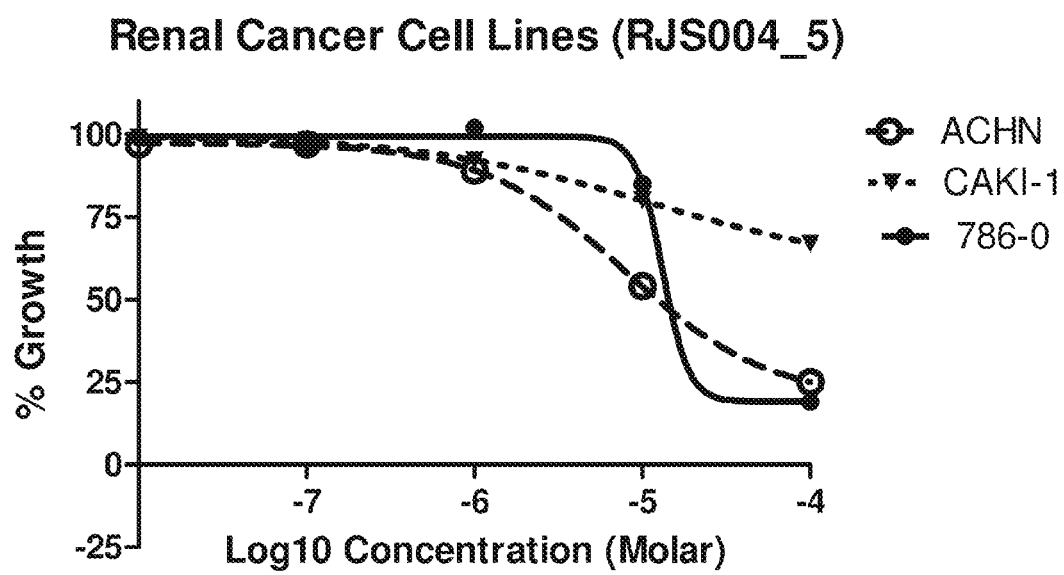

FIG. 15 shows a graph demonstrating N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) anticancer activity against three cultured renal cancer cell lines as measured by a Sulforhodamine B (SRB) assay. This assay measures anti-proliferative activity of a drug by quantifying the rate of total protein synthesis in response to pharmaceutical compounds.

Figure 16:
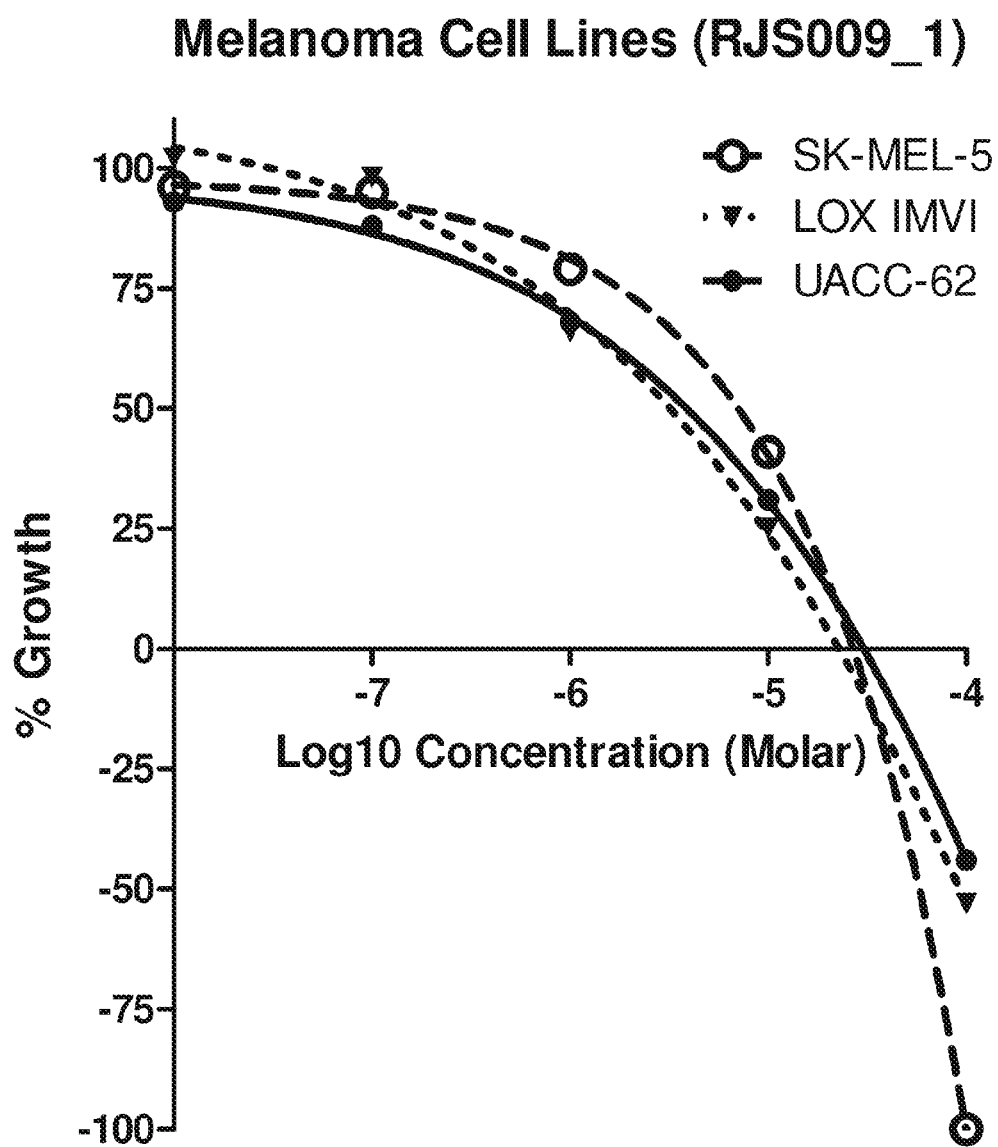

FIG. 16 shows a graph demonstrating N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide (compound 18) anticancer activity against three cultured melanoma cell lines as measured by a Sulforhodamine B (SRB) assay. This assay measures anti-proliferative activity of a drug by quantifying the rate of total protein synthesis in response to pharmaceutical compounds.

Figure 17:
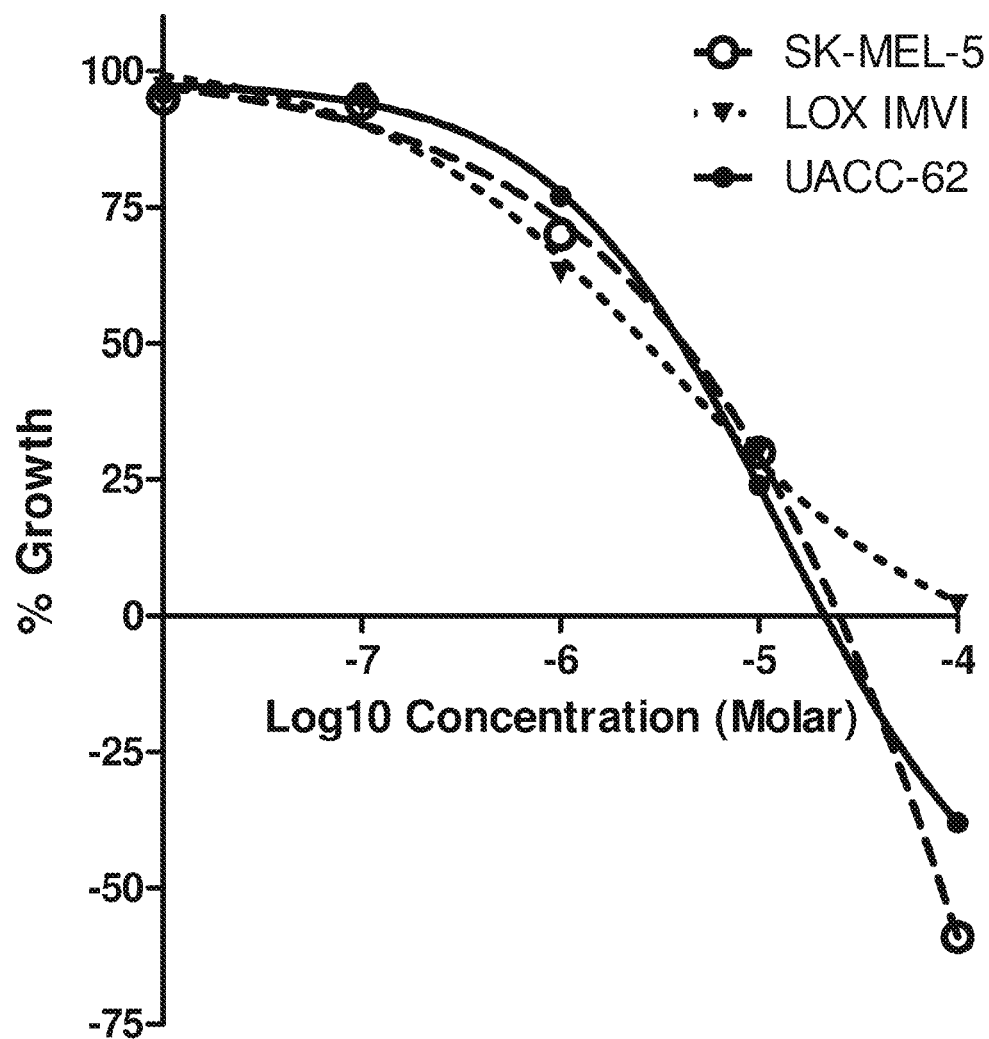

FIG. 17 shows a graph demonstrating 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11) anticancer activity against three cultured melanoma cell lines as measured by a Sulforhodamine B (SRB) assay. This assay measures anti-proliferative activity of a drug by quantifying the rate of total protein synthesis in response to pharmaceutical compounds.

Figure 18:
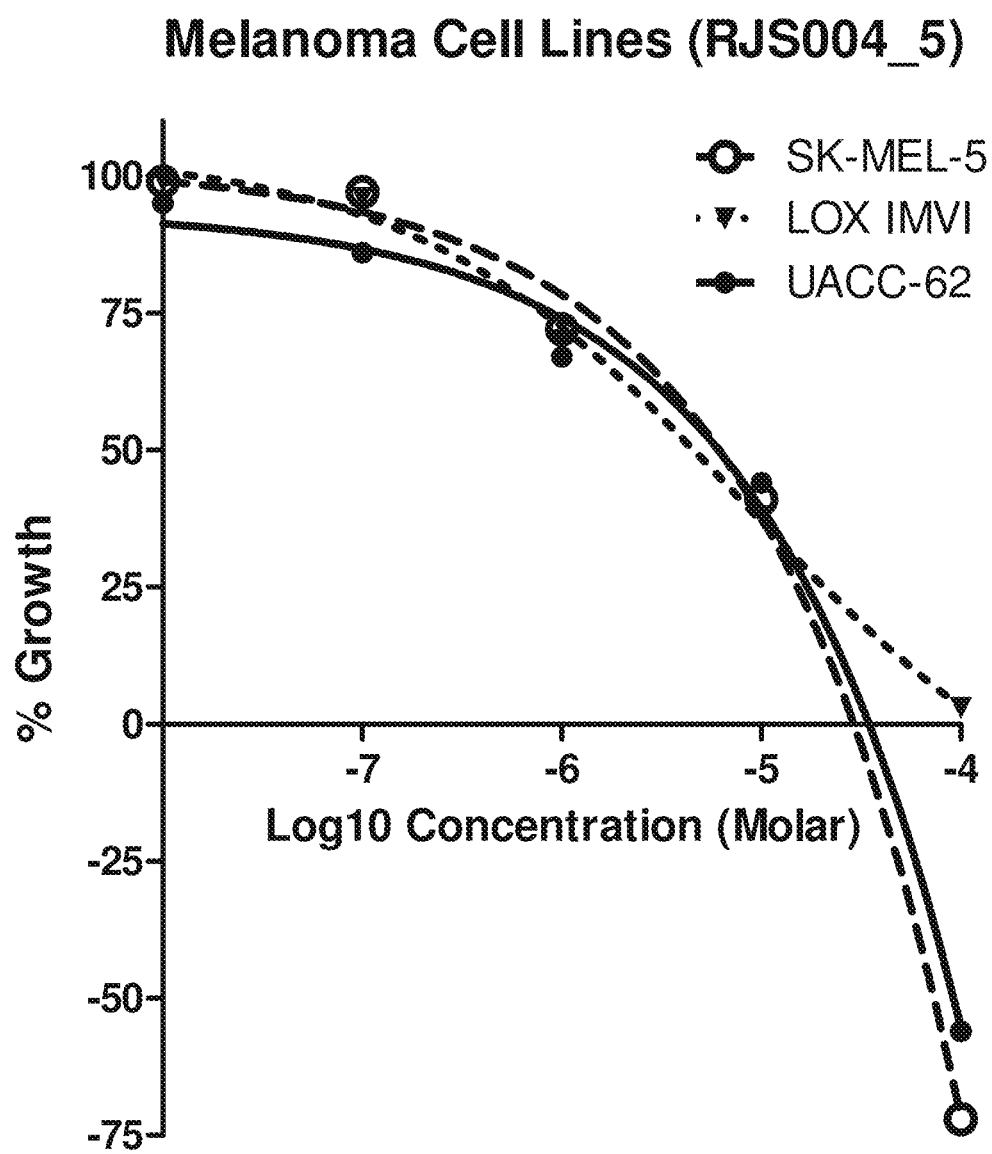

FIG. 18 shows a graph demonstrating N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) anticancer activity against three cultured melanoma cell lines as measured by a Sulforhodamine B (SRB) assay. This assay measures anti-proliferative activity of a drug by quantifying the rate of total protein synthesis in response to pharmaceutical compounds.

Figure 19:
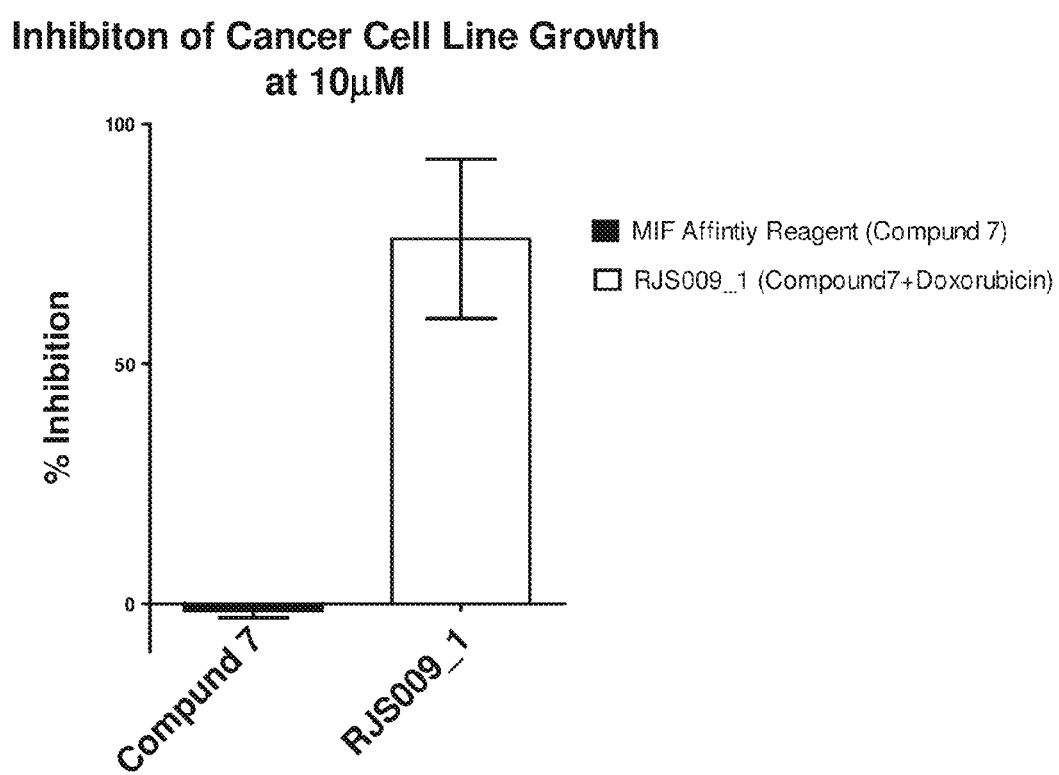

FIG. 19 shows a graph comparing the inhibition of cancer cell growth as evaluated by a Sulforhodamine B (SRB) assay using either the MIF tethering agent alone (compound 7 or (2-hydroxy-4-[(5-methyl-2-oxo-1,3-benzoxazol-3(2H)-yl)methyl]phenoxy)acetic acid) in the absence of an attached drug warhead or a MIF affinity compound coupled to the anti-cancer drug Doxorubicin (RJS009_1/compound 18). These data are accumulated from inhibition of 17 cancer cell lines using a concentration of 10 µM for the tested compounds. The cell lines used are detailed in the methods associated with Assay Example 1 (below). The average % inhibition across these cell lines is shown. The standard deviation across these cell lines is shown as the error bars. These data demonstrate that MIF-affinity-tethering agent alone (compound 7 or (2-hydroxy-4-[(5-methyl-2-oxo-1,3-benzoxazol-3(2H)-yl)methyl]phenoxy)acetic acid) has little if any potency in a Sulforhodamine B (SRB) cellular proliferation assay at a 10 µM concentration.

Figure 20:
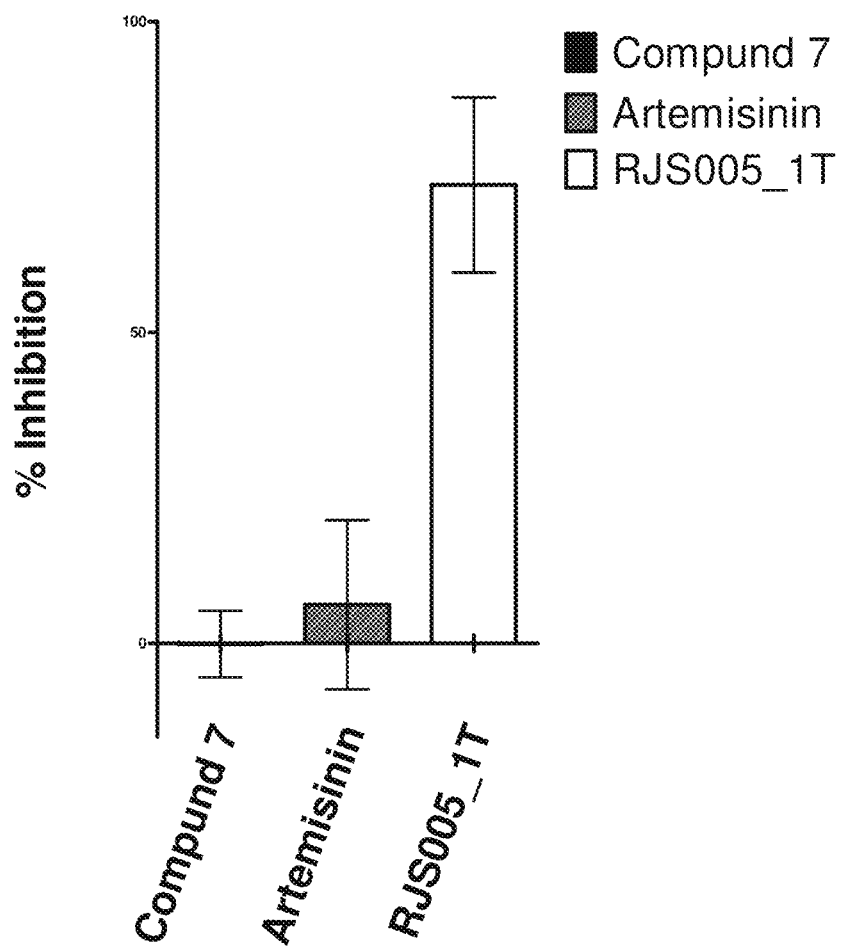

FIG. 20 shows a graph comparing inhibition of cancer cell growth as measured by a Sulforhodamine B (SRB) assay using either MIF-affinity-tethering agent alone (compound 7), Artemisinin alone (toxic drug) or a disclosed MIF affinity compound 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11) made by covalently coupling Artemisinyl propylamine to the MIF affinity tethering agent (compound 7). These data are accumulated from inhibition of 14 diverse cancer cell lines at 10 µM for the tested compounds. The cell lines used are detailed in the methods associated with Assay Example 1 (below). The average % inhibition across cell lines are shown. The standard deviation across these cell lines is shown as the error bars. These data demonstrate that the MIF tethering moiety (compound 7 or (2-hydroxy-4-[(5-methyl-2-oxo-1,3-benzoxazol-3(2H)-yl)methyl]phenoxy) acetic acid) and Artemisinin as a toxic agent (Artemisinyl propylamine) have little potency as individual compounds in a Sulforhodamine B (SRB) cellular proliferation assay at 10 µM. Only when these two moieties, MIF-affinity tethering agent (compound 7) and Artemisinin moiety (Artemisinyl propylamine), are covalently linked using dicyclohexylcarbodiimide (DCC) is a dehydrating agent is substantial anti-cancer activity observed. The resultant molecule of this synthesis reaction is 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11).

Figure 21:
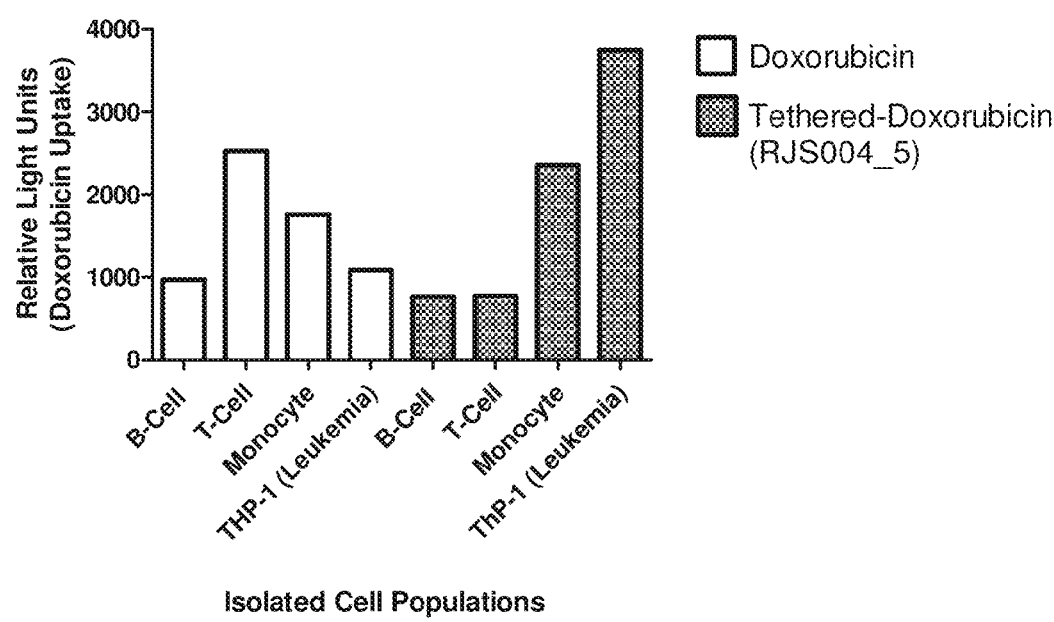

FIG. 21 shows a graph demonstrating that N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) is selectively taken up by cancer cells. This graph demonstrates the preferential uptake of a MIF affinity-tethered fluorescent drug substance/imaging agent uptake by THP-1 leukemia cells over non-cancerous cells when a mixed population of cells is treated with N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9). This imaging based assay was performed using a flow cytometer to separate distinct cellular populations pretreated with drug substances where a cancer cell line (THP-1 leukemia cells) is added to mixture of normal non-cancerous PBMC cells (B-cells, T-Cells, Monocytes, etc.). This assay measures the cellular uptake of a fluorescent compound (compound 7-Doxorubicin N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide/(compound 9) or Doxorubicin). Doxorubicin, by itself, has little preference for the cancer cell line in this assay as observed by preferential distribution of the untethered Doxorubicin into the T-Cell population. Conversely, N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) demonstrates drug uptake into the monocytic cancer cell line THP-1.

Figure 22:
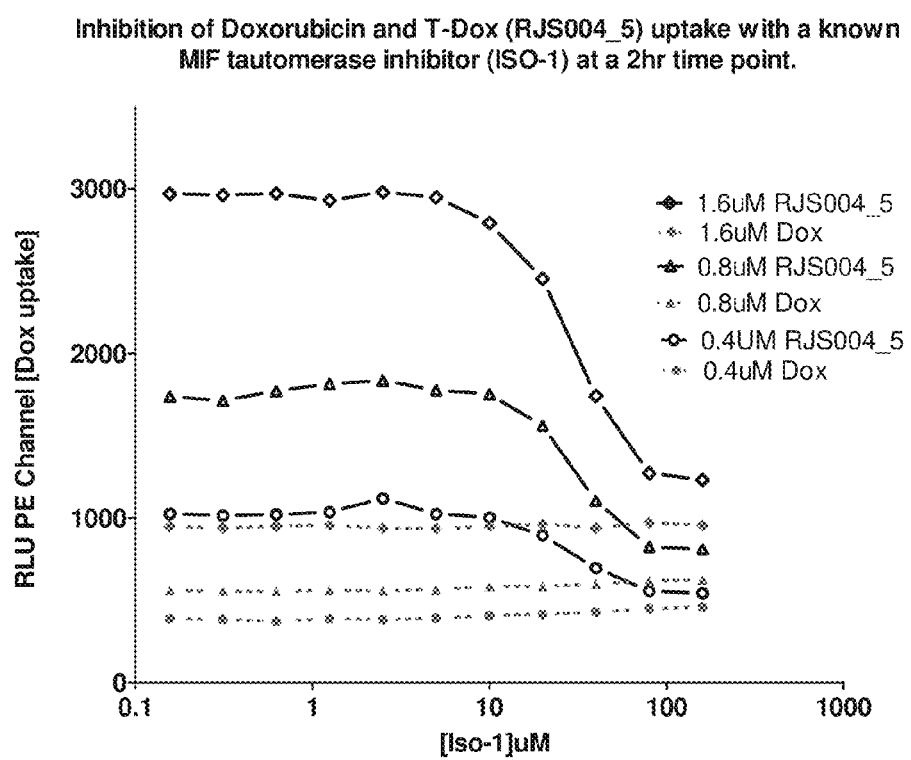

FIG. 22 shows a graph demonstrating the selective uptake of N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) by THP-1 leukemia cells is inhibited by the MIF tautomerase inhibitor (S,R)-3-(4-Hydroxyphenyl)-4,5-dihydro-5-isoxazole acetic acid, methyl ester (ISO-1). This assay measures cellular uptake and imaging of cancer cells using doxorubicin as a fluorescent compound (tethered-Doxorubicin (N-((2R,3R,4R,6R)-6-4(1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide-(compound 9) or Doxorubicin). Compound uptake is evaluated and quantified by flow cytometetry. Doxorubicin uptake was not inhibited ISO-1.

Figure 23:
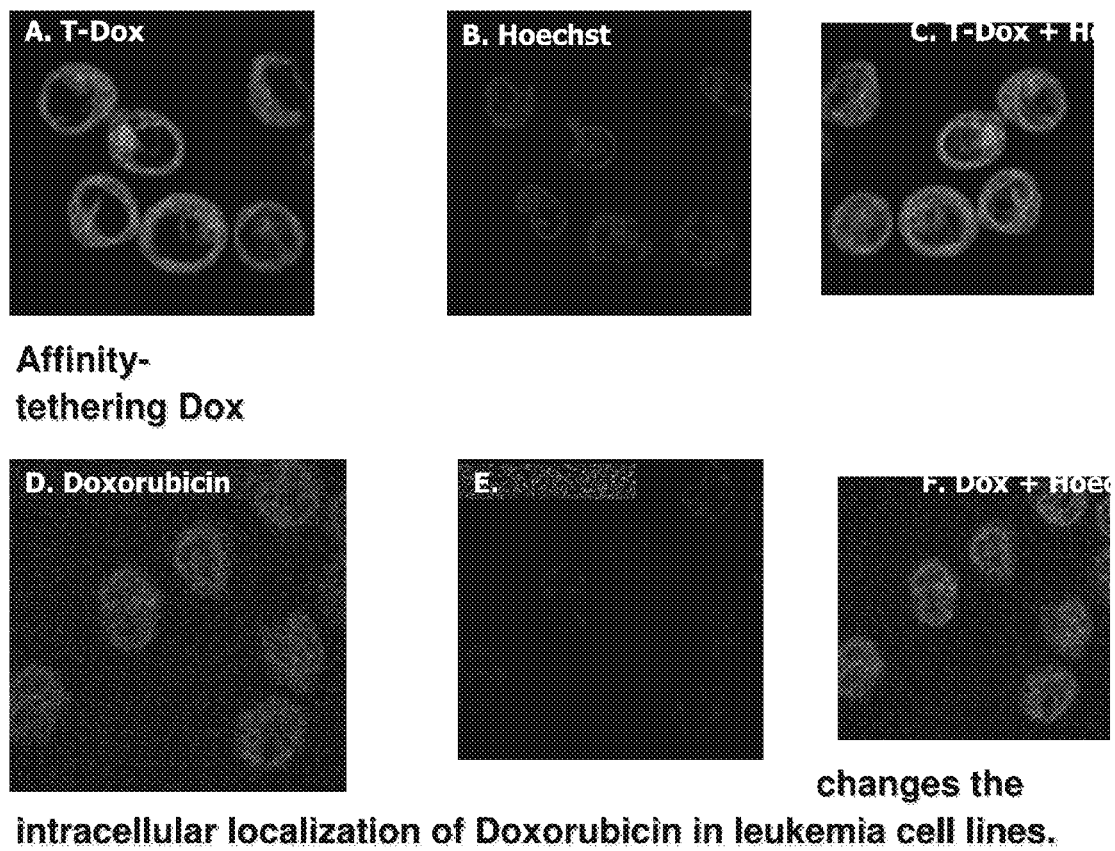

FIG. 23 shows a microscopic examination of cellular localization of N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) in cultured leukemia cells. A comparison of the cellular import of N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) to Doxorubicin is shown. THP-1 cells were treated with 0.8 µM T-Dox or 0.8 µM Doxorubicin for 2 hrs at 37° C. The cells were then stained with Hoechst vital dye for 30 minutes. Cellular images were recorded using a Zeiss LSM 510 Meta Confocal Microscope 40×. N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) panels A, B, C, Doxorubicin only, panels D, E, G. Doxorubicin compound fluorescence was observed as green, Hoescht Vital Dye (Nucleus) Blue. These data demonstrates that (N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)

methyl)phenoxy)acetamide compound 9) has a substantially altered intracellular localization in leukemia cells when compared to Doxorubicin.

Figure 24:
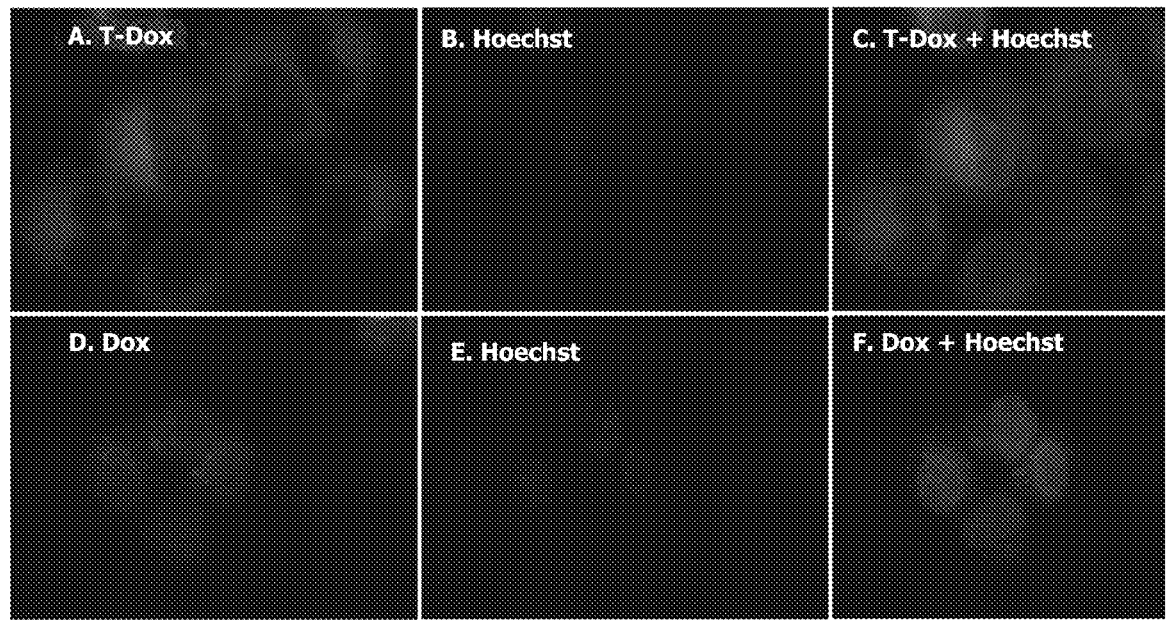

FIG. 24 shows a microscopic examination of cellular localization in cultured lung cancer cells of the cellular import of N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) to Doxorubicin. 549 lung cancer cells were treated with 0.8 µM N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) or 0.8 µM Doxorubicin for 2 hrs at 37° C. The cells were then stained with Hoechst vital dye for 30 minutes. Cellular images were recorded using a Zeiss LSM 510 Meta Confocal Microscope 40× N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide (compound 9) panels A, B, C, Doxorubicin, panels D, E, G. Doxorubicin compound fluorescence is observed as red, Hoescht Vital Dye (Nucleus) blue. These data demonstrates that (N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-4-((5-methyl-2-oxobenzo[D]oxazol-3(2H)-yl)methyl)phenoxy)acetamide-compound 9) had a substantially altered intracellular localization in lung cancer cells when compared to Doxorubicin.

Figure 25A:
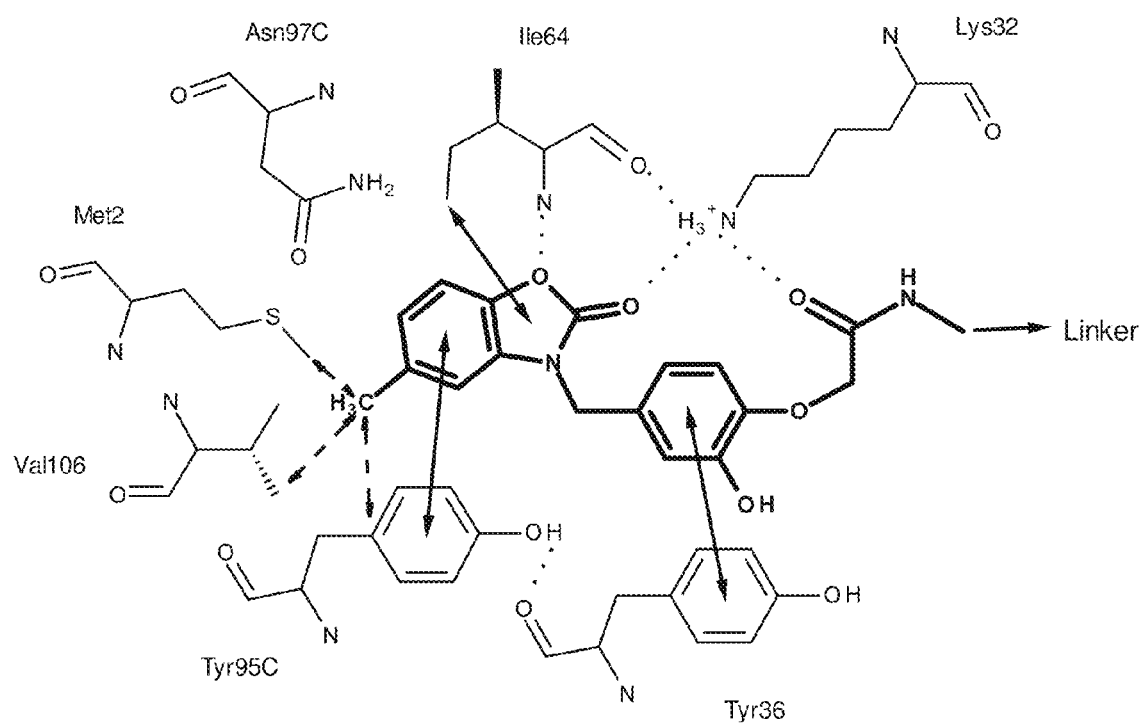
Figure 25B:
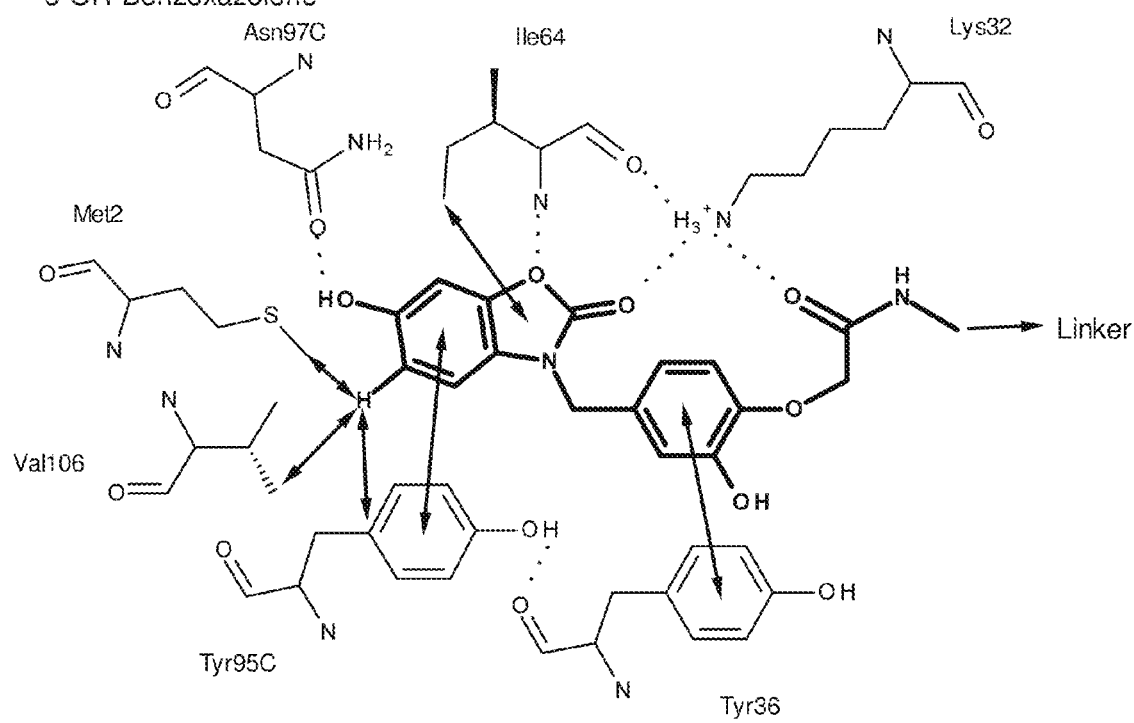
Figure 25C:
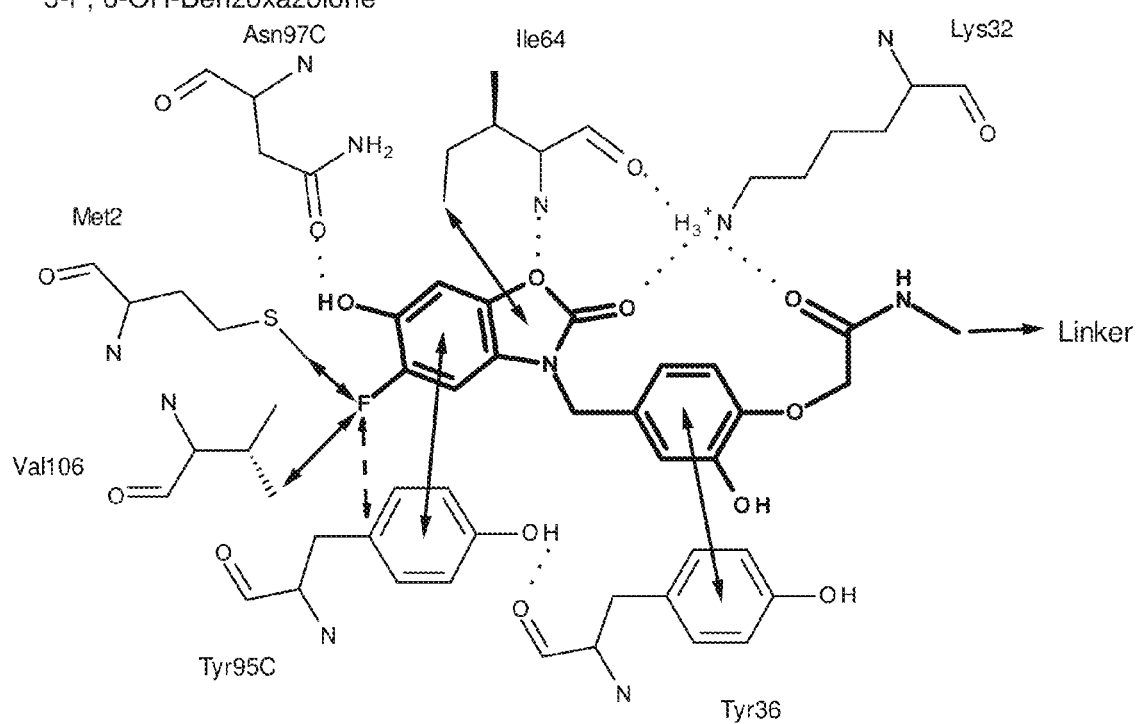

FIG. 25 shows three diagram panels, A, B and C, of interactions of benzoxazalone affinity compounds with MT tautomerase binding sites. Affinity compounds are shown in bold lines. Amino acid residues from MIF monomer (FIG. 25A) are displayed in thin lines labeled by three-letter code with residue numbers, residues from adjacent monomer (FIG. 25C) are labeled respectively. Hydrogen bonds are shown by dotted lines. Favorable hydrophobic and π interactions are shown by solid arrows, unfavorable short van der Waals contacts are indicated by dashed arrows.

DETAILED DESCRIPTION

The present disclosure often uses names for pharmaceutical compounds that are composed of a novel tether moiety or sometimes also called an affinity reagent or an affinity compound. The disclosed pharmaceutical composition optionally also sometimes contains a linker to link the tether to the toxic moiety or drug payload. Table 1 below provides a key to the compound naming system.

TABLE 1

| Name | Affinity tether | Linker | Payload |
|---|---|---|---|
| RJS04_5 | 5-Me-Benzoxazolone | — | Doxorubicin |
| RJS09_1 | 5-Me-Benzoxazolone | dPEG2 | Doxorubicin |
| RJS010_2 | 5-Me-Benzoxazolone | dPEG4 | Doxorubicin |
| ART-OH | — | —OH | Artemisinin |
| RJS05_1 | 5-Me-Benzoxazolone | — | Artemisinin |
| RJS05_2 | 5-Me-Benzoxazolone | dPEG2 | Artemisinin |
| RJS05_3 | 5-Me-Benzoxazolone | dPEG2 | Artemisinin |
| RJS012_1 | 5-Me-Benzoxazolone | dPEG2 | Iressa ® (Gefitinib) |
| RJS012_3 | 6-OH-Benzoxazolone | dPEG2 | Iressa ® (Gefitinib) |
| RJS012_5 | 5-F, 6-OH-Benzoxazolone (in synthesis) | dPEG2 | Iressa ® (Gefitinib) |
| RJS013-2 | 5-Me-Benzoxazolone | dPEG2 | Tarceva ®(Erlotinib) |

The present disclosure provides compounds, pharmaceutical compositions and methods of treatment using a pharmaceutical composition comprising a tethering moiety that is capable of binding to a macrophage migration inhibitory factor (MIF) polypeptide, optionally linked to a linker moiety and further covalently bound to a drug or imaging moiety. Preferably, the tethering moiety comprises a moiety from formula (1)

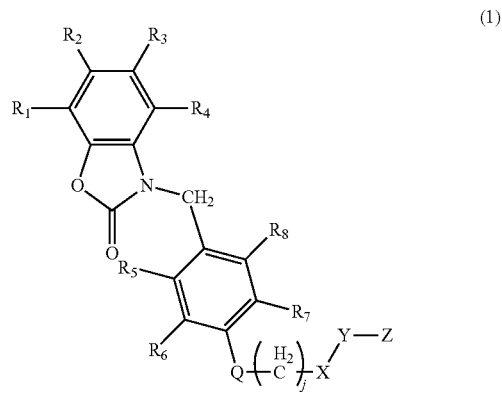

wherein Q is selected from the group consisting of O, S, N(R9), and C(R9)R10;

X is selected from the group consisting of nothing, O, S, N(R9), N(R9)N(R10), $(CH_2)_k$-$(OCH2CH_2)_l$, CR9R10-CR11R12, and C(O);

Y is selected from the group consisting of nothing, O, S, N(R11), N(R11)N(R12), —N=, C(O), C(O)O—, C(O)N(R9)-, C(O)N(R9)N(R10)-, C(O)N(R9)N=, C(O)$(CH_2)_m$-S—, and C(O)$(CH_2)_m$-S—S—;

R1, R2, R3, R4, R5, R6, R7 and R8 are each independently selected from the group consisting of H, hydroxyl, C1-C8 alkyl, alkenyl, alkynyl, substituted C1-C8 alkyl, alkenyl, alkynyl, C1-C8 acyl, substituted C1-C8 acyl, C1-C8 alkoxy, substituted C1-C8 alkoxy, C1-C8 ester, substituted C1-C8 ester, $(CH_2)_n$-phenyl, substituted $(CH_2)_n$-phenyl, $(CH_2)_n$-heterocycle, substituted $(CH_2)_n$-hetero cycle, halogen, cyano, nitro, amino, (CH$_2$)n-monoalkylamine, substituted (CH$_2$)n-monoalkylamine, (CH$_2$)n-dialkylamine, substituted (CH$_2$)n-dialkylamine, carboxylic acid, (CH$_2$)n-dialkylamine, (CH$_2$)n-monoalkylamide, substituted (CH$_2$)n-monoalkylamide, (CH$_2$)n-dialkylamide, and substituted (CH$_2$)n-dialkylamide; wherein the substitutions are selected from the group consisting of C1-8 alkyl, C1-8 alkenyl, halo-substituted aryl, aryl, hydroxyl, hydrogen, C1-8 alkoxy, and combinations thereof.

R9, R10, R11, and R12 are each independently selected from the group consisting of H, hydroxyl, C1-C8 alkyl, substituted C1-C8 alkyl, alkenyl, alkynyl, (CH$_2$)$_n$-phenyl, substituted (CH$_2$)n-phenyl, (CH$_2$)n-heterocycle, and substituted (CH$_2$)$_n$-heterocycle; wherein the substitutions are selected from the group consisting of C1-8 alkyl, C1-8 alkenyl, halo-substituted aryl, aryl, hydroxyl, hydrogen, C1-8 alkoxy, and combinations thereof.

j, m, and n are each integers independently from 0 to 8, k is an integer from 0 to 2, 1 is an integer from 1 to 8; and Z represents the drug or imaging moiety.

Preferably, Q is O; j is 1; X is nothing; Y is C(O)N(R9)N═; R1, R2, R4, R5, R7, R8, and R9 are hydrogen; R3 is methyl; R6 is hydroxyl; and Z is Doxorubicin. Preferably, the compound is N'—((Z)-1-((2R,4S)-4-(((2S,4S,5S,6S)-4-amino-5-hydroxy-6-methyltetrahydro-2H-pyran-2-yl)oxy)-5-hydroxy-7-methoxy-2-methyl-6,11-dioxo-1,2,3,4,6,11-hexahydrotetracen-2-yl)-2-hydroxyethylidene)-2-(2-hydroxy-4-((5-methyl-2-oxobenzo[d]oxazol-3(2H)-yl)methyl)phenoxy)acetohydrazide:

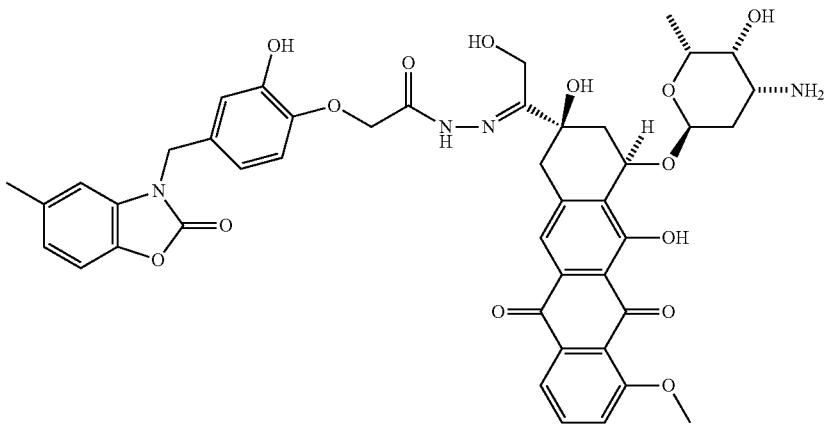 [SMILES: COc1cccc2c1C(=O)c1c(cc3c(c1O)[C@H](O[C@@H]1C[C@@H](N)[C@@H](O)[C@@H](C)O1)C[C@@](O)(/C(CO)=N/NC(=O)COc1ccc(Cn4c(=O)oc5ccc(C)cc54)cc1O)C3)C2=O]

Preferably, Q is O; j is 1; X is C(O); Y is nothing; R1, R2, R4, R5, R7, and R8 are hydrogen; R3 is methyl; R6 is hydroxyl and Z is Doxorubicin. Preferably, the compound Preferably, Q is O; j is 1; X is C(O); Y is nothing; R2, R4, R5, R7, and R8 are hydrogen; R3 is methyl; R6 is hydroxyl and Z is artemisinin. Preferably, the compound is:

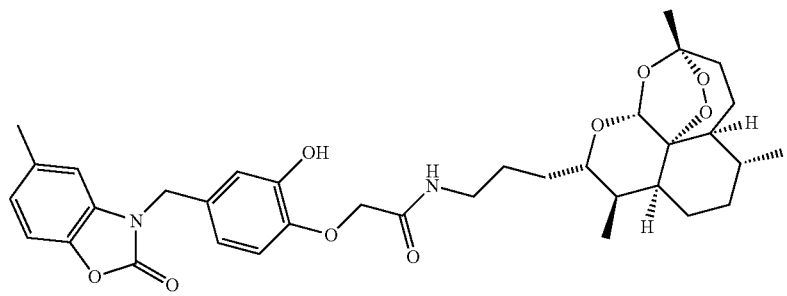 [SMILES: Cc1ccc2oc(=O)n(Cc3ccc(OCC(=O)NCCC[C@@H]4O[C@@H]5O[C@]6(C)CC[C@H]7[C@H](C)CC[C@@H]([C@H]4C)[C@@]57OO6)c(O)c3)c2c1]

N-((2R,3R,4R,6R)-6-(((1R,3R)-3,12-dihydroxy-3-(2-hydroxyacetyl)-10-methoxy-6,11-dioxo-1,2,3,4,6,11-hexahydrotetracen-1-yl)oxy)-3-hydroxy-2-methyltetrahydro-2H-pyran-4-yl)-2-(2-hydroxy-44 methyl-2-oxobenzo[d]oxazol-3(2H)-yl)methyl)phenoxy)acetamide is:

The present disclosure further provides a genus of novel affinity-tethering moieties covalently bound to a drug moiety or to an imaging moiety, either directly or optionally via a linker moiety, to covalently link the affinity-tethering moiety to a drug substance or to an imaging moiety. Further still, the present disclosure provides a therapeutic compound comprising a tethering moiety that competes with ISO-1 ((S,R)-3-(4-hydroxyphenyl)-4,5-dihydro-5-isoxazole acetic acid methyl ester) for binding to a tautomerase site of MIF, covalently bound to a drug moiety or to an imaging moiety, optionally via a linking moiety, wherein the therapeutic compound is able to block at least 50% of the binding of ISO-1 to the tautomerase site of MIF. The dissociation constant of ISO-1 is 14.5 µM.

Further still, the present disclosure provides a therapeutic compound comprising a teathering moiety capable of binding to a tautomerase site of MIF with a dissociation constant of between 10 mM and 1 pM, and covalently bound to a drug moiety, optionally via a linking moiety. Without being bound by theory, the disclosed pharmaceutical compounds are targeted to cancer cells or immune cells via the tethering moiety, wherein the tethering moiety hitch-hikes to or into its target cell while bound to endogenous MIF.

The present disclosure provides compounds, pharmaceutical compositions and methods of treatment using a pharmaceutical composition, comprising a tethering moiety that is capable of binding to a macrophage migration inhibitory factor MIF polypeptide, optionally linked to a linker moiety and further covalently bound to a therapeutic agent or imaging agent. More specifically, the present disclosure provides a genus of tethering moieties covalently bound to pharmacologic cytotoxic agents or imaging agents, either directly or optionally via a linker moiety, to covalently link the tethering moiety to the cytotoxic agent. Without being bound by theory, the disclosed cytotoxic pharmaceutical compounds and imaging agents are targeted to preferentially gain cellular access into target cells, via the MIF tethering moiety as an express pathway to a cellular nucleus without degradation on cellular lysozymes.

The present disclosure further provides a genus of novel affinity-tethering moieties covalently bound to a drug moiety or to an imaging moiety, either directly or optionally via a linker moiety, to covalently link the affinity-tethering moiety to a drug substance or to an imaging moiety. Further still, the present disclosure provides a therapeutic compound comprising a teathering moiety that competes with ISO-1 ((S,R)-3-(4-hydroxyphenyl)-4,5-dihydro-5-isoxazole acetic acid methyl ester) for binding to a tautomerase site of MIF, covalently bound to a drug moiety or to an imaging moiety, optionally via a linking moiety, wherein the therapeutic compound is able to block at least 50% of the binding of ISO-1 to the tautomerase site of MIF.

Further still, the present disclosure provides a therapeutic compound comprising a teathering moiety that bind to the tautomerase site of MIF with a dissociation constant between 10 mM and 1 pM, covalently bound to a drug moiety, optionally via a linking moiety. The disclosed pharmaceutical compounds are specifically targeted to cancer cells or immune cells via an affinity-tethering moiety that hitch-hikes to or into its target cell while bound to endogenous MIF.

DEFINITIONS

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less then 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, n-pentyl, heptyl, nonyl, and decyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e. a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) where each R is an alkyl group having less than about 12 carbons, preferably where the R group is a lower alkyl group.

"Arylalkyl" means an aryl-alkyl-group in which the aryl and alkyl are as previously described. Preferred arylalkyls comprise a lower alkyl group. Non-limiting examples of suitable aralkyl groups include benzyl, 2-phenethyl and napthalenylmethyl. The bond to the parent moiety is through the alkyl.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the hetereoalkyl group is saturated. In another embodiment, the heteroalkyl group is unsaturated. In various embodiments, the unsaturated heterolkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl. The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect, the R group which is, or is part of the substituent attached to the heteroaryl ring is an alkyl group having less than about 12 carbons, while in another aspect the R group is a lower alkyl group.

"Heteroaralkyl" or "heteroarylalkyl" means a heteroaryl-alkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is H$_2$O.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The compounds disclosed herein form salts that are also within the scope of this disclosure. Reference to a compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by Berge et al, *J. Pharmaceutical Sciences* (1977) 66(1)1-19; Gould, *International J. Pharmaceutics* (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), arylalkyl halides (e.g., benzyl and phenethyl bromides), and others.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide, Ifosfamide, Melphalan, Chlorambucil, Pipobroman, Triethylene-melamine, Triethylenethiophos-phoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, Aminopterin, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (Taxol®), Mithramycin, Deoxycoformycin, Mitomycin-C, L-Asparaginase, Interferons (especially IFN-γ), etoposide, and Teniposide.

Hormones and steroids (including synthetic analogs): 17β-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2008 edition (Thomson P D R, Montvale, N.J. 07645-1742, 25 USA); the disclosure of which is incorporated herein by reference herein.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in this disclosure are well known to those of skilled in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (NSC 125973), thiocolchicine (NSC 361792), trityl cysteine (NSC 83265), vinblastine sulfate (NSC 49842), vincristine sulfate (NSC 67574), epothilone A, epothilone, and discodermolide (Service, (1996) *Science*, 274:2009) estramustine, nocodazole, MAP4, and the like.

Particularly, agents can be compounds with paclitaxel-like activity. These include, but are not limited to paclitaxel and paclitaxel derivatives (paclitaxel-like compounds) and analogues. Paclitaxel and its derivatives are available commercially.

Without being bound by theory, the disclosed pharmaceutical compounds are specifically targeted to cancer cells or immune cells via an affinity-tethering moiety that hitch-hikes to or into its target cell via the covalently attached tethering moiety.

Drug Moieties

The following table lists various examples of drug moieties to be covalently attached to a tethering moiety.

| DRUG Moiety |
|---|
| 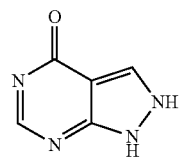 |
| Allopurinol |

-continued
| DRUG Moiety |
|---|
| 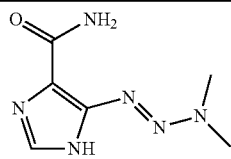<br>Dacarbazine |
| 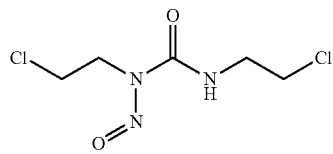 [SMILES: O=NN(CCCl)C(=O)NCCCl]<br>Carmustine |
| 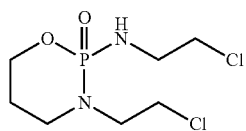 [SMILES: O=P1(NCCCl)OCCCN1CCCl]<br>Ifosfamide |
| 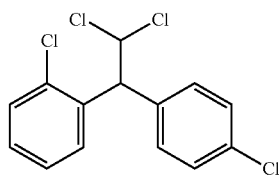 [SMILES: Clc1ccc(C(c2ccccc2Cl)C(Cl)Cl)cc1]<br>Mitotane |
| 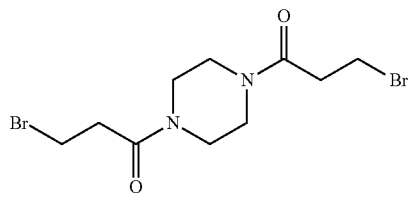 [SMILES: O=C(CCBr)N1CCN(C(=O)CCBr)CC1]<br>Pipobroman |
| 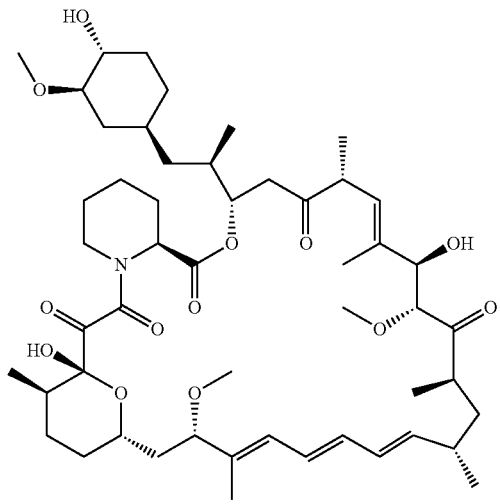 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]<br>Rapamycin |

-continued
DRUG Moiety
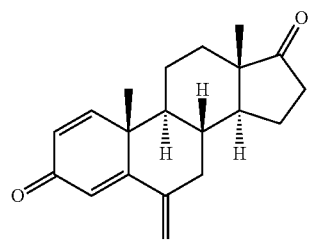
Exemestane
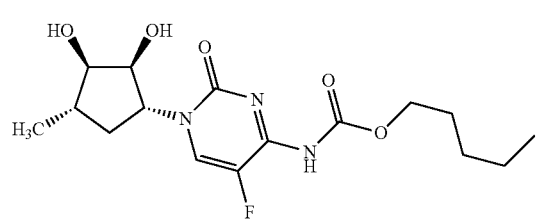 [SMILES: CCCCCOC(=O)Nc1nc(=O)n([C@@H]2C[C@H](C)[C@@H](O)[C@H]2O)cc1F]
Capecitabine
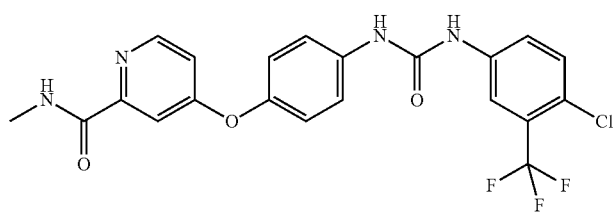 [SMILES: CNC(=O)c1cc(Oc2ccc(NC(=O)Nc3ccc(Cl)c(C(F)(F)F)c3)cc2)ccn1]
Sorafenib
Fluorouracil
Arsenic trioxide
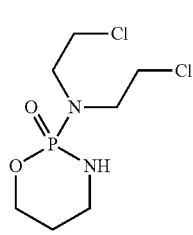 [SMILES: O=P1(N(CCCl)CCCl)NCCCO1]
Cyclophosphamide
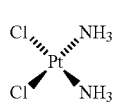
Cisplatin -continued
| DRUG Moiety |
|---|
| 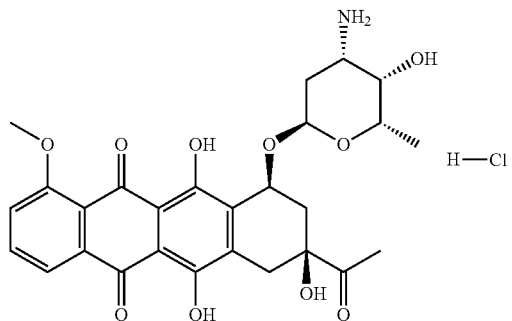
Daunorubicin HCl |
| 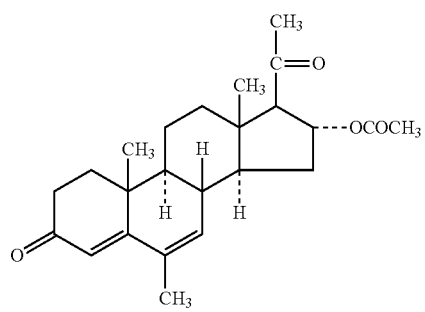
Megestrol acetate |
| 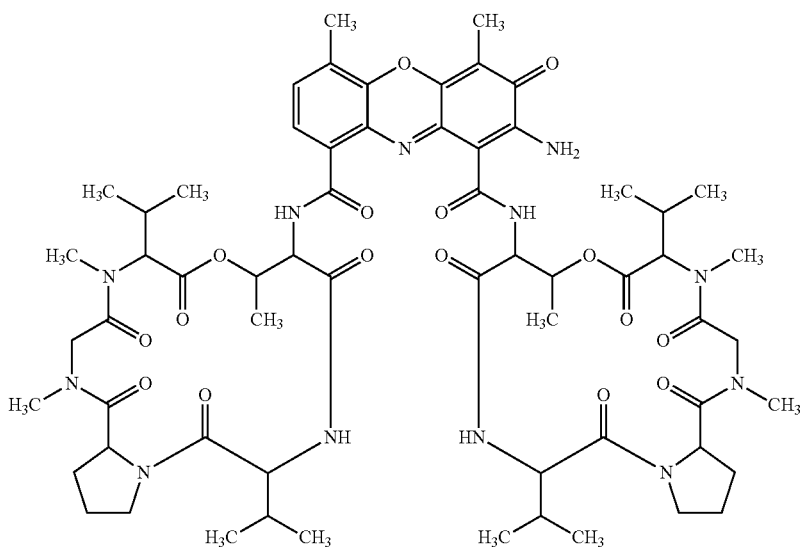
Dactinomycin |
| 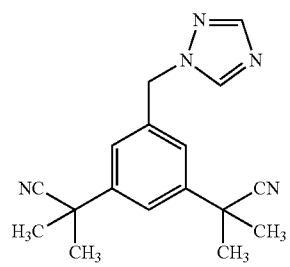
Anastrozole |

| DRUG Moiety |
|---|
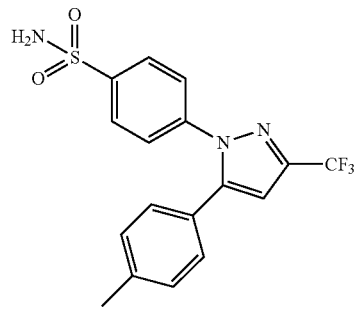 [SMILES: Cc1ccc(-c2cc(C(F)(F)F)nn2-c2ccc(S(N)(=O)=O)cc2)cc1]
Celecoxib
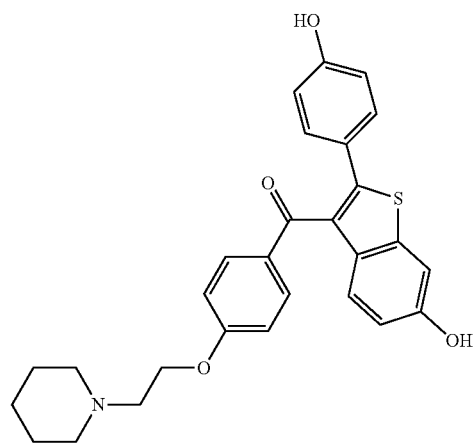 [SMILES: O=C(c1ccc(OCCN2CCCCC2)cc1)c1c(-c2ccc(O)cc2)sc2cc(O)ccc12]
Raloxifene HCl
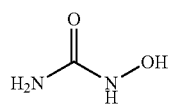
Hydroxyurea
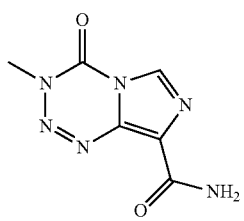
Temozolomide
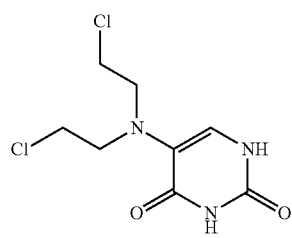 [SMILES: O=c1[nH]cc(N(CCCl)CCCl)c(=O)[nH]1]
Uracil mustard

| DRUG Moiety |
|---|
| 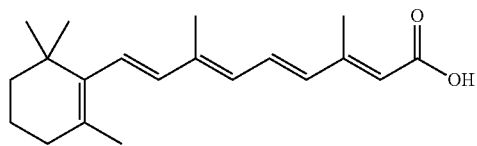 [SMILES: CC1=C(/C=C/C(C)=C/C=C/C(C)=C/C(=O)O)C(C)(C)CCC1]<br>Tretinoin |
| 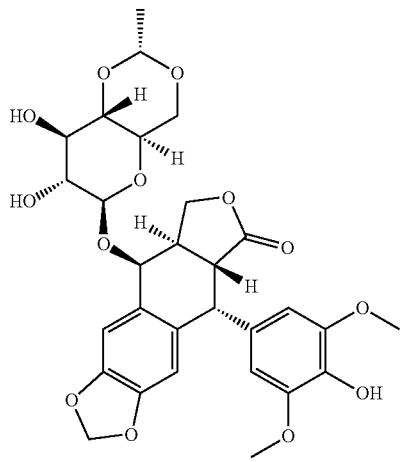<br>Etoposide |
| 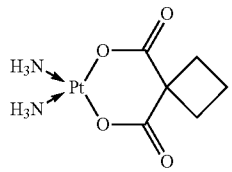<br>Carboplatin |
| 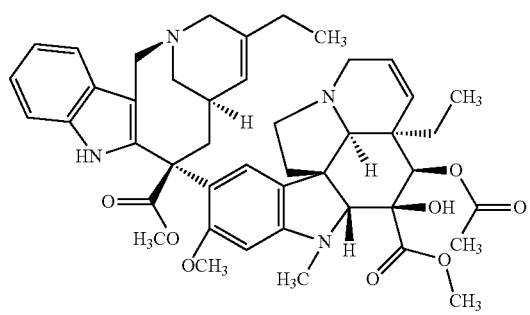<br>Vinorelbine tartrate |
| 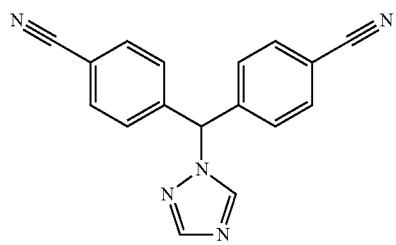 [SMILES: N#Cc1ccc(C(c2ccc(C#N)cc2)n2cncn2)cc1]<br>Letrozole |

| DRUG Moiety |
|---|
| 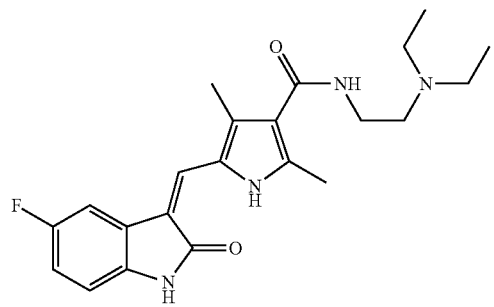 [SMILES: CCN(CC)CCNC(=O)c1c(C)[nH]c(/C=C2\C(=O)Nc3ccc(F)cc32)c1C]<br>Sunitinib |
| 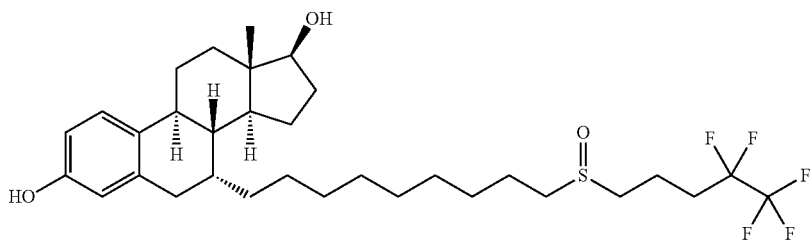<br>Fulvestrant |
| 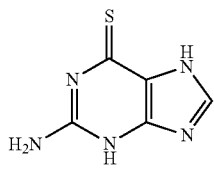 [SMILES: Nc1nc(=S)c2[nH]cnc2[nH]1]<br>Thioguanine |
| 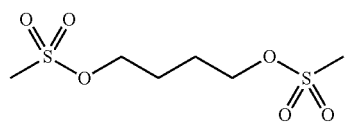<br>Busulfan |
| 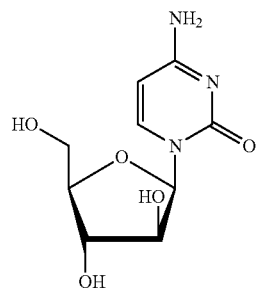<br>Cytarabine HCl |

-continued
DRUG Moiety
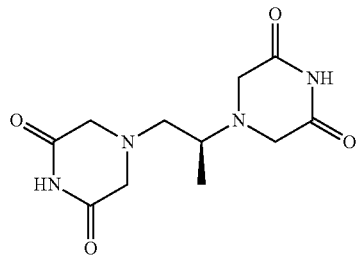 [SMILES: C[C@@H](CN1CC(=O)NC(=O)C1)N1CC(=O)NC(=O)C1]
Dexrazoxone
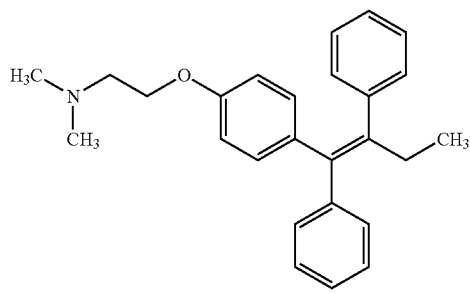 [SMILES: CC/C(=C(\c1ccccc1)c1ccc(OCCN(C)C)cc1)c1ccccc1]
Tamoxifen citrate
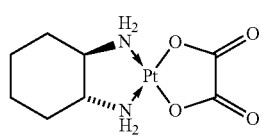
Oxaliplatin
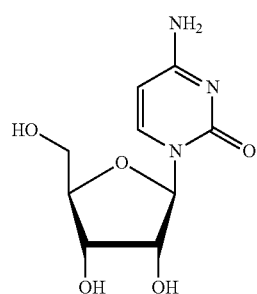
Azacitidine
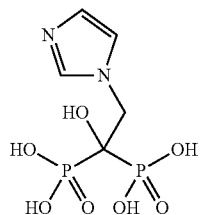 [SMILES: O=P(O)(O)C(O)(Cn1ccnc1)P(=O)(O)O]
Zolendronic acid -continued
| DRUG Moiety |
|---|
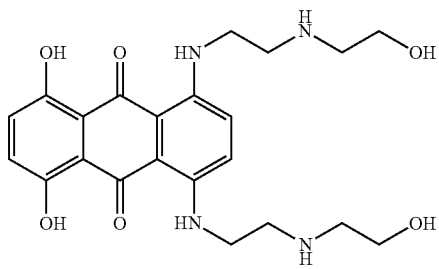 [SMILES: O=C1c2c(O)ccc(O)c2C(=O)c2c(NCCNCCO)ccc(NCCNCCO)c21]
Mitoxantrone
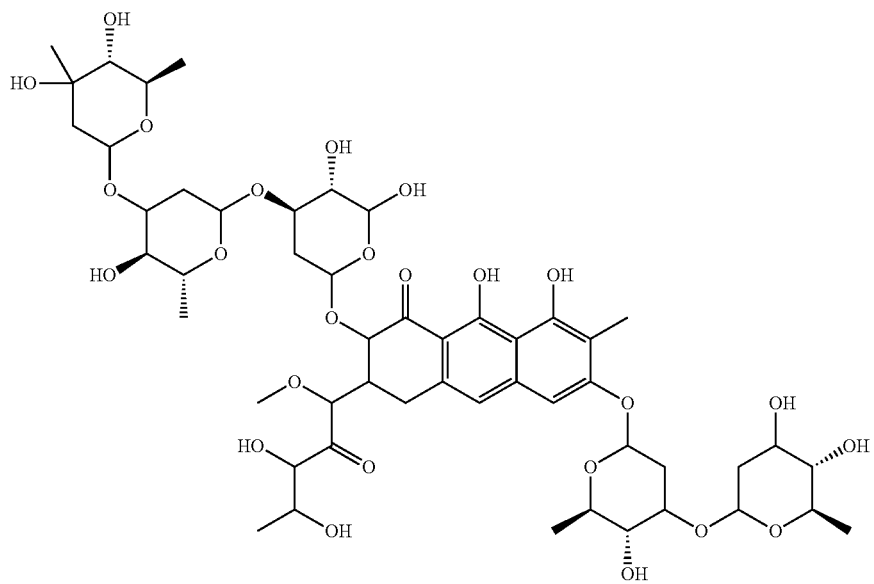 [SMILES: COC(C(=O)C(O)C(C)O)C1Cc2cc3cc(OC4CC(OC5CC(O)[C@H](O)[C@@H](C)O5)[C@H](O)[C@@H](C)O4)c(C)c(O)c3c(O)c2C(=O)C1OC1C[C@@H](OC2CC(OC3CC(C)(O)[C@H](O)[C@@H](C)O3)[C@H](O)[C@@H](C)O2)[C@H](O)C(O)O1]
Plicamycin
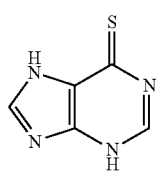
Mercaptopurine
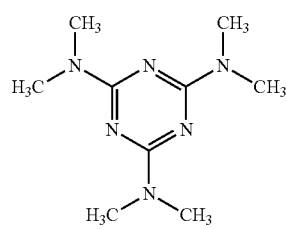
Altretamine

| DRUG Moiety |
|---|
| 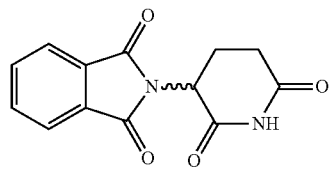 [SMILES: O=C1CCC(N2C(=O)c3ccccc3C2=O)C(=O)N1]
Thalidomide |
| 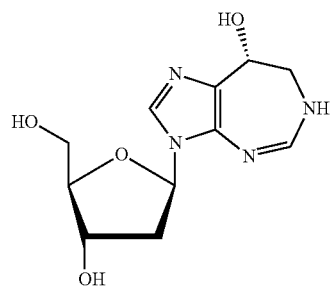 [SMILES: OC[C@H]1O[C@@H](n2cnc3c2N=CNC[C@H]3O)C[C@H]1O]
Pentostatin |
| 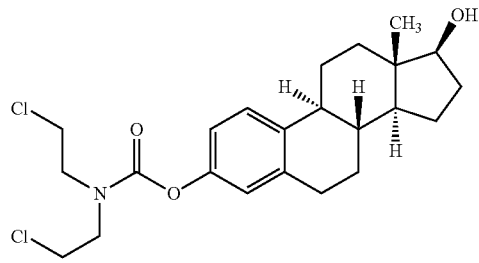
Estramustine disodium phosphate |
| 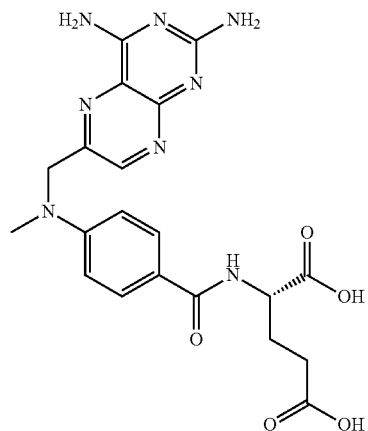 [SMILES: CN(Cc1cnc2nc(N)nc(N)c2n1)c1ccc(C(=O)N[C@@H](CCC(=O)O)C(=O)O)cc1]
Methotrexate |

-continued
| DRUG Moiety |
|---|
| 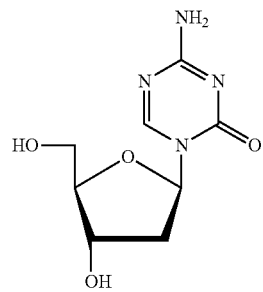 [SMILES: Nc1ncn([C@H]2C[C@@H](O)[C@@H](CO)O2)c(=O)n1]<br>Decitabine |
| 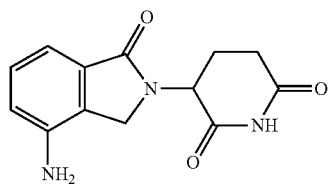 [SMILES: Nc1cccc2c1CN(C1CCC(=O)NC1=O)C2=O]<br>Lenalidomide |
| 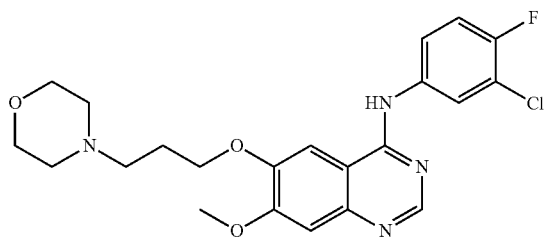 [SMILES: COc1cc2ncnc(Nc3ccc(F)c(Cl)c3)c2cc1OCCCN1CCOCC1]<br>Gefitinib |
| 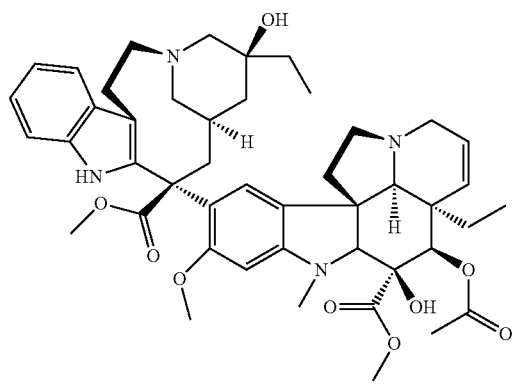<br>Vinblastine sulfate |
| 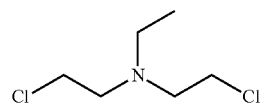<br>Nitrogen mustard |

-continued
| DRUG Moiety |
|---|
| 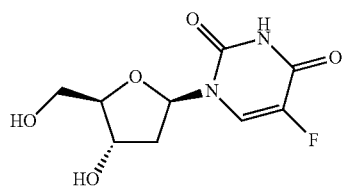 [SMILES: O=c1[nH]c(=O)n([C@H]2C[C@H](O)[C@@H](CO)O2)cc1F]<br>Floxuridine |
| 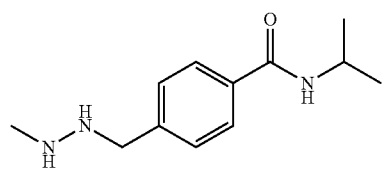 [SMILES: CNNCc1ccc(C(=O)NC(C)C)cc1]<br>Procarbazine |
| 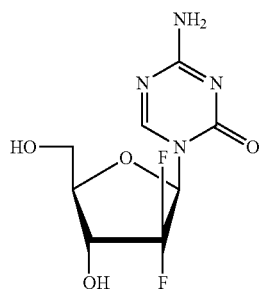 [SMILES: Nc1ncn([C@@H]2O[C@H](CO)[C@H](O)C2(F)F)c(=O)n1]<br>Gemcitabine HCl |
| 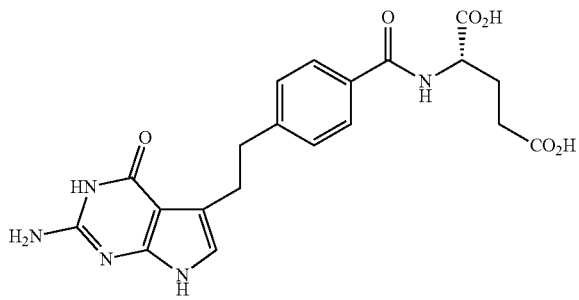 [SMILES: Nc1nc2[nH]cc(CCc3ccc(C(=O)N[C@@H](CCC(=O)O)C(=O)O)cc3)c2c(=O)[nH]1]<br>Pemetrexed |
| 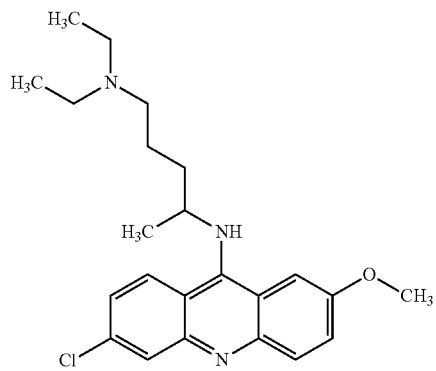 [SMILES: CCN(CC)CCCC(C)Nc1c2ccc(Cl)cc2nc2ccc(OC)cc12]<br>Acrichine |

| DRUG Moiety |
|---|
| 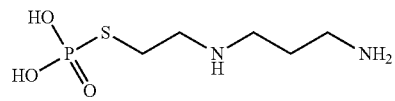 [SMILES: NCCCNCCSP(=O)(O)O]
Amifostine |
| 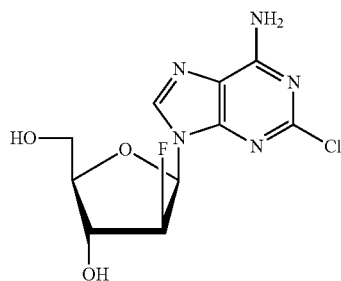
Clofarabine |
| 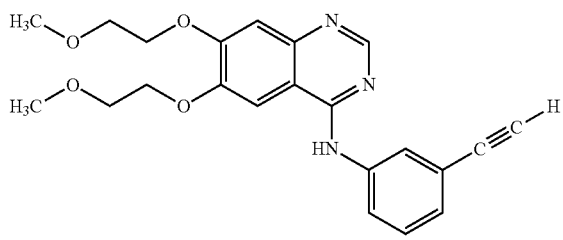 [SMILES: C#Cc1cccc(Nc2ncnc3cc(OCCOC)c(OCCOC)cc23)c1]
Erlotinib HCl |
| 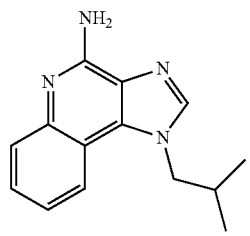 [SMILES: CC(C)Cn1cnc2c(N)nc3ccccc3c21]
Imiquimod |
| 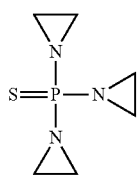 [SMILES: S=P(N1CC1)(N1CC1)N1CC1]
Thiotepa |
| 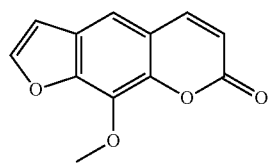 [SMILES: COc1c2occc2cc2ccc(=O)oc12]
Methoxsalen |

| DRUG Moiety |
|---|
| 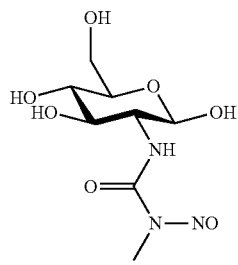
Streptozocin |
| 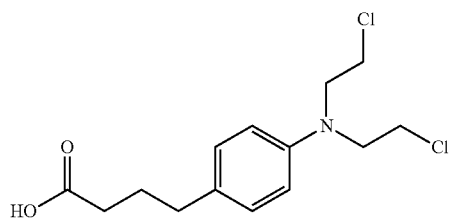 [SMILES: O=C(O)CCCc1ccc(N(CCCl)CCCl)cc1]
Chlorambucil |
| 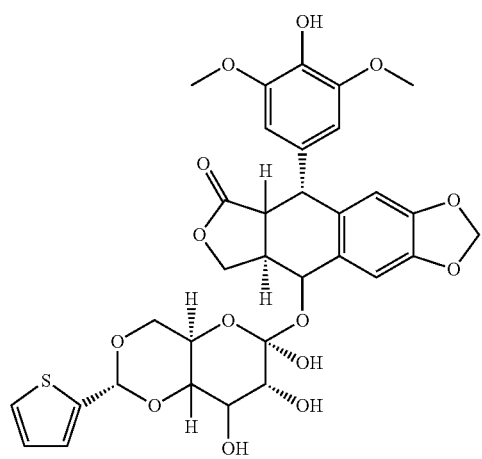 [SMILES: COc1cc([C@@H]2c3cc4c(cc3C(O[C@]3(O)O[C@@H]5CO[C@@H](c6cccs6)OC5C(O)[C@H]3O)[C@H]3COC(=O)C23)OCO4)cc(OC)c1O]
Teniposide |
| 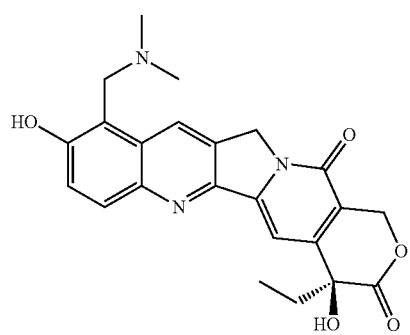 [SMILES: CC[C@@]1(O)C(=O)OCc2c1cc1n(c2=O)Cc2cc3c(CN(C)C)c(O)ccc3nc2-1]
Topotecan HCl |

| DRUG Moiety |
|---|
| 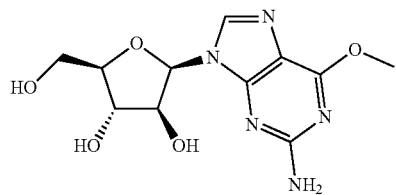 [SMILES: COc1nc(N)nc2c1ncn2[C@@H]1O[C@H](CO)[C@@H](O)[C@@H]1O]<br>Nelarabine |
| 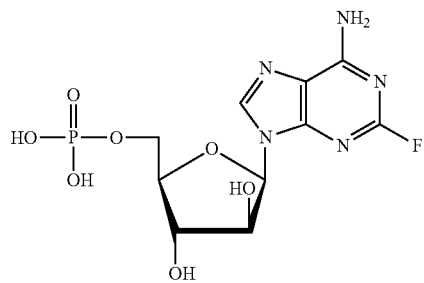<br>Fludarabine |
| 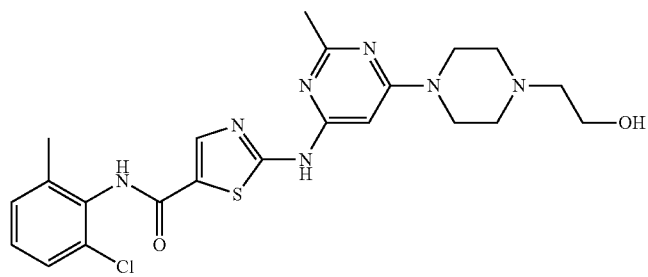 [SMILES: Cc1nc(Nc2ncc(C(=O)Nc3c(C)cccc3Cl)s2)cc(N2CCN(CCO)CC2)n1]<br>Dasatinib |
| 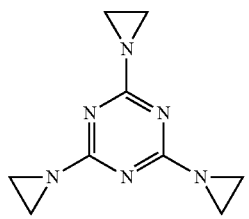 [SMILES: C1CN1c1nc(N2CC2)nc(N2CC2)n1]<br>Triethylenemelamine |
| 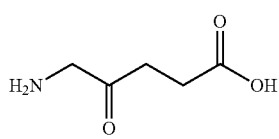<br>Aminolevulinic acid |
| 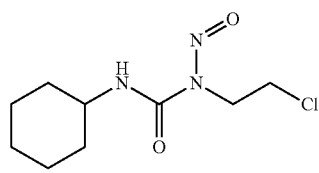 [SMILES: O=NN(CCCl)C(=O)NC1CCCCC1]<br>Lomustine, CCNU |

-continued
| DRUG Moiety |
|---|
| 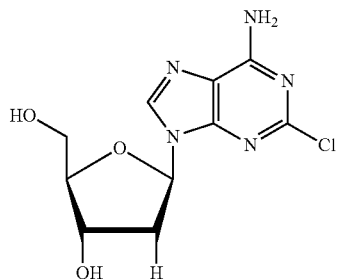 [SMILES: Nc1nc(Cl)nc2c1ncn2[C@H]1C[C@@H](O)[C@@H](CO)O1]Cladribine |
| 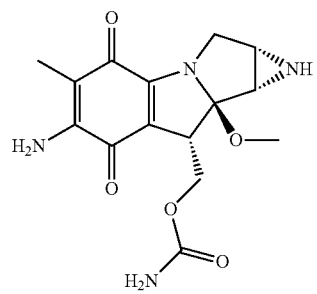 [SMILES: CO[C@@]12[C@H](COC(N)=O)C3=C(C(=O)C(C)=C(N)C3=O)N1C[C@@H]1N[C@@H]12]Mitomycin C |
| 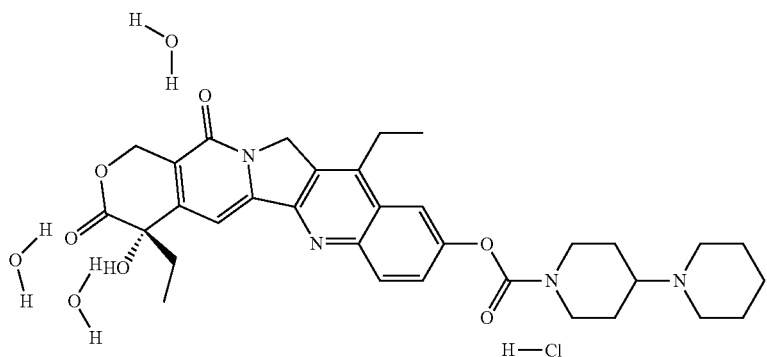Irinotecan HCl |
| 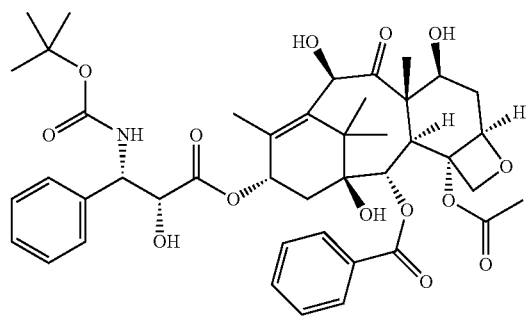Docetaxel |

| DRUG Moiety |
|---|
| 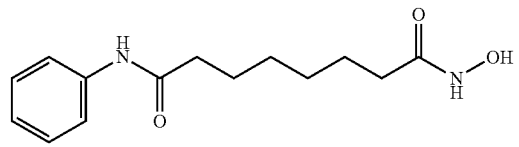 [SMILES: O=C(CCCCCCC(=O)Nc1ccccc1)NO]<br>Vorinostat |
| 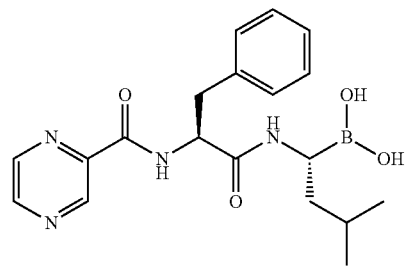 [SMILES: CC(C)C[C@H](NC(=O)[C@H](Cc1ccccc1)NC(=O)c1cnccn1)B(O)O]<br>Bortezomib |
| 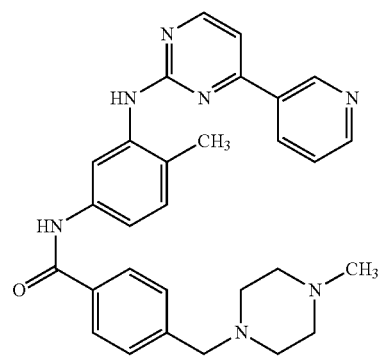 [SMILES: Cc1ccc(NC(=O)c2ccc(CN3CCN(C)CC3)cc2)cc1Nc1nccc(-c2cccnc2)n1]<br>Imatinib |
| 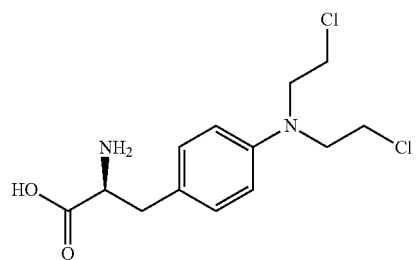 [SMILES: N[C@@H](Cc1ccc(N(CCCl)CCCl)cc1)C(=O)O]<br>Melphalan |

-continued
| DRUG Moiety |
|---|
| 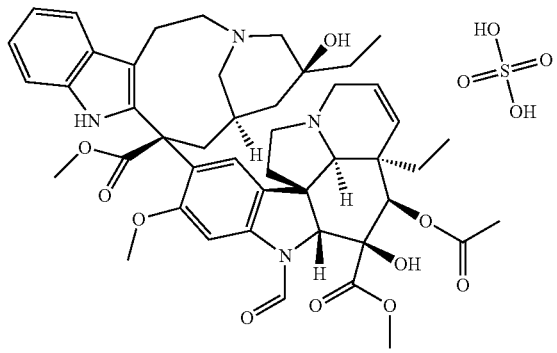
Vincristine sulfate |
| 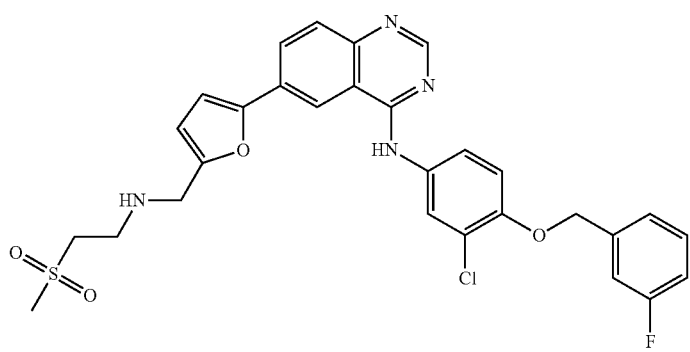 [SMILES: CS(=O)(=O)CCNCc1ccc(-c2ccc3ncnc(Nc4ccc(OCc5cccc(F)c5)c(Cl)c4)c3c2)o1]
Lapatinib |
| 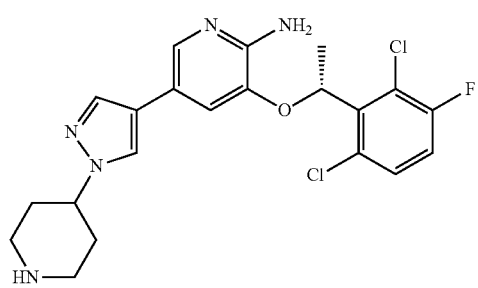 [SMILES: C[C@@H](Oc1cc(-c2cnn(C3CCNCC3)c2)cnc1N)c1c(Cl)ccc(F)c1Cl]
Crizotinib |

| DRUG Moiety |
|---|
| 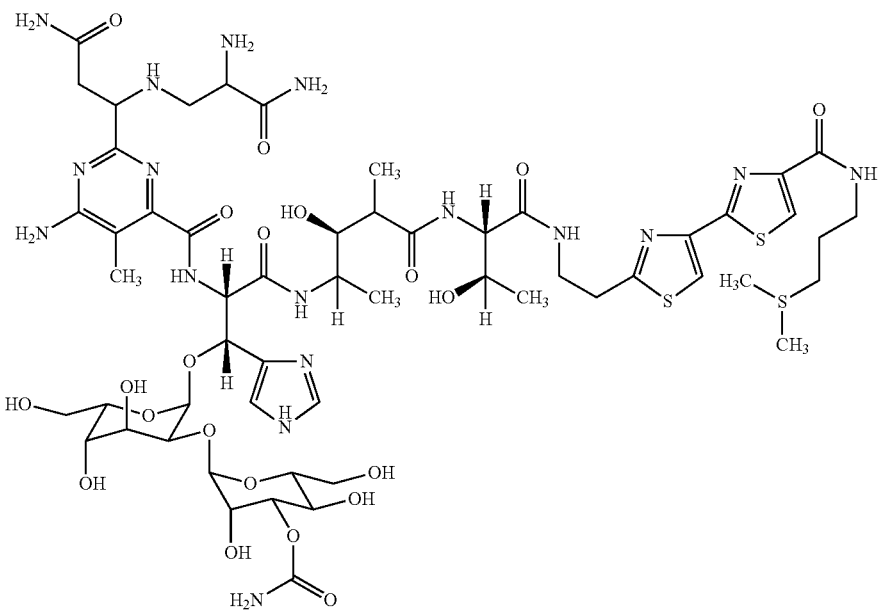
Bleomycin |
| 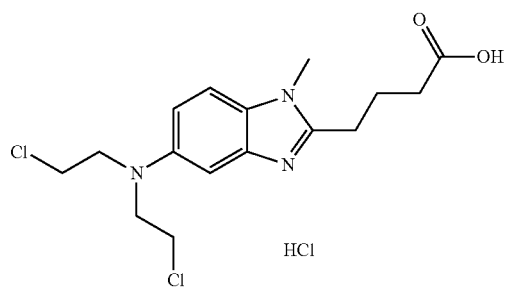 [SMILES: Cn1c(CCCC(=O)O)nc2cc(N(CCCl)CCCl)ccc21 ; Cl]
Bendamustine HCl |
| 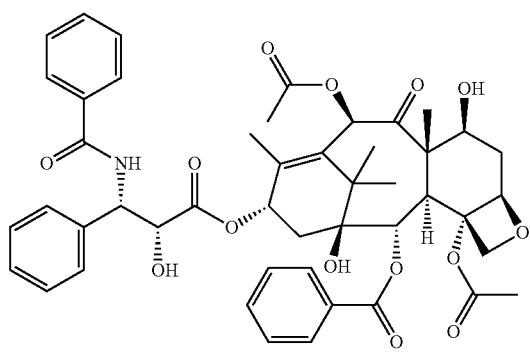 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]
Paclitaxel |

| DRUG Moiety |
|---|
| 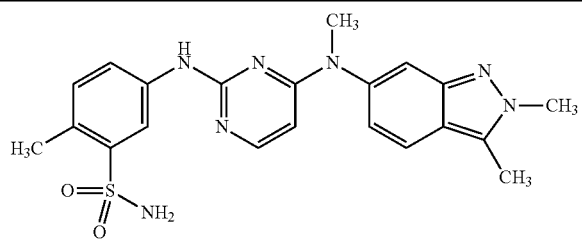
Pazopanib HCl |
| 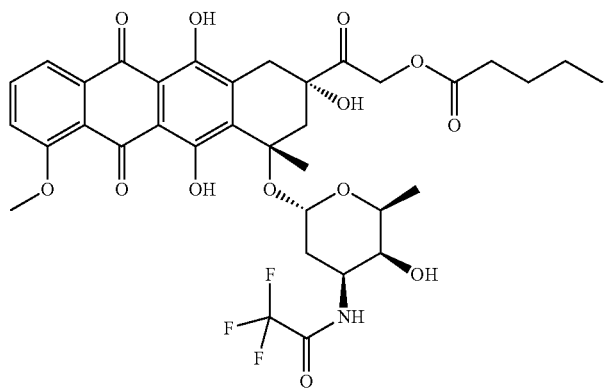 [SMILES: CCCCC(=O)OCC(=O)[C@]1(O)Cc2c(O)c3c(c(O)c2[C@@](C)(O[C@H]2C[C@H](NC(=O)C(F)(F)F)[C@H](O)[C@H](C)O2)C1)C(=O)c1c(OC)cccc1C3=O]
Valrubicin |
| 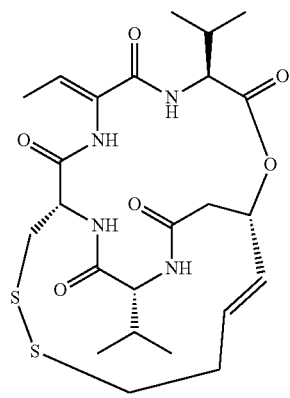 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]
Romidepsin |

| DRUG Moiety |
|---|
| 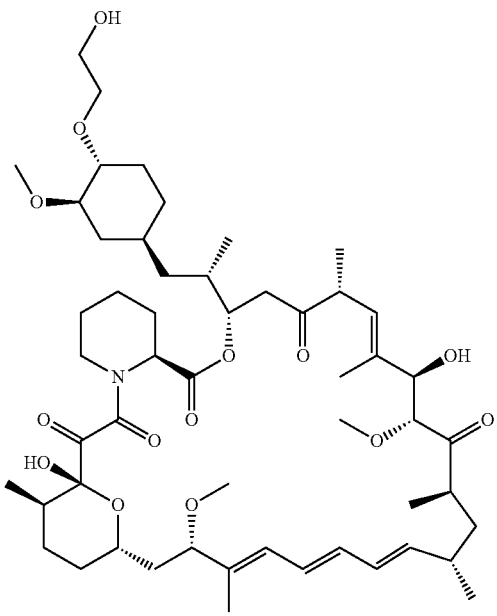 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]
Everolimus |
| 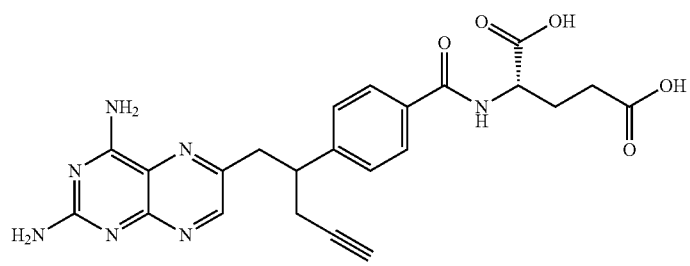 [SMILES: C#CCC(Cc1cnc2nc(N)nc(N)c2n1)c1ccc(C(=O)N[C@@H](CCC(=O)O)C(=O)O)cc1]
Pralatrexate |
| 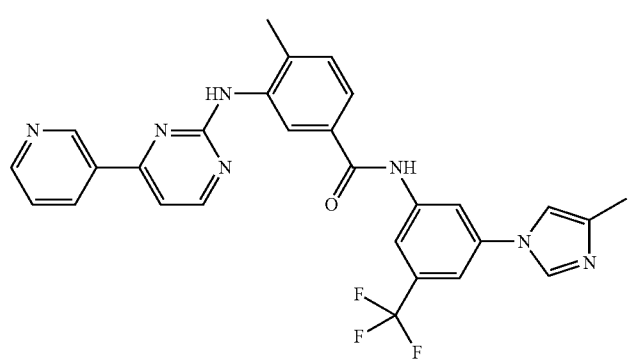 [SMILES: Cc1cn(-c2cc(NC(=O)c3ccc(C)c(Nc4nccc(-c5cccnc5)n4)c3)cc(C(F)(F)F)c2)cn1]
Nilotinib |

| DRUG Moiety |
|---|
| 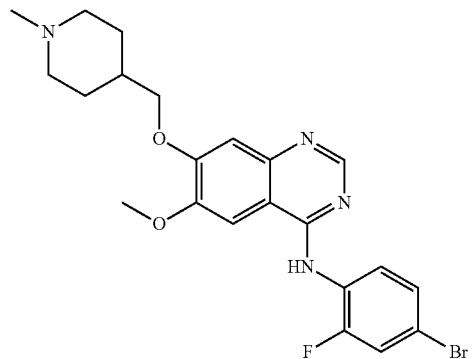 [SMILES: COc1cc2c(Nc3ccc(Br)cc3F)ncnc2cc1OCC1CCN(C)CC1]<br>Vandetanib |
| 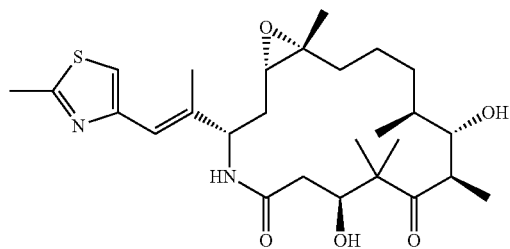 [SMILES: C/C(=C\c1csc(C)n1)[C@@H]1C[C@@H]2O[C@]2(C)CCC[C@H](C)[C@H](O)[C@@H](C)C(=O)C(C)(C)[C@@H](O)CC(=O)N1]<br>Ixabepilone |
| 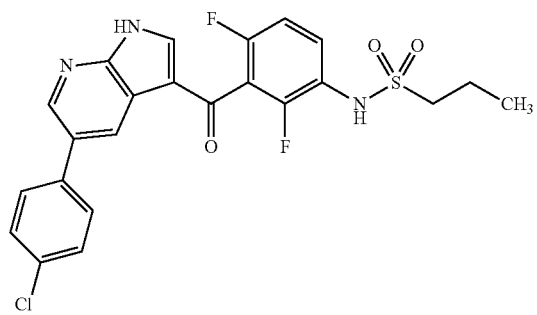 [SMILES: CCCS(=O)(=O)Nc1ccc(F)c(C(=O)c2c[nH]c3ncc(-c4ccc(Cl)cc4)cc23)c1F]<br>Vemurafenib |
| 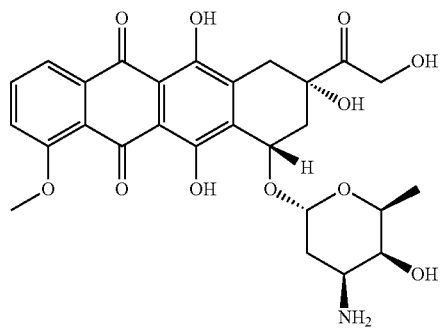 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]<br>Doxorubicin HCl |

-continued
| DRUG Moiety |
|---|
| 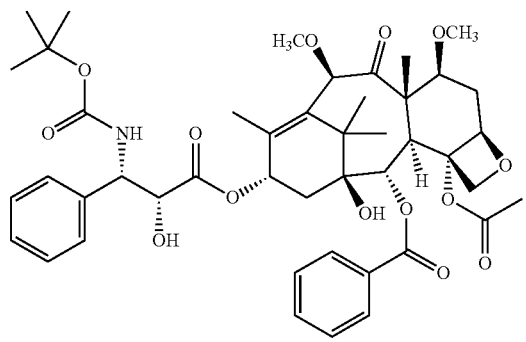 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]
Cabazitaxel |
| 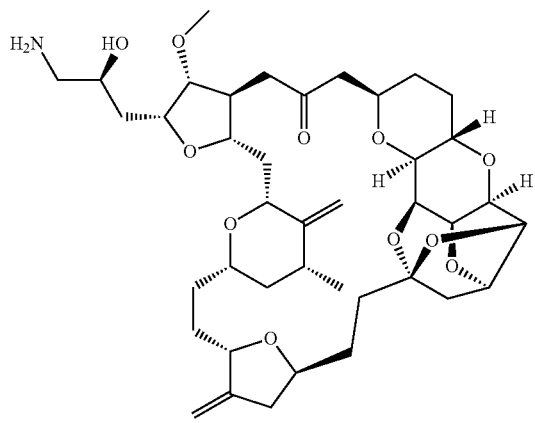 [SMILES: C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CN)O[C@H]3C[C@H]3O[C@@H](CC[C@@H]1O2)C[C@@H](C)C3=C]
Eribulin |
| 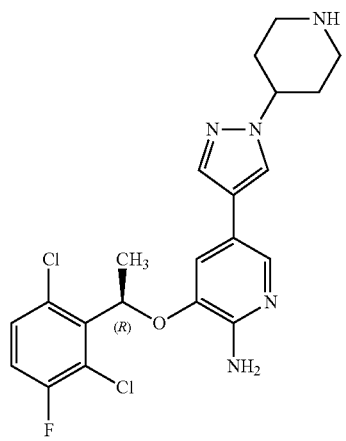
Xalkori |
| 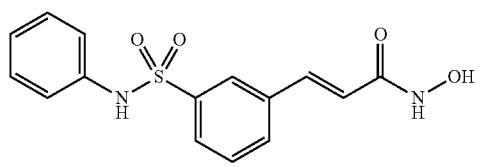 [SMILES: O=C(/C=C/c1cccc(S(=O)(=O)Nc2ccccc2)c1)NO]
abexinostat |

| DRUG Moiety |
|---|
| 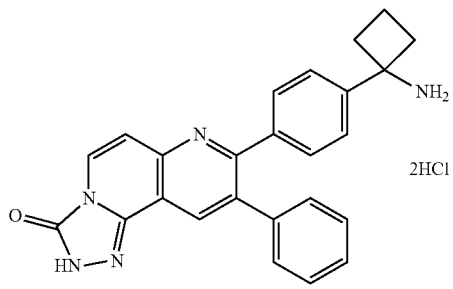 [SMILES: NC1(c2ccc(-c3nc4ccn5c(=O)[nH]nc5c4cc3-c3ccccc3)cc2)CCC1]<br>MK-2206 · 2HCl |
| 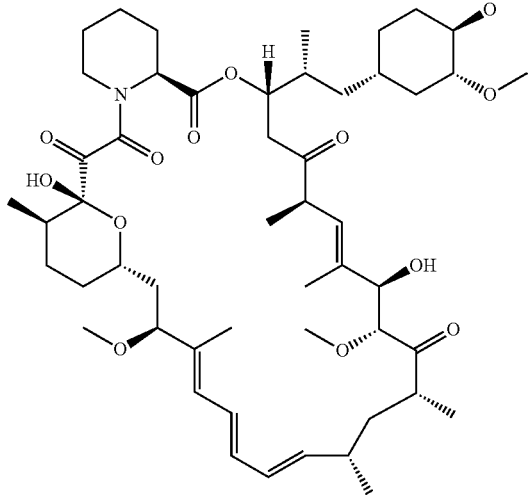<br>Temsirolimus |

In addition, instead of a cytotoxic drug moiety, there could be an imaging agent, such as a fluorophore, fluorochrome, or a chemical moiety such as a molecule, crystal, Q-dot, group or peptide that exhibits fluorescence or a chelator. Whereas the fluorophore moiety can re-emit light upon light excitation is attached to the linker moiety and/or the MIF affinity moiety. Examples include a moiety selected from the group consisting of 33(CS)2Ir(μ-Cl)2Ir(CS)2-μ-chloro-bridged dimer of iridium(III) bis(3-(benzothiazol-2-yl)-7-(diethylamino)-coumarin)), 1,1-Diethyl-4,4-carbocyanine iodide-1-ethyl-4-[3-(1-ethylquinolin-4-ylidene)prop-1-enyl]quinolin-1-ium iodide, 1,2-Diphenylacetylene-2-phenylethynylbenzene, 1,4-Diphenylbutadiene-[(1E,3E)-4-phenylbuta-1,3-dienyl]benzene, 1,4-Diphenylbutadiyne-4-phenylbuta-1,3-diynylbenzene, 1,6-Diphenylhexatriene-[(1E,3E,5E)-6-phenylhexa-1,3,5-trienyl]benzene, 1,6-Diphenylhexatriene-[(1E,3E,5E)-6-phenylhexa-1,3,5-trienyl]benzene, 1-anilinonaphthalene-8-sulfonic acid, 2,7-Dichlorofluorescein, 2-Di-1-ASP-2-[4-(Dimethylamino)styryl]-1-methylpyridinium iodide, 2-dodecylresorufin-8-dodecyl-7-hydroxyphenoxazin-3-one, 2-Methylbenzoxazole-2-Methyl-1,3-benzoxazole, 3,3-Diethylthiadicarbocyanine iodide, 4-Dimethylamino-4 Nitrostilbene, 5(6)-Carboxyfluorescein-3',6'-dihydroxy-1-oxospiro[2-benzofuran-3,9'-xanthene]-5-carboxylic acid, 5(6)-Carboxytetramethylrhodamine B, 5-(and-6)-carboxy-2',7'-dichlorofluorescein, 5-(and-6)-carboxy-2,7-dichlorofluorescein, 5-chloromethylfluorescein, 5-carboxyfluorescein, 5-carboxy-X-rhodamine, 5-carboxytetramethylrhodamine, 6,8-difluoro-7-hydroxy-4-methylcoumarin, 6-carboxyrhodamine 6G, 6-carboxy-2,4,4,5,7,7-hexachlorofluorescein succinimidyl ester, 6-carboxy-4,5-dichloro-2,7-dimethoxyfluorescein, 6-carboxy-2',4,7,7'-tetrachlorofluorescein succinimidyl ester, 7-aminoactinomycin D-2,7-diamino-4,6-dimethyl-3-oxo-1-N,9-N-bis-[(18aS)-10c,14,17-trimethyl-5,8,12,15,18-pentaoxo-6c,13t-di(propan-2-yl)-18ar-hexadecahydro-1H-pyrrolo[2,1-i][1,4,7,10,13]oxatetraazacyclohexadecin-9c-yl]-3H-phenoxazine-1,9-dicarboxamide, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline protonated, 9,10-Bis(Phenylethynyl)Anthracene, 9,10-Diphenylanthracene, Acridine orange-N,N,N',N'-tetramethylacridine-3,6-diamine hydrochloride, Acridine Yellow-2,7-dimethylacridine-3,6-diamine hydrochloride, Adams Apple Red 680, Adirondack Green 520, Alexa Fluor 350-7-amino-3-{[(2,5-dioxopyrrolidin-1-yl)oxy]-2-oxoethyl}-4-methyl-2-oxo-2H-chromene-6-sulfonic acid, Alexa Fluor 405-tris(N,N-diethylethanaminium) 8-[2-(4-{[(2,5-dioxopyrrolidin-1-yl)oxy]carbonyl}piperidin-1-yl)-2-oxoethoxy]pyrene-1,3,6-trisulfonate, Alexa Fluor 430-N,N-diethylethanaminium[9-{6-[(2,5-dioxopyrrolidin-1-yl)oxy]-6-oxohexyl}-8,8-dimethyl-2-oxo-4-(trifluoromethyl)-8,9-dihydro-2H-benzo[g]chromen-6-yl]methanesulfonate, Alexa Fluor 480-trilithium 2-(3,6-diamino-4,5-disulfonatoxanthenium-9-yl)benzene-1,4-dicarboxylate, Alexa Fluor 488-dilithium 4-carboxy-2-(3,6-diamino-4,5-disulfonatoxanthenium-9-yl)benzoate, Alexa. Fluor 488 meta-isomer 2-5-carboxy-2-(3,6-diamino-4,5-disulfonatoxanthenium-9-yl)benzoate, Alexa Fluor 488 para isomer 2-4-carboxy-2-(3,6-diamino-4,5-disulfonatoxanthenium-9-yl)benzoate, Alexa Fluor 514-6-(2-carboxy-4-{[(2,5-dioxopyrrolidin-1-yl)oxy]carbonyl}phenyl)-9-iminio-2,2,4-trimethyl-12-sulfo-1,3,4,9-tetrahydro-2H-chromeno[3,2-g]quinoline-10-sulfonate, 6-(2-carboxy-5-{[(2,5-dioxopyrrolidin-1-yl)oxy]carbonyl}phenyl)-9-iminio-2,2,4-trimethyl-12-sulfo-1,3,4,9-tetrahydro-2H-chromeno[3,2-g]quinoline-10-sulfonate, Alexa Fluor 532-5-{[2,5-dioxopyrrolidin-1-yl)oxy]carbonyl}phenyl)-2,3,3,7,7,8-hexamethyl-2,3,7,8-tetrahydro-1H-pyrano[3,2-f:5,6-f']diindole-10,12-disulfonic acid, Alexa Fluor 546-sodium 6-(2-carboxy-3,4,6-trichloro-5-{[2-({6-[(2,5-dioxopyrrolidin-1-yl)oxy]-6-oxohexyl}amino)-2-oxoethyl]thio}phenyl)-2,2,4,8,10,10-hexamethyl-3,4,5a,8,9,10,11,12a-octahydro-2H-pyrano[3,2-g:5,6-g']diquinolin-1-ium-12,14-disulfonate, Alexa Fluor 555-4-(6-amino-3-imino-4,5-disulfo-3H-xanthen-9-yl)benzene-1,3-dicarboxylic acid, Alexa Fluor 568-[1,10-dihydro-2,2,10,10-tetramethyl-4,8-bis(sulfomethyl)-2H-pyrano[3,2-g:5,6-g]diquinolin-6-yl]-Benzenedicarboxylic acid compd. with N-ethyl-N-(1-methylethyl)-2-propanamine, Alexa Fluor 594-[6-(2-carboxy-4-{[(2,5-dioxopyrrolidin-1-yl)oxy]carbonyl}phenyl)-1,2,2,10,10,11-hexamethyl-8-(sulfomethyl)-10,11-dihydro-2H-pyrano[3,2-g:5,6-g']diquinolin-1-ium-4-yl]methanesulfonate, Alexa Fluor 594 para-[6-(2-carboxy-5-[(2,5-dioxopyrrolidin-1-yl)oxy]carbonyl)phenyl)-1,2,2,10,10,11-hexamethyl-8-(sulfomethyl)-10,11-dihydro-2H-pyrano[3,2-g:5,6-g']diquinolin-1-ium-4-yl]methanesulfonate, Alexa Fluor 610, bis(N,N-diethylethanaminium) 2,3,5-trichloro-4-{[2-({6-[(2,5-dioxopyrrolidin-1-yl)oxy]-6-oxohexyl}amino)-2-oxoethyl]sulfanyl}-6-[1,2,2,10,10,11-hexamethyl-4,8-bis(sulfonatomethyl)-10,11-dihydro-2H-pyrano[3,2-g:5,6-g']diquinolin-1-ium-6-yl]benzoate, Alexa Fluor 610-X-bis(N,N-diethylethanaminium2,3,5-trichloro-4-{[2-({6-[(2,5-dioxopyrrolidin-1-yl)oxy]-6-oxohexyl}amino)-2-oxoethyl]sulfanyl}-6-[1,2,2,10,10,11-hexamethyl-4,8-bis(sulfonatomethyl)-10,11-dihydro-2H-pyrano[3,2-g:5,6-g']diquinolin-1-ium-6-yl]benzoate, Alexa Fluor 633, Alexa Fluor 635, Alexa Fluor 647-2-(((((8S,9S,10R,13S,14S,17R,E)-17-((2S,5S)-3,4-dihydroxy-5,6-dimethylheptan-2-yl)-2,3-dihydroxy-10,13-dimethylhexadecahydro-6H-cyclopenta[a]phenanthren-6-ylidene)amino)oxy)-N-propylacetamide, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin-2H-1-Benzopyran-2-one, 7-amino-4-methyl, Amplex Gold (product), Amplex Red-1-(3,7-dihydroxy-10H-phenoxazin-10-yl)-N-acetyl-3,7-dihydroxyphenoxazine, Anthracene, Allophycocyanin, AsRed2, ATTO 425-4-[3-(ethoxycarbonyl)-6,8,8-trimethyl-2-oxo-7,8-dihydro-2H-pyrano[3,2-g]quinolin-9(6H)-yl]butanoic acid, ATTO 465-3,6-diamino-10-(3-carboxypropyl)acridinium perchlorate, ATTO 488-(2,5-dioxopyrrolidin-1-yl) 4-[3,6-bis(dimethylamino)acridin-10-ium-10-yl]butanoate perchlorate, ATTO 495-10-(3-carboxypropyl)-3,6-bis(dimethylamino)acridinium perchlorate, ATTO 520-[9-(2-carboxyethyl)-6-(ethylamino)-2,7-dimethylxanthen-3-ylidene]-ethylazanium perchlorate, ATTO 550, ATTO 565-6-(2,4-dicarboxyphenyl)-1,11-diethyl-3,4,8,9,10,11-hexahydro-2H-pyrano[3,2-g:5,6-g']diquinolin-1-ium perchlorate, ATTO 590-6-(2,4-dicarboxyphenyl)-1,11-diethyl-2,2,4,8,10,10-hexamethyl-10,11-dihydro-2H-pyrano[3,2-g:5,6-g']diquinolin-1-ium perchlorate, ATTO 610-4-[9-(dimethylamino)-11,11-dimethyl-3,4-dihydro-2H-naphtho[3,2-g]quinolin-1-ium-1-yl]butanoic acid perchlorate, ATTO 620, ATTO 633, ATTO 635-4-[9-(dimethylamino)-2,2,4,11,11-pentamethylnaphtho[3,2-g]quinolin-1-ium-1-yl]butanoic acid; 2,2,2-trifluoroacetate, ATTO 647, ATTO 647N, ATTO 655-(1-(3-carboxypropyl)-11-ethyl-2,2-dimethyl-1,2,3,4,8,9,10,11-octahydrodipyrido[3,2-b:2',3'-i]phenoxazin-13-ium-4-yl)methanesulfonate, ATTO 680, ATTO 700, Auramine O-4-[4-(dimethylamino)benzenecarboximidoyl]-N,N-dimethylaniline hydrochloride, Azami Green, Azami Green monomeric, BCECF-2',7'-bis-(2-carboxyethyl)-5-(and-6)-carboxyfluorescein, Benzene, Bex1, Biphenyl, Birch Yellow 580, BOBO-1-2,2'-{propane-1,3-diylbis[(dimethylazaniumdiyl)propane-3,1-diylpyridin-1-yl-4-ylidenemethylylidene]}bis(3-methyl-1,3-benzothiazol-3-ium)tetraiodide, BOBO-3-2,2'-{propane-1,3-diylbis[(dimethylazaniumdiyl)propane-3,1-diylpyridin-1-yl-4-ylideneprop-1-en-1-yl-3-ylidene]}bis(3-methyl-1,3-benzothiazol-3-ium)tetraiodide, BODIPY 630 650-X—(N-{6-[(2,5-dioxopyrrolidin-1-yl)oxy]-6-oxohexyl}-2-(4-[2-(2-{[5-(thiophen-2-yl)-1H-pyrrol-2-yl-κN]methylene-2H-pyrrol-5-yl-κN)ethenyl]phenoxy}acetamidato)(difluoro)boron, BODIPY 650/665-(2-[4-(2-{2-[(1H,1'H-2,2'-bipyrrol-5-yl-κN~1~)methylene]-2H-pyrrol-5-yl-κN}ethenyl)phenoxy]-N-{6-[(2,5-dioxopyrrolidin-1-yl)oxy]-6-oxohexyl}acetamidato)(difluoro)boron, BODIPY FL-(3-{5-[(3,5-dimethyl-2H-pyrrol-2-ylidene-κN)methyl]-1H-pyrrol-2-yl-κN}propanoato)(difluoro)boron, BODIPY R6G-(3-{5-[(5-phenyl-2H-pyrrol-2-ylidene-κN)methyl]-1H-pyrrol-2-yl-κN}propanoato)(difluoro)boron, BODIPY TMR-X-[N-{6-[(2,5-dioxopyrrolidin-1-yl)oxy]-6-oxohexyl}-3-(2-{[5-(4-methoxyphenyl)-1H-pyrrol-2-yl-κN]methylene}-3,5-dimethyl-1H-pyrrol-4-yl-κN)propanamidato](difluoro)boron, BODIPY TR-X—(N-{6-[(2,5-dioxopyrrolidin-1-yl)oxy]-6-oxohexyl}-2-[4-(2-{[5-(thiophen-2-yl)-1H-pyrrol-2-yl-κN]methylene}-2H-pyrrol-5-yl-κN)phenoxy]acetamidato)(difluoro)boron, BODIPY TR-difluoro{methyl [4-(2-{[5-(thiophen-2-yl)-1H-pyrrol-2-yl-κN]methylene}-2H-pyrrol-5-yl-κN)phenoxy]acetatato}boron.
C-Phycocyanin, C3-Indocyanine-1-ethyl-2-[3-(1-ethyl-3,3-dimethyl-1,3-dihydro-2H-indol-2-ylidene)prop-1-en-1-yl]-3,3-dimethyl-3H-indolium iodide. C3-Oxacyanine-3-ethyl-2-[3-(3-ethyl-1,3-benzoxazol-2(3H)-ylidene)prop-1-en-1-yl]-1,3-benzoxazol-3-ium iodide, C3-Thiacyanine-3-ethyl-2-[3-(3-ethyl-1,3-benzothiazol-2(3H)-ylidene)prop-1-en-1-yl]-1,3-benzothiazol-3-ium iodide, C5-Indocyanine-1-ethyl-2-[5-(1-ethyl-3,3-dimenthyl-1,3-dihydro-2H-indol-2-ylidene)penta-1,3-dien-1-yl]-3,3-dimethyl-3H-indolium iodide, C5-Oxacyanine-3-ethyl-2-[5-(3-ethyl-1,3-benzoxazol-2(3H)-ylidene)penta-1,3-dien-1-yl]-1,3-benzoxazol-3-ium iodide, C545T-10-(1,3-benzothiazol-2-yl)-1,1,7,7-tetramethyl-2,3,6,7-tetrahydro-1H,5H,11H-pyrano[2,3-f]pyrido[3,2,1-ij]quinolin-11-one, C7-Indocyanine-1-ethyl-2-[7-(1-ethyl-3,3-dimethyl-1,3-dihydro-2H-indol-2-ylidene)hepta-1,3,5-trien-1-yl]-3,3-dimethyl-3H-indolium iodide, C7-Oxacyanine-3-ethyl-2-[7-(3-ethyl-1,3-benzoxazol-2

(3H)-ylidene)hepta-1,3,5-trien-1-yl]-1,3-benzoxazol-3-ium iodide, Calcein red-orange-[(acetyloxy)methyl $N^2,N^2$-bis{2-[(acetyloxy)methoxy]-2-oxoethyl}-N*-(3-{2-[(1H, 1'H-2,2'-bipyrrol-5-yl-κ$N^1$)methylidene]-2H-pyrrol-5-yl-κN}propanoyl)lysinatato](difluoro)boron, Calcium Crimson-5-{[4-(bis {2-[(acetyloxy)methoxy]-2-oxoethyl}amino)-3-{2-[2-(bis{2-[(acetyloxy)methoxy]-2-oxoethyl}amino)phenoxy]ethoxy}phenyl]sulfamoyl}-2-(2,3,6,7,12,13,16,17-octahydro-1H,5H, 11H,15H-pyrido[3,2,1-ij]quinolizino[1',9':6,7,8]chromeno[2,3-f]quinolin-4-ium-9-yl)benzenesulfonate, Calcium Green-1-hexapotassium [{2-[2-(2-[bis(carboxylatomethyl)amino]-5-{[(2',7'-dichloro-3',6'-dioxido-3-oxo-3H-spiro[2-benzofuran-1,9'-xanthen]-5-yl)carbonyl]amino}phenoxy)ethoxy]phenyl}(carboxylatomethyl)amino]acetate, Calcium Orange-5-({[4-(bis{2-[(acetyloxy)methoxy]-2-oxoethyl}amino)-3-{2-[2-(bis{2-[(acetyloxy)methoxy]-2-oxoethyl}amino)phenoxy]ethoxy}phenyl]carbamothioyl}amino)-2-[6-(dimethylamino)-3-(dimethyliminio)-3H-xanthen-9-yl]benzoate, Calcofluor white 2MR-, Carboxynaphthofluorescein-4-(11-hydroxy-3-oxo-3H-dibenzo[c,h]xanthen-7-yl)benzene-1,3-dicarboxylic acid or 2-(11-hydroxy-3-oxo-3H-dibenzo[c,h]xanthen-7-yl)benzene-1,4-dicarboxylic acid. Cascade Blue-N-(4-{[4-(diethylamino)phenyl][4-(ethylamino)-2-naphthyl]methylene}cyclohexa-2,5-dien-1-ylidene)-N-ethylethanaminium, Cascade Yellow-5-{2-[1-(3-{[(2,5-dioxopyrrolidin-1-yl)oxy]carbonyl}benzyl)pyridinium-4-yl]-1,3-oxazol-5-yl}-2-methoxybenzenesulfonate, Catskill Green 540=Qdot. CBQCA-3-(4-Carboxybenzoyl)quinoline-2-carboxaldehyde, CFP (Campbell Tsien 2003) Fluorescent Protein, Chlorophyll A-[(2E,7R,11R)-3,7,11,15-tetramethylhexadec-2-en-1-yl($2^2$R, 17S, 18S)-7-ethyl-$2^1,2^2$,17,18-tetrahydro-$2^2$-(methoxycarbonyl)-3,8,13,17-tetramethyl-$2^1$-oxo-12-ethenylcyclopenta[at]porphyrin-18-propanoato(2−)]magnesium, Chlorophyll B-[methyl(3S,4S)-9-ethenyl-14-ethyl-13-formyl-4,8,18-trimethyl-20-oxo-3-(3-oxo-3-{[(2E,7R,11R)-3,7,11,15-tetramethylhexadec-2-en-1-yl]oxy}propyl)phorbine-21-carboxylatato(3−)-κ$N^{23}$,κ$N^{24}$,κ$N^{25}$,κ$N^{26}$]magnesate(1−), CHOxAsH-4,5-Bis(1,3,2-dithiarsolan-2-yl)-2,8-dichloro-3,6-dihydroxy-9Hxanthen-9-one, Chromeo 488, Chromeo 494, Chromeo 505, Chromeo 546, Chromeo 642, Citrine (Campbell Tsien 2003), Coumarin 1, Coumarin 30-7-(diethylamino)-4-(1-methyl-1H-benzimidazol-2-yl)-2H-chromen-2-one, Coumarin 120-7-amino-4-methyl-2H-chromen-2-one, Coumarin 314, Coumarin 334, Coumarin 343-11-oxo-2,3,6,7-tetrahydro-1H,5H,11H-pyrano[2,3-f]pyrido[3,2,1-ij]quinoline-10-carboxylic acid, Coumarin 6, Coumarine 545T-10-(1,3-benzothiazol-2-yl)-1,1,7,7-tetramethyl-2,3,6,7-tetrahydro-1H,5H, 11H-pyrano[2,3-f]pyrido[3,2,1-ij]quinolin-11-one, Cresyl Violet Perchlorate-5,9-diaminobenzo[a]phenoxazin-7-ium perchlorate, CryptoLight, Cumarin 153, Cy2-3-(6-carboxyhexyl)-2-(3-[3-(5-carboxypentyl)-6-sulfo-1,3-benzoxazol-3-ium-2-yl]prop-2-en-1-ylidene)-2,3-dihydro-1,3-benzoxazole-6-sulfonate, Cy3-1-{6-[(2,5-dioxopyrrolidin-1-yl)oxy]-6-oxohexyl}-2-[3-(1-ethyl-3,3-dimethyl-5-sulfonato-1,3-dihydro-2H-indol-2-ylidene) prop-1-en-1-yl]-3,3-dimethyl-3H-indolium-5-sulfonate, Cy3.5-2-((1E,3E)-3-(1,1-dimethyl-1,3-dihydro-2H-benzo[e]indol-2-ylidene)prop-1-en-1-yl)-1,1-dimethyl-1H-benzo[e]indole, Cy3B-14-{2-[(2,5-dioxopyrrolidin-1-yl)oxy]-2-oxoethyl}-16,16,18-tetramethyl-6,7,7a,8a,9,10,16,18-octahydrobenzo[2'',3'']indolizino[8'',7'':5',6]pyrano[3',2':3,4]pyrido[1,2-a]indol-5-ium-2-sulfonate, Cy5-2-((1E,3Z)-5-((E)-indolin-2-ylidene)penta-1,3-dien-1-yl)-3H-indol-1-ium, Cy5.5-2-((1E,3Z,5Z)-5-(1,1-dimethyl-1,3-dihydro-2H-benzo[e]indol-2-ylidene)penta-1,3-dien-1-yl)-1,1-dimethyl-1H-benzo[e]indole. Cy7-2-{7-[1-(5-carboxypentyl)-5-sulfo-1,3-dihydro-2H-indol-2-ylidene]hepta-1,3,5-trien-1-yl}-1-ethyl-3H-indolium-5-sulfonate or 1-(5-carboxypentyl)-2-[7-(1-ethyl-5-sulfo-1,3-dihydro-2H-indol-2-ylidene)hepta-1,3,5-trien-1-yl]-3H-indolium-5-sulfonate, CypHer5-6-{2-[5-(3,3-dimethyl-5-sulfo-3H-indol-2-yl)penta-2,4-dien-1-ylidene]-3,3-dimethyl-5-sulfo-2,3-dihydro-1H-indol-1-yl}hexanoic acid, CyQUANT GR, Dabcyl SE-1-[(4-{[4-(dimethylamino)phenyl]diazenyl benzoyl)oxy]pyrrolidine-2,5-dione, DAF-FM-4-amino-5-methylamino-2-difluorofluorescein, dansyl cadaverine-1-Naphthalenesulfonamide, DAPI-2-(4-carbamimidoylphenyl)-1H-indole-6-carboximidamide, Dapoxyl(2-aminoethyl) sulfonamide, DCM-4-dicyanomethylene-2-methyl-6-(4-dimethylaminostyryl)-4H-pyrane, DDAO-1,3-dichloro-7-hydroxy-9,9-dimethyl-2(9H)-Acridinone, Deep Purple-(3S,11S)-6-[(1Z,4E,6E,8E)-1-hydroxy-3-oxodeca-1,4,6,8-tetraen-1-yl]-11-(hydroxymethyl)-3-methyl-4,12-dioxatricyclo[7.4.0.0ˆ{3,7}]trideca-1(13),6,8-triene-2,5-dione, di-8-ANEPPS-3-(4-(2-[5-(dioctylamino)-1-naphthyl]vinyl}pyridinium-1-yl)propane-1-sulfonate, DiA-4-(4-(dihexadecylamino)styryl)-N-methylpyridinium iodide, Dichlorotris(1,10-phenanthroline)ruthenium(II)-Tris(1,10-phenanthroline)ruthenium(II) chloride Hydrate, DiD-2-[3-(3,3-dimethyl-1-octadecyl-1,3-dihydro-2H-indol-2-ylidene) prop-1-en-1-yl]-3,3-dimethyl-1-octadecyl-3H-indolium perchlorate, DiICl 8(3)-2-[7-(3,3-dimethyl-1-octadecyl-1,3-dihydro-2H-indol-2-ylidene)hepta-1,3,5-trien-1-yl]-3,3-dimethyl-1-octadecyl-3H-indolium iodide, DiO-3-octadecyl-2-[3-(3-octadecyl-1,3-benzoxazol-2(3H)-ylidene)prop-1-en-1-yl]-1,3-benzoxazol-3-ium perchlorate, DiR-1,1-dioctadecyl-3,3,3,3-tetramethylindotricarbocyanine iodide, Diversa Cyan-FP, Diversa Green-FP, DOCI-3-ethyl-2-[3-(3-ethyl-2(3H)-benzoxazolylidene)-1-propen-1-yl]-, iodide Benzoxazolium, Doxorubicin-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-, (8S,10S)-5,12-Naphthacenedione, Dragon Green, DRAQ5, DsRed-protein, DsRed, DsRed Dimer2 (Campbell Tsien 2003), DsRed-Express T1. DY-480XL-1-(5-carboxypentyl)-6-2-[7-(diethylamino)-2-oxo-2H-chromen-3-yl]ethenyl)pyridinium-3-sulfonate, DY-485XL-3-(4-{7-[(5-carboxypentyl)(ethyl)amino]-2-oxo-2H-chromen-3-yl}pyridinium-1-yl)propane-1-sulfonate, DY-490XL MegaStokes, DY-500XL MegaStokes, DY-520XL-3-(4-(7-[(5-carboxypentyl)(ethyl)amino]-2-oxo-2H-chromen-3-yl pyridinium-1-yl)propane-1-sulfonate, DY-554, DY-555, DY-590, DY-590, DY-615-2-[3-(7-amino-2-tert-butyl-4H-chromen-4-ylidene)prop-1-en-1-yl]-1-(5-carboxypentyl)-3,3-dimethyl-3H-indolium-5-sulfonate, DY-630-2-{3-[2-tert-butyl-7-(diethylamino)-4H-chromen-4-ylidene]prop-1-en-1-yl}-1-(5-carboxypentyl)-3,3-dimethyl-3H-indolium-5-sulfonate, DY-631-sodium 2-{3-[2-tert-butyl-7-(diethylamino)chromenium-4-yl]prop-2-en-1-ylidene}-3-(3-carboxypropyl)-3-methyl-1-(3-sulfonatopropyl)indoline-5-sulfonate, DY-633-sodium 2-(3-{2-tert-butyl-7-[ethyl(3-sulfonatopropyl)amino] chromenium-4-yl}prop-2-en-1-ylidene)-1-(5-carboxypentyl)-3,3-dimethylindoline-5-sulfonate, DY-635-2-[3-(11-tert-butyl-2,3,6,7-tetrahydro-1H,5H-pyrano[2,3-f]pyrido[3,2,1-ij]quinolin-12-ium-9-yl)prop-2-en-1-ylidene]-1-(5-carboxypentyl)-3,3-dimethylindoline-5-sulfonate, DY-636-sodium 2-[3-(11-tert-butyl-2,3,6,7-tetrahydro-1H,5H-pyrano[2,3-f]pyrido[3,2,1-ij]quinolin-12-ium-9-yl)prop-2-en-1-ylidene]-3-(3-carboxypropyl)-3-methyl-1-(3-sulfonatopropyl)indoline-5-sulfonate, DY-647, DY-650-2-[3-(2-tert-butyl-9-ethyl-6,8,8-trimethyl-8,9-dihydropyrano

[3,2-g]quinolin-1-ium-4-yl)prop-2-en-1-ylidene]-1-(5-carboxypentyl)-3,3-dimethylindoline-5-sulfonate, DY-651-sodium 2-[3-(2-tert-butyl-9-ethyl-6,8,8-trimethyl-8,9-dihydropyrano[3,2-g]quinolin-1-ium-4-yl)prop-2-en-1-ylidene]-3-(3-carboxypropyl)-3-methyl-1-(3-sulfonatopropyl)indoline-5-sulfonate, DY-656, DY-673, DY-675-1-(5-carboxypentyl)-2-[3-(9-ethyl-6,8,8-trimethyl-2-phenyl-8,9-dihydropyrano[3,2-g]quinolin-1-ium-4-yl)prop-2-en-1-ylidene]-3,3-dimethylindoline-5-sulfonate, DY-676-sodium 3-(3-carboxypropyl)-2-[3-(9-ethyl-6,8,8-timethyl-2-phenyl-8,9-dihydropyrano[3,2-g]quinolin-1-ium-4-yl)prop-2-en-1-ylidene]-3-methyl-1-(3-sulfonatopropyl)indoline-5-sulfonate, DY-680-2-{3-[4-tert-butyl-7-(diethylamino)-2H-chromen-2-ylidene]prop-1-en-1-yl}-1-(5-carboxypentyl)-3,3-dimethyl-3H-indolium-5-sulfonate, DY-681-sodium 2-{3-[4-tert-butyl-7-(diethylamino)-2H-chromen-2-ylidene]prop-1-en-1-yl}-3-(3-carboxypropyl)-3-methyl-1-(3-sulfonatopropyl)-3H-indolium-5-sulfonate, DY-700-1-(5-carboxypentyl)-2-{3-[7-(diethylamino)-3-methyl-4-phenyl-2H-chromen-2-ylidene]prop-1-en-1-yl}-3,3-dimethyl-3H-indolium-5-sulfonate, DY-701-sodium 3-(3-carboxypropyl)-2-{3-[7-(diethylamino)-3-methyl-4-phenyl-2H-chromen-2-ylidene]prop-1-en-1-yl}-3-methyl-1-(3-sulfonatopropyl)-3H-indolium-5-sulfonate, DY-730-2-{5-[2-tert-butyl-7-(diethylamino)-4H-chromen-4-ylidene]penta-1,3-dien-1-yl}-1-(5-carboxypentyl)-3,3-dimethyl-3H-indolium-5-sulfonate, DY-731-sodium 2-{5-[2-tert-butyl-7-(diethylamino)-4H-chromen-4-ylidene]penta-1,3-dien-1-yl}-3-(3-carboxypropyl)-3-methyl-1-(3-sulfonatopropyl)-3H-indolium-5-sulfonate, DY-750-2-[5-(2-tert-butyl-9-ethyl-6,8,8-timethyl-8,9-dihydropyrano[3,2-g]quinolin-1-ium-4-yl)penta-2,4-dien-1-ylidene]-1-(5-carboxypentyl)-33-dimethylindoline-5-sulfonate, DY-751-sodium 2-[5-(2-tert-butyl-9-ethyl-6,8,8-trimethyl-8,9-dihydropyrano[3,2-g]quinolin-1-ium-4-yl)penta-2,4-dien-1-ylidene]-3-(3-carboxypropyl)-3-methyl-1-(3-sulfonatopropyl)indoline-5-sulfonate, DY-776-sodium 3-(3-carboxypropyl)-2-[5-(9-ethyl-6,8,8-trimethyl-2-phenyl-8,9-dihydropyrano[3,2-g]quinolin-1-ium-4-yl)penta-2,4-dien-1-ylidene]-3-methyl-1-(3-sulfonatopropyl)indoline-5-sulfonate, DY-782-disodium 2-[5-{4-tert-butyl-7-[ethyl(3-sulfonatopropyl)amino]-2H-chromen-2-ylidene}penta-1,3-dien-1-yl]-3-(3-carboxypropyl)-3-methyl-1-(3-sulfonatopropyl)-3H-indolium-5-sulfonate, eosin YS dye-disodium 2-(2,4,5,7-tetrabromo-6-oxido-3-oxo-3H-xanthen-9-yl)benzoate, eosin YS(2−)-2-(2,4,5,7-tetrabromo-6-oxido-3-oxo-3H-xanthen-9-yl)benzoate, epicocconone-(6S,9aS)-6-(hydroxymethyl)-3-[(1Z,4E,6E,8E)-1-hydroxy-3-oxodeca-1,4,6,8-tetraen-1-yl]-9a-methyl-5,6-dihydro-2H-furo[3,2-g]isochromene-2,9(9aH)-dione, ER-Tracke Blue-White DPX dye-N-(2-{[(4-{5-[4-(dimethylamino)phenyl]-1,3-oxazol-2-yl}phenyl)sulfonyl]amino ethyl)-2,3,4,5,6-pentafluorobenzamide, ethidium-3,8-diamino-5-ethyl-6-phenylphenanthridinium, ethidium homodimer-3,8-diamino-5-(3-[(2-([3-(3,8-diamino-6-methylphenanthridinium-5-yl)propyl]amino}ethyl)amino]propyl}-6-phenylphenanthridinium dichloride dihydrochloride, ethidium homodimer tetracation-3,8-diamino-5-(3-[(2-{[3-(3,8-diamino-6-methylphenanthridinium-5-yl)propyl]amino}ethyl)amino]propyl)-6-phenylphenanthridinium, ethyl eosin-potassium 2,4,5,7-tetrabromo-9-(2-[(ethyloxy)carbonyl]phenyl-3-oxo-3H-xanthen-6-olate, ethyl eosin anion-2,4,5,7-tetrabromo-9-{2-[(ethyloxy)carbonyl]phenyl}-3-oxo-3H-xanthen-6-olate, ethyl nile blue A-bis[9-(diethylamino)benzo[a]phenoxazin-7-ium]sulfate, Eu(tta)3DEADIT-(4-[4,6-di(1H-indazol-1-yl-κN$^2$)-1,3,5-triazin-2-yl-κN$^5$]-N,N-diethylaniline) {tris[4,4,4-trifluoro-3-(hydroxy-κO)-1-(thiophen-2-yl)but-2-en-1-onato-κO]}europium, EVOblue-30 dye-3-[{3-[(2-carboxyethyl)(methyl)iminio]-3H-phenoxazin-7-yl}(ethyl)amino]propane-1-sulfonate, exciton-2-{4-[4-(dimethylamino)phenyl]buta-1,3-dien-1-yl}-3-ethyl-1,3-benzothiazol-3-ium perchlorate, exciton(1−)-2-{4-[4-(dimethylamino)phenyl]buta-1,3-dien-1-yl}-3-ethyl-1,3-benzothiazol-3-ium, Fluo-3-{[2-(2-{2-[bis(carboxymethyl)amino]-5-(2,7-dichloro-6-hydroxy-3-oxo-3H-xanthen-9-yl)phenoxy}ethoxy)-4-methylphenyl](carboxymethyl)amino}acetic acid, fluorescein bis-arsenide-2-(4,5-di-1,3,2-dithiarsolan-2-yl-6-hydroxy-3-oxo-3H-xanthen-9-yl) benzoic acid fluorescein isothiocyanate-3',6'-dihydroxy-4-isothiocyanato-3H-spiro[2-benzofuran-1,9'-xanthen]-3-one, FluorX 5-isomer-5-[(5-carboxypentyl)carbamoyl]-2-(6-hydroxy-3-oxo-3H-xanthen-9-yl)benzoic acid, FluorX 6-isomer-4-[(5-carboxypentyl)carbamoyl]-2-(6-hydroxy-3-oxo-3H-xanthen-9-yl)benzoic acid, FM 1-43 dye-4-{2-[4(dibutylamino)phenyl]ethenyl}-1-[3-(triethylammonio)propyl]pyridinium dibromide, FM 1-43(2+)-4-{2-[4-(dibutylamino)phenyl]ethenyl}-1-[3-(triethylammonio)propyl]pyridinium. FM 4-64 dye-4-{6-[4-(dibutylamino)phenyl]hexa-1,3,5-trien-1-yl}-1-[3-(triethylammonio)propyl]pyridinium dibromide, FM 4-64(2−)-4-16-[4-(dibutylamino)phenyl]hexa-1,3,5-trien-1-yl)-1-[3-(triethylammonio)propyl]pyridinium, fort orange 600-nanocrystal FUN-1-2-[(2-chloro-1-phenylquinolin-4(1H)-ylidene)methyl]-3-methyl-1,3-benzothiazol-3-ium iodide, fura red-(acetyloxy)methyl[{2-[(acetyloxy)methoxy]-2-oxoethyl}(5-{2-[2-(bis{2-[(acetyloxy)methoxy]-2-oxoethyl}amino)-5-methylphenoxy]ethoxy}-2-[(5-oxo-2-thioxoimidazolidin-4-ylidene)methyl]-1-benzofuran-6-yl)amino]acetate, fura-2 dye-pentapotassitum 2-(6-[bis(carboxylatomethyl)amino]-5-{2-[2-({2-[bis(carboxylatomethyl)amino]phenyl}oxy)ethyl]oxy}-1-benzofuran-2-yl)-4,5-dihydro-1,3-oxazole-5-carboxylate, fura-2(5−)-2-{6-[bis(carboxylatomethyl)amino]-5-(2-{2-[bis(carboxylatomethyl)amino]phenoxy}ethoxy)-1-benzofuran-2-yl}-4,5-dihydro-1,3-oxazole-5-carboxylate, HCK-123 dye-N-[2-(dimethylamino)ethyl]-6-[(7-nitro-2,1,3-benzoxadiazol-4-yl)amino]hexanamide hemo red 720-nanocrystal, herniarin-7-(methyloxy)-2H-chromen-2-one hops yellow 560-Q dot, HOxAsH-bis(1,2-ethanedithiol)-4,5-di-1,3,2-dithiarsolan-2-yl-3,6-dihydroxy-9H-xanthen-9-one, Indo-1 dye-2-4-[bis(carboxymethyl)amino]-3-{[2-({2-[bis(carboxymethyl)amino]-5-methylphenyl}oxy)ethyl]oxy}phenyl)-1H-indole-6-carboxylic acid, Ir(Cn)$_2$(acac)-bis[7-(diethylamino)-3-(1-methyl-1H-benzimidazol-2-yl-κN$^3$)-2-oxo-2H-chromen-4-yl-κC$^4$][4-(hydroxy-κO)pent-3-en-2-onato-κO]iridium, Ir(Cs)$_2$(acac)-bis[3-(1,3-benzothiazol-2-yl-κN)-7-(diethylamino)-2-oxo-2H-chromen-4-yl-κC$^4$][4-(hydroxy-κO)pent-3-en-2-onato-κO] iridium. JOJO-1 dye-2,2'-{propane-1,3-diylbis[(dimethylanmmonio)propane-3,1-diylquinolin-1-yl-4-ylidenemethylylidene]}bis(4-methyl[1,3]oxazolo[4,5-b]pyridin-4-ium)tetraiodide, JOJO-1(4+)-2,2'-{propane-1,3-diylbis[(dimethylammonio)propane-3,1-diylquinolin-1-yl-4-ylidenemethylylidene]}bis(4-methyl[1,3]oxazolo[4,5-b]pyridin-4-ium), Lake Placid 490-Qdot, LDS 751 dye-6-(dimethylamino)-2-{4-[4-(dimethylamino)phenyl]buta-1,3-dien-1-yl}-1-ethylquinolinium perchlorate, LDS 751(1)-6-(dimethylamino)-2-{4-[4-(dimethylamino)phenyl]buta-1,3-dien-1-yl}-1-ethylquinolinium, lissamine rhodamine-sodium 4-[3,6-bis(diethylamino)-2,7-dimethylxanthenium-9-yl]benzene-1,3-disulfonate lissamine rhodamine anion-4-[3,6-bis(diethylamino)-2,7-dimethylxanthenium-9-yl]benzene-1,3-disulfonate, LoLo-1 dye-2,2'-{propane-1,3-diylbis[(dimethylammonio)propane-3, I-diylquinolin-1-yl- 4-ylidenemethylylidene])bis(6-bromo-4-methyl[1,3]thiazolo[4,5-b]pyridin-4-ium)tetraiodide, LoLo-1(4+)-2,2'-propane-1,3-diylbis[(dimethylammonio)propane-3,1-diylquinolin-1-yl-4-ylidenemethylylidene)]bis(6-bromo-4-methyl[1,3]thiazolo[4,5-b]pyridin-4-ium), lucifer yellow anion-6-amino-2-(hydrazinocarbonyl)-1,3-dioxo-2,3-dihydro-1H-benzo[de]isoquinoline-5,8-disulfonate, lucifer yellow carbohydrazide dye-dilithium 6-amino-2-[(hydrazinocarbonyl)amino]-1,3-dioxo-2,3-dihydro-1H-benzo[de]isoquinoline-5,8-disulfonate, lucifer yellow dye-dilithium 6-amino-2-(hydrazinocarbonyl)-1,3-dioxo-2,3-dihydro-1H-benzo[de]isoquinoline-5,8-disulfonate, magnesium green-pentapotassium 2,2'-{[2-(carboxylatomethoxy)-4-{[(2',7'-dichloro-3',6'-dioxido-3-oxo-3H-spiro[2-benzofuran-1,9'-xanthen]-5-yl)carbonyl]amino}phenyl]imino; diacetate, magnesium green (5−)-2,2'-{[2-(carboxylatomethoxy)-4-{[(2',7'-dichloro-3',6'-dioxido-3-oxo-3H-spiro[2-benzofuran-1,9'-xanthen]-5-yl)carbonyl]amino}phenyl]imino}diacetate magnesium octaethylporphyrin-[2,3,7,8,12,13,17,18-octaethylporphyrinato(2−)-$\kappa^4$,$N^{21}$,$N^{22}$,$N^{23}$,$N^{24}$]magnesium, magnesium orange G-magnesium 7-hydroxy-8-(phenyldiazenyl)naphthalene-1,3-disulfonate-water (⅛), magnesium phthalocyanine-[29H,31H-phthalocyaninato(2−)-$\kappa^4$,$N^{29}$,$N^{30}$,$N^{31}$,$N^{32}$]magnesium, magnesium tetraphenylporphyrin-[5,10,15,20-tetraphenylporphyrinato(2−)-$\kappa^4$,$N^{21}$,$N^{22}$,$N^{23}$,$N^{24}$]magnesium, malachite green-4-{[4-(dimethylamino)phenyl](phenyl)methylene}-N,N-dimethylcyclohexa-2,5-dien-1-iminium chloride, malachite green cation-4-{[4-(dimethylamino)phenyl](phenyl)methylene}-N,N-dimethylcyclohexa-2,5-dien-1-iminium, malachite green isothiocyanate N-(4-{[4-(dimethylamino)phenyl](4-isothiocyanatophenyl)methylidene}cyclohexa-2,5-dien-1-ylidene)-N-methylmethanaminium perchlorate, malachite green isothiocyanate cation-N-(4-{[4-(dimethylamino)phenyl](4-isothiocyanatophenyl)methylidene}cyclohexa-2,5-dien-1-ylidene)-N-methylmethanaminium, maple red-orange 620-Qdot marina blue dye-2-(6,8-difluoro-7-hydroxy-4-methyl-2-oxo-2H-chromen-3-yl)acetohydrazide, merocyanine 540-sodium 3-2-[4-(1,3-dibutyl-4,6-dioxo-2-sulfanylidenetetrahydropyrimidin-5(2H)-ylidene)but-2-en-1-ylidene]-1,3-benzoxazol-3(2H)-yl propane-1-sulfonate, merocyanine 540 anion-3-{2-[4-(1,3-dibutyl-4,6-dioxo-2-sulfanylidenetetrahydropyrimidin-5(2H)-ylidene)but-2-en-1-ylidene]-1,3-benzoxazol-3(2H)-yl}propane-1-sulfonate, methylene blue-3,7-bis(dimethylamino)phenothiazin-5-ium chloride, mitoTracker Deep Red 633-1-{4-[(chloromethyl)phenyl]methyl}-3,3-dimethyl-2-[5-(1,3,3-trimethyl-1,3-dihydro-2H-indol-2-ylidene)penta-1,3-dien-1-yl]-3H-indolium chloride, mitoTracker Green FM-2-[3-{5,6-dichloro-1,3-bis[4-(chloromethyl)phenyl]-1,3-dihydro-2H-benzimidazol-2-ylidene}prop-1-en-1-yl]-3-methyl-1,3-benzoxazol-3-ium chloride, mitoTracker Orange-N-{9-[4-(chloromethyl)phenyl]-6-(dimethylamino)-3H-xanthen-3-ylidene}-N-methylmethanaminium chloride, mitoTracker Red-9-[4-(chloromethyl)phenyl]-2,3,6,7,12,13,16,17-octahydro-1H,5H, 11H,15H-pyrido[3,2,1-ij]quinolizino[1',9':6,7,8]chromeno[2,3-f]quinolin-4-ium chloride monobromobimane-3-(bromomethyl)-2,5,6-trimethyl-1H,7H-pyrazolo[1,2-a]pyrazole-1,7-dione, monochlorobimane-3-(chloromethyl)-2,5,6-trimethyl-1H,7H-pyrazolo[1,2-a]pyrazole-1,7-dione, monodansylcadaverine-N-(6-aminohexyl)-5-(dimethylamino)naphthalene-1-sulfonamide, nile blue dye-5-amino-9-(diethylamino)benzo[a]phenoxazin-7-ium chloride, nile blue perchlorate-5-amino-9-(diethylamino)benzo[a]phenoxazin-7-ium perchlorate, nile red dye-9-(diethylamino)-5H-benzo[a]phenoxazin-5-one, NIR-1 dye-dipotassium 2-(7-[5-carboxy-3,3-dimethyl-1-(4-sulfonatobutyl)-1,3-dihydro-2H-indol-2-ylidene]hepta-1,3,5-trien-1-yl)-3-ethyl-1,1-dimethyl-1H-benzo[e]indolium-6,8-disulfonate. NIR-1(2−)-2-{7-[5-carboxy-3,3-dimethyl-1-(4-sulfonatobutyl)-1,3-dihydro-2H-indol-2-ylidene]hepta-1,3,5-trien-1-yl}-3-ethyl-1,1-dimethyl-1H-benzo[e]indolium-6,8-disulfonate, NIR-2 dye-dipotassium 2-{5-[5-carboxy-3,3-dimethyl-1-(4-sulfonatobutyl)-1,3-dihydro-2H-indol-2-ylidene]penta-1,3-dien-1-yl}-3-ethyl-1,1-dimethyl-1H-benzo[e]indolium-6,8-disulfonate, NIR-2(2−)-2-(5-[5-carboxy-3,3-dimethyl-1-(4-sulfonatobutyl)-1,3-dihydro-2H-indol-2-ylidene]penta-1,3-dien-1-yl)-3-ethyl-1,1-dimethyl-1H-benzo[e]indolium-6,8-disulfonate, NIR-3 dye-dipotassium 2-{7-[5-carboxy-3,3-dimethyl-1-(4-sulfonatobutyl)-1,3-dihydro-2H-indol-2-ylidene]hepta-1,3,5-trien-1-yl}-3,3-dimethyl-1-(4-sulfonatobutyl)-3H-indolium-5-sulfonate, NIR-3(2−)-2-{7-[5-carboxy-3,3-dimethyl-1-(4-sulfonatobutyl)-1,3-dihydro-2H-indol-2-ylidene]hepta-1,3,5-trien-1-yl}-3,3-dimethyl-1-(4-sulfonatobutyl)-3H-indolium-5-sulfonate, NIR-4 dye-dipotassium 2-(5-[5-carboxy-3,3-dimethyl-1-(4-sulfonatobutyl)-1,3-dihydro-2H-indol-2-ylidene]penta-1,3-dien-1-yl)-3,3-dimethyl-1-(4-sulfonatobutyl)-3H-indolium-5-sulfonate. NIR-4(2−)-2-(5-[5-carboxy-3,3-dimethyl-1-(4-sulfonatobutyl)-1,3-dihydro-2H-indol-2-ylidene]penta-1,3-dien-1-yl-3,3-dimethyl-1-(4-sulfonatobutyl)-3H-indolium-5-sulfonate, NIR-820 dye-4-{5-carboxy-2-[2-(3-{2-[5-carboxy-3,3-dimethyl-1-(4-sulfobutyl)-1,3-dihydro-2H-indol-2-ylidene]ethylidene}-2-chlorocyclohex-1-en-1-yl)ethenyl]-3,3-dimethyl-3H-indolium-1-yl}butane-1-sulfonate. OG-514 dye-4-[(carboxymethyl)sulfanyl]-2-(2,7-difluoro-6-hydroxy-3-oxo-3H-xanthen-9-yl)-3,5,6-trifluorobenzoic acid, omocianine-2-(4-methyl-7-[5-sulfo-1-(2-sulfoethyl)-1,3-dihydro-2H-indol-2-ylidene]hepta-1,3,5-trien-1-yl-1-(2-sulfoethyl)-3H-indolium-5-sulfonate, oregon green 488-4-(2,7-difluoro-6-hydroxy-3-oxo-3H-xanthen-9-yl)isophthalic acid, oxazine-1-3,7-bis(diethylamino)phenoxazin-5-ium, oxazine-1 perchlorate-3,7-bis(diethylamino)phenoxazin-5-ium perchlorate, oxazine-170(1+)-5-(ethylamino)-9-[ethyl(methyl)amino]-10-methylbenzo[a]phenoxazin-7-ium, oxazine-750-14-(ethylamino)-2,3,6,7-tetrahydro-1H,5H-benzo[a]quinolizino[1,9-hi]phenoxazin-16-ium, pacific blue-6,8-difluoro-7-hydroxy-2-oxo-2H-chromene-3-carboxylic acid, pacific blue succinimidyl ester-1-{[(6,8-difluoro-7-hydroxy-2-oxo-2H-chromen-3-yl)carbonyl]oxy}pyrrolidine-2,5-dione, palladium(11) meso-tetraphenyl-tetrabenzoporphyrin, palladium(II) octaethylporphyrinketone-(3,3,7,8,12,13,17,18-octaethylporphyrin-2(3H)-one-$\kappa^4$,$N^{21}$,$N^{22}$,$N^{23}$,$N^{24}$)paladium, palladium(II)-5,10,15,20-tetrakis-(2,3,4,5,6-pentafluorphenyl)-porphyrin-[5,10,15,20-tetrakis(pentafluorophenyl)porphyrin-$\kappa^4$,$N^{21}$,$N^{22}$,$N^{23}$,$N^{24}$]palladium, perylenediimide-isoquino[4',5',6':6,5,10]anthra[2,19-def]isoquinoline-1,3,8,10(2H,9H)-tetrone, pibenzimol-4-[5-(4-methylpiperazin-1-yl)-1H, 1'H-2,5'-bibenzimidazol-2'-yl]phenol, pinacyanol cation-1-ethyl-2-[3-(1-ethylquinolin-2(1H)-ylidene)prop-1-en-1-yl]quinolinium, pinacyanol iodide-1-ethyl-2-[3-(1-ethylquinolin-2(1H)-ylidene)prop-1-en-1-yl]quinolinium iodide, platinum(II) 5,10,15,20-tetrakis-(2,3,4,5,6-pentafluorophenyl)porphyrin-[5,10,15,20-tetrakis(pentafluorophenyl)porphyrinato-$\kappa^4$,$N^{21}$,$N^{22}$,$N^{23}$,$N^{24}$]platinum(II), platinum(II) octaethylporphyrin-(2,3,7,8,12,13,17,18-octaethylporphyrinato-$\kappa^4$,$N^{21}$,$N^{22}$,$N^{23}$,$N^{24}$)platinum(II), platinum(II) octaethylporphyrin ketone-[3,3,7,8,12,13,17,18-octaethylporphyrin-2(3H)-onato-$\kappa^4$,$N^{21}$,$N^{22}$,$N^{23}$,$N^{24}$]platinum(II), Po-Pro-1-3-methyl-2-({1-[3-(trimethylammonio)propyl]pyridin-4(1H)-ylidene}methyl)-

1,3-benzoxazol-3-ium diiodide, Po-Pro-1(2+)-3-methyl-2-({1-[3 (trimethylammonio)propyl]pyridin-4(1H)-ylidene}methyl)-1,3-benzoxazol-3-ium, Po-Pro-3-3-methyl-2-(3-{1-[3-(trimethylammonio)propyl]pyridin-4 (1H)-ylidene}prop-1-en-1-yl)-1,3-benzoxazol-3-ium diiodide, Po-Pro-3(2+)-3-methyl-2-(3-{1-[3-(trimethylammonio)propyl]pyridin-4(1H)-ylidene}prop-1-en-1-yl)-1,3-benzoxazol-3-ium, PoPo-1-2,2'-{propane-1,3-diylbis[(dimethylazaniumdiyl)propane-3,1-diylpyridin-1-yl-4-ylidenemethylylidene]}bis(3-methyl-1,3-benzoxazol-3-ium)tetraiodide, PoPo-1(4+)-1,1'-{propane-1,3-diylbis[(dimethylazaniumdiyl)propane-3,1-diyl]}bis{4-[(3-methyl-1,3-benzoxazol-2(3H)-ylidene)methyl]pyridinium}, PoPo-3-1,1'-{propane-1,3-diylbis[(dimethylazaniumidiyl) propane-3,1-diyl]}bis {4-[3-(3-methyl-1,3-benzoxazol-2 (3H)-ylidene)prop-1-en-1-yl]pyridinium}tetraiodide, PoPo-3(4+)-1,1'-{propane-1,3-diylbis[(dimethylazaniumdiyl) propane-3,1-diyl]}bis{4-[3-(3-methyl-1,3-benzoxazol-2 (3H)-ylidene)prop-1-en-1-yl]pyridinium}, POPOP-2,2'-benzene-1,4-diylbis(5-phenyl-1,3-oxazole), propidium-3,8-diamino-5-{3-[diethyl(methyl)ammonio]propyl}-6-phenylphenanthridinium, pyranine-trisodium 8-hydroxypyrene-1,3,6-trisulfonate, pyranine(3−)-8-hydroxypyrene-1,3,6-trisulfonate, Qdot 525, QPYMe2 fluorescent dye-6-(dimethylamino)-2,10-bis(1-methylpyridinium-4-yl)imidazo[1,5-a:3,4-a']dipyridin-5-ium, QSY21 succinimidyl ester-2-[6-(1,3-dihydro-2H-isoindol-2-yl)-9-{2-[(4-{[(2,5-dioxopyrrolidin-1-yl)oxy]carbonyl}piperidin-1-yl)sulfonyl]phenyl}-3H-xanthen-3-ylidene]-2,3-dihydro-1H-isoindolium chloride, QSY21 succinimidyl ester(1+)-2-[6-(1,3-dihydro-2H-isoindol-2-yl)-9-{2-[(4-{[(2,5-dioxopyrrolidin-1-yl)oxy]carbonyl}piperidin-1-yl)sulfonyl] phenyl}-3H-xanthen-3-ylidene]-2,3-dihydro-1H-isoindolium, QSY35 succinimidyl ester-1-[({4-[(7-nitro-2, 1,3-benzoxadiazol-4-yl)amino]phenyl}acetyl)oxy] pyrrolidine-2,5-dione, QSY7 succinimidyl ester-N-(9-{2-[(4-{[(2,5-dioxopyrrolidin-1-yl)oxy]carbonyl}piperidin-1-yl)sulfonyl]phenyl}-6-[methyl(phenyl)amino]-3H-xanthen-3-ylidene)-N-methylanilinium chloride, QSY7 succinimidyl ester(1+)-N-(9-{2-[(4-{[(2,5-dioxopyrrolidin-1-yl)oxy] carbonyl}piperidin-1-yl)sulfonyl]phenyl}-6-[methyl(phenyl)amino]-3H-xanthen-3-ylidene)-N-methylanilinium, QSY9 succinimidyl ester-N-(9-{2-[(4-{[(2,5-dioxopyrrolidin-1-yl)oxy]carbonyl}piperidin-1-yl)sulfonyl]phenyl}-6-[methyl(4-sulfophenyl)amino]-3H-xanthen-3-ylidene)-N-methyl-4-sulfoanilinium chloride, QSY9 succinimidyl ester (1+)-N-(9-{2-[(4-{[(2,5-dioxopyrrolidin-1-yl)oxy] carbonyl}piperidin-1-yl)sulfonyl]phenyl}-6-[methyl(4-sulfophenyl)amino]-3H-xanthen-3-ylidene)-N-methyl-4-sulfoanilinium, resorufin bis-arsenide-4,6-di-1,3,2-dithiarsolan-2-yl-7-hydroxy-3H-phenoxazin-3-one, rhod-2 dye-N-[9-(4-{bis[2-(acetoxymethoxy)-2-oxoethyl]amino}-3-[2-(2-{bis[2-(acetoxymethoxy)-2-oxoethyl]amino}-5-methylphenoxy)ethoxy]phenyl)-6-(dimethylamino)-3H-xanthen-3-ylidene]-N-methylmethanaminium bromide, rhod-2(1+)-N-[9-(4-{bis[2-(acetoxymethoxy)-2-oxoethyl] amino}-3-[2-(2-{bis[2-(acetoxymethoxy)-2-oxoethyl] amino}-5-methylphenoxy)ethoxy]phenyl)-6-(dimethylamino)-3H-xanthen-3-ylidene]-N-methylmethanaminium, rhodamine 101-2-(2,3,6,7,12,13,16,17-octahydro-1H,5H, 11H,15H-pyrido[3,2,1-ij]quinolizino[1',9':6,7,8]chromeno [2,3-f]quinolin-4-ium-9-yl)benzoate, rhodamine 110-3,6-diamino-9-(2-carboxyphenyl)xanthenium chloride, rhodamine 110(1+)-3,6-diamino-9-(2-carboxyphenyl) xanthenium, rhodamine 123-6-amino-9-[2-(methoxycarbonyl)phenyl]-3H-xanthen-3-iminium chloride, rhodamine 123(1+)-6-amino-9-[2-(methoxycarbonyl)phenyl]-3H-xanthen-3-iminium, rhodamine 6G-9-[2-(ethoxycarbonyl)phenyl]-3,6-bis(ethylamino)-2,7-dimethylxanthenium chloride, rhodamine 6G(1+)-9-[2-(ethoxycarbonyl)phenyl]-3,6-bis(ethylamino)-2,7-dimethylxanthenium, rhodamine 700 perchlorate-9-(trifluoromethyl)-2,3,6,7,12,13,16,17-octahydro-1H,5H, 11H,15H-pyrido[3,2,1-ij]quinolizino[1',9':6,7,8]chromeno [2,3-f]quinolin-4-ium perchlorate, rhodamine B—N-[9-(2-carboxyphenyl)-6-(diethylamino)-3H-xanthen-3-ylidene]-N-ethylethanaminium chloride, rhodamine B 5-isothiocyanate-N-[9-(2-carboxy-4-isothiocyanatophenyl)-6-(diethylamino)-3H-xanthen-3-ylidene]-N-ethylethanaminium chloride, rhodamine B 6-isothiocyanate-N-[9-(2-carboxy-5-isothiocyanatophenyl)-6-(diethylamino)-3H-xanthen-3-ylidene]-N-ethylethanaminium chloride N-[9-(2-carboxy-5-isothiocyanatophenyl)-6-(diethylamino)-3H-xanthen-3-ylidene]-N-ethylethanaminium chloride, rhodamine B isothiocyanate, rhodamine B(1+)-N-[9-(2-carboxyphenyl)-6-(diethylamino)-3H-xanthen-3-ylidene]-N-ethylethanaminium, rhodamine green, rhodamine green 5-isomer-6-amino-9-(2,4-dicarboxyphenyl)-3H-xanthen-3-iminium, rhodamine green 6-isomer-6-amino-9-(2,5-dicarboxyphenyl)-3H-xanthen-3-iminium, rhodamine red-X-5-[(5-carboxypentyl)sulfamoyl]-2-[6-(diethylamino)-3-(diethylimino)-3H-xanthen-9-yl]benzenesulfonate, rose bengal-dipotassium 2,3,4,5-tetrachloro-6-(2,4,5,7-tetraiodo-6-oxido-3-oxo-3H-xanthen-9-yl)benzoate, rose bengal(2−)-2,3,4,5-tetrachloro-6-(2,4,5,7-tetraiodo-6-oxido-3-oxo-3H-xanthen-9-yl)benzoate, snake-eye red 900-Qot, SNIR1 dye-potassium (2E)-3-ethyl-2-[(2E,4E)-5-{5-[(iodoacetyl) amino]-1,3,3-trimethyl-3H-indolium-2-yl}penta-2,4-dien-1-ylidene]-1,1-dimethyl-2,3-dihydro-1H-benzo[e]indole-6, 8-disulfonate, SNIR1 (1−)-(2E)-3-ethyl-2-[(2E,4E)-5-{5-[(iodoacetyl)amino]-1,3,3-trimethyl-3H-indolium-2-yl}penta-2,4-dien-1-ylidene]-1,1-dimethyl-2,3-dihydro-1H-benzo[e]indole-6,8-disulfonate, SNIR2 dye-potassium (2E)-3-ethyl-2-[(2E,4E,6E)-7-{5-[(iodoacetyl)amino]-1,3,3-trimethyl-3H-indolium-2-yl}hepta-2,4,6-trien-1-ylidene]-1, 1-dimethyl-2,3-dihydro-1H-benzo[e]indole-6,8-disulfonate, SNIR2(1−)-(2E)-3-ethyl-2-[(2E,4E,6E)-7-{5-[(iodoacetyl) amino]-1,3,3-trimethyl-3H-indolium-2-yl}hepta-2,4,6-trien-1-ylidene]-1,1-dimethyl-2,3-dihydro-1H-benzo[e]indole-6,8-disulfonate, SNIR3 dye-dipotassium(2E)-2-[(2E, 4E)-5-{5-[(iodoacetyl)amino]-1,3,3-trimethyl-3H-indolium-2-yl}penta-2,4-dien-1-ylidene]-1,1-dimethyl-3-(2-sulfonatoethyl)-2,3-dihydro-1H-benzo[e]indole-6,8-disulfonate, SNIR4 dye-dipotassium (2E)-2-[(2E,4E,6E)-7-{5-[(iodoacetyl)amino]-1,3,3-trimethyl-3H-indolium-2-yl}hepta-2,4,6-trien-1-ylidene]-1,1-dimethyl-3-(2-sulfonatoethyl)-2,3-dihydro-1H-benzo[e]indole-6,8-disulfonate, SNIR4(2−)-(2E)-2-[(2E,4E,6E)-7-{5-[(iodoacetyl)amino]-1,3,3-trimethyl-3H-indolium-2-yl}hepta-2,4,6-trien-1-ylidene]-1,1-dimethyl-3-(2-sulfonatoethyl)-2,3-dihydro-1H-benzo[e]indole-6,8-disulfonate, sodium green-tetrakis(N,N,N-trimethylmethanaminium)5-({[4-(13-{4-[({3-carboxylato-4-[(2,7-dichloro-6-oxido-3-oxo-3H-xanthen-9-yl)methyl] phenyl}carbonyl)amino]-2,5-bis(methyloxy)phenyl}-1,4, 10-trioxa-7,13-diazacyclopentadecan-7-yl)-2-hydroxy-5-(methyloxy)phenyl]amino}carbonyl)-2-(2,7-dichloro-6-oxido-3-oxo-3H-xanthen-9-yl)benzoate, sodium green(4−)-3,3'-{1,4,10-trioxa-7,13-diazacyclopentadecane-7,13-diylbis[(2,5-dimethoxy-4,1-phenylene)carbamoyl]}bis[6-(2,7-dichloro-6-oxido-3-oxo-3H-xanthen-9-yl)benzoate], sodium-binding benzofuran isophthalate-4,4'-{1,4,10-trioxa-7,13-diazacyclopentadecane-7,13-diylbis[5-(methyloxy)-1-benzofuran-6,2-diyl]}dibenzene-1,3-dicarboxylic acid, squarylium dye III-2-[4 (dimethylamino)phenyl]-4-[4-(dimethyliminio)cyclohexa-2,5-dien-1-ylidene]-3-oxocyclobut-1-en-1-olate, succinyl-Leu-Leu-Val-Tyr-7-amino-4-methylcoumarin-N-(3-carboxypropanoyl)-L-leucyl-L-leucyl-L-valyl-N-(4-methyl-2-oxo-2H-chromen-7-yl)-L-tyrosinamide, sulforhodamine 101-4-(2,3,6,7,12,13,16,17-octahydro-1H,5H, 11H,15H-pyrido[3,2,1-ij]quinolizino[1',9':6,7,8]chromeno[2,3-f]quinolin-18-ium-9-yl)-3-sulfobenzenesulfonate, sulforhodamine G-sodium 4-[3,6-bis(ethylamino)-2,7-dimethylxanthenium-9-yl]benzene-1,3-disulfonate, sulforhodamine G anion-4-[3,6-bis(ethylamino)-2,7-dimethylxanthenium-9-yl]benzene-1,3-disulfonate, terrylendiimide-2,11-bis{2,6-bis[1-(propan-2-yl)]phenyl}benzo[13,14]isoquino[6',5',4':8,9,10]pentapheno[3,4,5-def]isoquinoline-1,3,10,12(2H,11H)-tetrone, tetramethylrhodamine chloride-9-(2-carboxyphenyl)-3,6-bis(dimethylamino)xanthenium chloride, tetramethylrhodamine phalloidin-2-[6-(dimethylamino)-3-(dimethyliminio)-3H-xanthen-9-yl]-5-[({(2R)-2-hydroxy-3-[(2S,3aS,6S,9S,18R,23R,26S,29S)-2-hydroxy-23-[(1S)-1-hydroxyethyl]-6,26-dimethyl-4,7,19,22,25,28,31-heptaoxo-1,2,3,3a,4,5,6,7,8,9,10,15,18,19-tetradecahydro-17H-18,9-(epiminoethanoiminoethanoiminoethanoiminomethano)pyrrolo[1',2':5,6]tetramethylrhodamnine thiocyanate-9-(2-carboxy-4-thiocyanatophenyl)-3,6-bis(dimethylamino)xanthenium chloride, tetramethylrhodamine thiocyanate cation-9-(2-carboxy-4-thiocyanatophenyl)-3,6-bis(dimethylamino)xanthenium, tetramethylrosamine chloride-6-(dimethylamino)-N,N-dimethyl-9-phenyl-3H-xanthen-3-iminium chloride, texas red-5-(chlorosulfonyl)-2-(2,3,6,7,12,13,16,17-octahydro-1H,5H,11H,15H-pyrido[3,2,1-ij]quinolizino[1,9':6,7,8]chromeno[2,3-f]quinolin-4-ium-9-yl)benzenesulfonate, texas red DHPE-N,N-diethylethanaminium 5-({[7-(hexadecanoyloxy)-4,4-dioxido-10-oxo-3,5,9-trioxa-4-phosphapentacos-1-yl]amino; sulfonyl)-2-(2,3,6,7,12,13,16,17-octahydro-1H,5H, 11H,15H-pyrido[3,2,1-ij]quinolizino[1',9':6,7,8]chromeno[2,3-f]quinolin-4-ium-9-yl)benzenesulfonate, texas red DHPE(1−)-5-(([7-(hexadecanoyloxy)-4,4-dioxido-10-oxo-3,5,9-trioxa-4λ$^5$-phosphapentacos-1-yl]amino}sulfonyl)-2-(2,3,6,7,12,13,16,17-octahydro-1H,5H, 11H,15H-pyrido[3,2,1-ij]quinolizino[1',9':6,7,8]chromeno[2,3-f]quinolin-4-ium-9-yl)benzenesulfonate, texas red-X-5-{[(5-carboxypentyl)amino]sulfonyl}-2-(2,3,6,7,12,13,16,17-octahydro-1H,5H,11H,15H-pyrido[3,2,1-ij]quinolizino[1',9':6,7,8]chromeno[2,3-f]quinolin-4-ium-9-yl)benzenesulfonate, thiazole orange-1-methyl-4-[(3-methyl-1,3-benzothiazol-2(3H)-ylidene)methyl]quinolinium 4-methylbenzenesulfonate thiazole orange cation-1-methyl-4-[(3-methyl-1,3-benzothiazol-2(3H)-ylidene)methyl]quinolinium, thionine acetate-3,7-diaminophenothiazin-5-ium acetate, thionine cation-3,7-diaminophenothiazin-5-ium, To-Pro-1-3-methyl-2-({1-[3-(trimethylammonio)propyl]quinolin-4(1H)-ylidene}methyl)-1,3-benzothiazol-3-ium diiodide, To-Pro-1(2+)-3-methyl-2-({1-[3-(trimethylammonio)propyl]quinolin-4(1H)-ylidene}methyl)-1,3-benzothiazol-3-ium, To-Pro-3-3-methyl-2-(3-{1-[3-(trimethylammonio)propyl]quinolin-4(1H)-ylidene}prop-1-en-1-yl)-1,3-benzothiazol-3-ium diiodide, To-Pro-3(2+)-3-methyl-2-(3-{1-[3-(trimethylammonio)propyl]quinolin-4(1H)-ylidene}prop-1-en-1-yl)-1,3-benzothiazol-3-ium, topaz-Qdot/nanocrystal, ToTo-1-1,1'-{propane-1,3-diylbis[(dimethylammonio)propane-3,1-diyl]}bis {4-[(3-methyl-1,3-benzothiazol-2(3H)-ylidene)methyl]quinolinium}tetraiodide, ToTo-1(4+)-1,1'-{propane-1,3-diylbis[(dimethylazaniumdiyl)propane-3,1-diyl]}bis {4-[(3-methyl-1,3-benzothiazol-2(3H)-ylidene)methyl] quinolinium}, ToTo-3-1,1'-[4,8-bis(dimethyliminio)undecane-1,11-diyl]bis {4-[3-(3-methyl-1,3-benzothiazol-2(3H)-ylidene)prop-1-en-1-yl]quinolinium}tetraiodide, ToTo-3(4−)-1,1'-[4,8-bis(dimethyliminio)undecane-1,11-diyl]bis{4-[3-(3-methyl-1,3-benzothiazol-2(3H)-ylidene)prop-1-en-1-yl]quinolinium}, tris(1,10-phenanthroline)ruthenium(II) dichloride dehydrate-tris 1,10-phenanthroline-κ$^2$N$^1$,N$^{10}$)ruthenium(2+)dichloride dehydrate, tris(2,2'-bipyridine)ruthenium(II)-tris(2,2'-bipyridine-κ$^2$N$^1$,N$^{1'}$) ruthenium(II), tris(2,2'-bipyridine)ruthenium(II) dichloride-tris(2,2'-bipyridine-κ$^2$N$^1$,N$^{1'}$)ruthenium(II) dichloride, tris (4,4'-diphenyl-2,2'-bipyridine)ruthenium(II)-tris(4,4'-diphenyl-2,2'-bipyridine-κ$^2$N$^1$,N$^{1'}$)ruthenium(II), tris(4,4'-diphenyl-2,2'-bipyridine)ruthenium(II) chloride-tris(4,4'-diphenyl-2,2'-bipyridine-κ$^2$N$^1$,N$^{1'}$)ruthenium(II) dichloride, tris(4,7-diphenyl-1,10-phenanthroline)ruthenium(II)-tris(4,7-diphenyl-1,10-phenanthroline-κ$^2$N$^1$,N$^{10}$)ruthenium(II), X-rhod-1-9-(4-{bis[2-(acetyloxymethoxy)-2-oxoethyl]amino}-3-[2-(2-{bis[2-(acetyloxymethoxy)-2-oxoethyl]amino}-5-methylphenoxy)ethoxy]phenyl)-2,3,6,7,12,13,16,17-octahydro-1H,5H, 11H, 15H-pyrido[3,2,1-ij]quinolizino[1',9':6,7,8]chromeno[2,3-f]quinolin-4-ium bromide, X-rhod-1(1+)-9-(4-{bis[2-(acetyloxymethoxy)-2-oxoethyl]amino}-3-[2-(2-{bis[2-(acetyloxymethoxy)-2-oxoethyl]amino}-5-methylphenoxy)ethoxy]phenyl)-2,3,6,7,12,13,16,17-octahydro-1H,5H,11H,15H-pyrido[3,2,1-ij]quinolizino[1,9':6,7,8]chromeno[2,3-f]quinolin-4-ium, yakima yellow phosphoramidite-2',5,5',6-tetrachloro-7'-{12-[di(propan-2-yl)amino]-15-hydroxy-3-oxo-11,13-dioxa-4-aza-12-phosphapentadecyl}-4'-methyl-3-oxo-3H-spiro[2-benzofuran-1,9'-xanthene]-3',6'-diyl bis(2,2-dimethylpropanoate), Yo-Pro-1-3-methyl-2-[{1-[3-(trimethylammonio)propyl]quinolin-4(1H)-ylidene}methyl]-1,3-benzoxazol-3-ium diiodide, Yo-Pro-1(2+)-3-methyl-2-[{1-[3-(trimethylammonio)propyl]quinolin-4(1H)-ylidene}methyl]-1,3-benzoxazol-3-ium, Yo-Pro-3-3-methyl-2-(3-{1-[3-(trimethylammonio)propyl]quinolin-4(1H)-ylidene}prop-1-en-1-yl)-1,3-benzoxazol-3-ium diiodide, Yo-Pro-3(2+)-3-methyl-2-(3-{1-[3-(trimethylammonio)propyl]quinolin-4(1H)-ylidene}prop-1-en-1-yl)-1,3-benzoxazol-3-ium, YoYo-1-1,1'-{propane-1,3-diylbis[(dimethylazaniumdiyl)propane-3,1-diyl]}bis {4-[(3-methyl-1,3-benzoxazol-2(3H)-ylidene)methyl]quinolinium) tetraiodide, YoYo-1(4+)-1,1'-(propane-1,3-diylbis[(dimethylammonio)propane-3,1-diyl]}bis {4-[(3-methyl-1,3-benzoxazol-2(3H)-ylidene)methyl]quinolinium}, YoYo-3-1,1'-[3,7-bis(dimethyliminio)nonane-1,9-diyl]bis{4-[3-(3-methyl-1,3-benzoxazol-2(3H)-ylidene)prop-en-1-yl]quinolinium}tetraiodide, YoYo-3(4+)-1,1'-[3,7-bis(dimethyliminio)nonane-1,9-diyl]bis {4-[3-(3-methyl-1,3-benzoxazol-2(3H)-ylidene)prop-en-1-yl]quinolinium}, zinc octaethylporphyrin-[2,3,7,8,12,13,17,18-octaethylporphyrinato(2−)-κ$^4$,N$^{21}$,N$^{22}$,N$^{23}$,N$^{24}$]zinc, zinc phthalocyanine-[29H,31H-phthalocyaninato(2−)-κ$^4$,N$^{21}$,N$^{22}$,N$^{23}$,N$^{24}$]zinc, zinc tetramesitylporphyrin-[5,10,15,20-tetrakis(2,4,6-trimethylphenyl)porphyrinato(2−)-κ$^4$,N$^{21}$,N$^{22}$,N$^{23}$,N$^{24}$]zinc, and zinc tetraphenylporphyrin-[5,10,15,20-tetraphenylporphyrinato(2−)-κ$^4$,N$^{21}$,N$^{22}$,N$^{23}$,N$^{24}$]zinc.

In addition, the present invention discloses having a bodipy agent covalently linked to a tethering moiety and having two free amine moieties, wherein the amine moieties form a covalent link to a cytotoxic agent, such as an artemesin moiety.

Lymphoma cells expressing CD74 can import approximately $10^7$ molecules of an anti-CD74 mAb (LL1) per cell per day (Hansen et al. *Biochem J.* 320:293-300, 1996). Expression of CD74 and/or MIF was observed in a variety of malignant cells including most B-cell cancers (Burton et al. *Clin. Cancer Res.* 10:6606:6611, 2004; McClelland et al. *Am. J. Pathol.* 174:638-646, 2009; and Cutbert et al. *Eur. J. Cancer* 45:1654-1663, 2009).

Synthesis Example 1

This example illustrates synthesis of preferred teathering moiety product (2-hydroxy-4-[(5-methyl-2-oxo-1,3-benzoxazol-3(2H)-yl)methyl]phenoxy)acetic acid (compound 7). The last step of this synthesis covalently binds product {2-hydroxy-4-[(5-methyl-2-oxo-1,3-benzoxazol-3(2H)-yl) methyl]phenoxy}acetic acid (compound 7) to toxic agent doxorubicin.

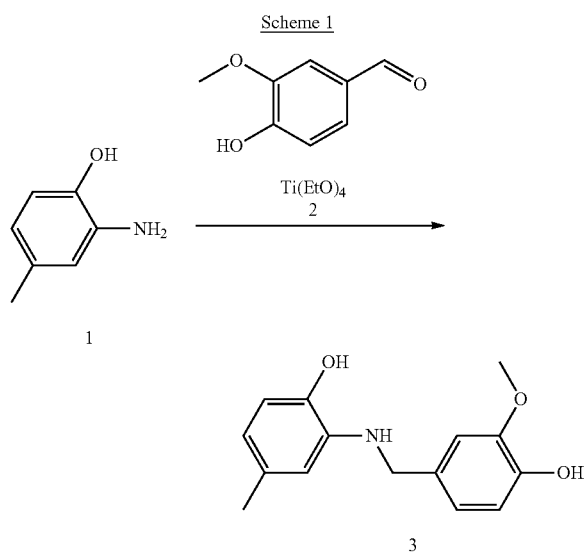

A solution of 20 g (162 mmol) of 2-amino-4-methylphenol (compound 1) and 20.4 g of vanillin (compound 2) (162 mmol) in 200 mL of EtOH was added Ti(OEt)$_4$ (92.2 g, 400 mmol) at 25° C. The reaction mixture was stirred at 25° C. for 2 hrs. The reaction was cooled to 0° C. and 20 g (526 mmol) of NaBH$_4$ was added in portions at 0° C. The reaction mixture was stirred for additional 3 hrs as 25° C.

The reaction mixture was diluted with 200 mL of H$_2$O and 200 mL of EtOH. The resulting precipitate was concentrated and concentrated to remove EtOH. Then, 200 mL of EtOAc was added, the mixture was filtered and solid was washed with EtOAc (100 mL*3). Filtrate was separated and the aqueous layer was extracted with EtOAc (100 mL*3). The combined organic layer was washed with brine (250 mL), dried over Na$_2$SO$_4$, filtered and concentrated to afford 30 g of 2-[(4-hydroxy-3-methoxybenzyl)amino]-4-methylphenol (compound 3) as brown oil (in about 70% purity), which was used for next step without further purification.

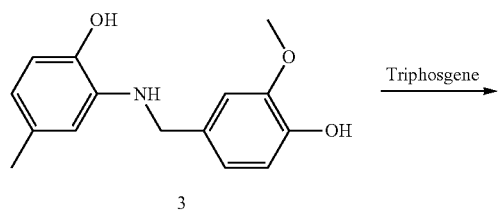

To a solution of compound 3 (30 g, 0.115 mol) in 300 mL of CH$_2$Cl$_2$ was added Et$_3$N (49 mL, 0.35 mol) at 0° C. The mixture was stirred at 0° C. for 15 min. Then a solution of triphosgene (11.44 g, 38.6 mmol) was added into above solution at 0° C. for 1 hr. After addition, the reaction was allowed to warm to room temperature and stirred for 15 hrs.

The reaction mixture was washed with st. NaHCO$_3$ aqueous (200 mL) and brine (200 mL), dried over MgSO$_4$, filtered and concentrated to afford 30 g of crude product as brown oil, which was used for next step without further purification.

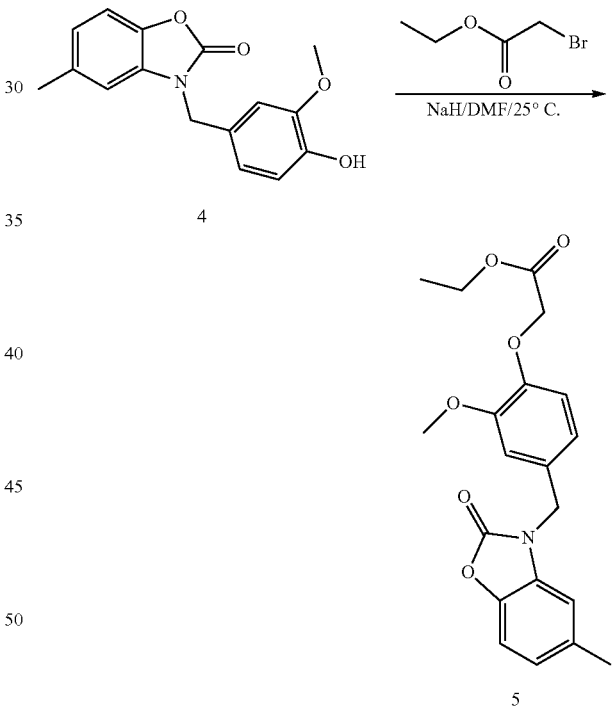

5.1 g (126 mmol) of NaH (60%) was added into a solution of 3-(4-hydroxy-3-methoxybenzyl)-5-methyl-1,3-benzoxazol-2(3H)-one (compound 4) (30 g crude, 105 mmol) and 21 g (126 mmol) of ethyl 2-bromoacetate in 800 mL of DMF at 0° C. The reaction mixture was allowed to warm to 25° C. and stirred for 15 hrs.

The reaction mixture was diluted with 1 L of EtOAc and 1 L of H$_2$O. The mixture was separated and aqueous layer was extracted with EtOAc (500 mL*3). The combined organic layers was washed with brine (1 L) and dried over Na$_2$SO$_4$, filtered and concentrated to afford 30 g of crude product as brown oil, which was purified by column chromatography (Elute:PE:EA=8:1 to PE:EA=2:1) to afford 10 g of pure product as yellow solid.

LC-MS: H12312-042-1 (M+23:393.8)

¹H NMR: H12312-042-3S (MeOD, 400 MHz) 7.045-7.117 (m, 2H); 6.873-6.941 (m, 4H); 4.949 (s, 2H); 4.665 (s, 2H); 4.179-4.215 (m, 2H); 3.820 (s, 3H); 2.326 (s, 3H); 1.205-1.402 (t, 3H);

Scheme 4

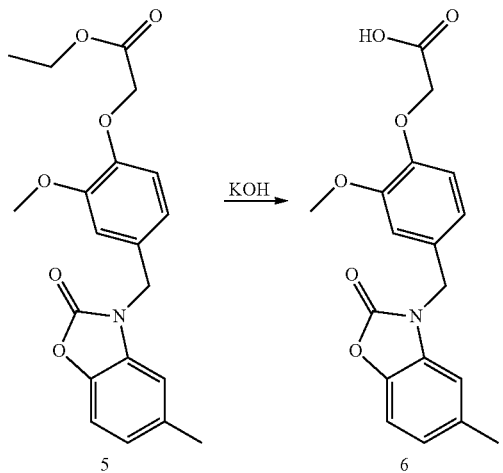

1 g (2.7 mmol) of ethyl(2-methoxy-4-[(5-methyl-2-oxo-1,3-benzoxazol-3(2H)-yl)methyl]phenoxy)acetate (compound 5) was dissolved in 20 mL of MeOH, following 20 mL of 2M NaOH aqueous was added. The reaction mixture was stirred at 25° C. for 15 hrs. The reaction mixture was concentrated to remove MeOH. Then 2N HCl was added in to aqueous to pH=2. The reaction mixture was extracted with EtOAc (200 mL*3). The combined organic layer was washed with brine (60 mL) and dried over $Na_2SO_4$, filtered and concentrated. The residue was solidified with TBME (100 mL). The resulting precipitate was filtered and solid was washed with TBME to afford 600 mg of compound 6 as brown solid, which was used for next step without further purification.

¹H NMR: H12312-042-2 (MeOD, 400 MHz) 7.005-7.075 (m, 2H); 6.875-6.989 (m, 4H); 4.674 (s, 2H); 4.410 (s, 2H); 3.857 (s, 3H); 2.221 (s, 3H);

Scheme 5

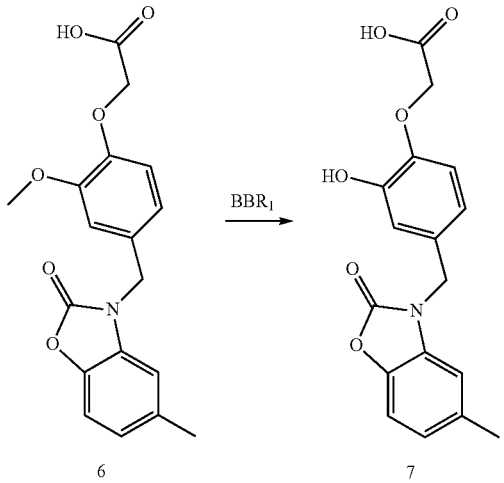

To a solution of {2-methoxy-4-[(5-methyl-2-oxo-1,3-benzoxazol-3(2H)-yl)methyl]phenoxy}acetic acid (compound 6) (600 mg, 1.75 mmol) in dichloromethane (6 mL) was added $BBr_3$ (0.88 g, 3.5 mmol) at −40° C. And then the mixture was stirred at room temperature overnight. LC-MS indicated the complete consumption of the starting material. The mixture was cooled to 0° C. and MeOH (10 mL) was added. The solvent was removed under reduced pressure. The residue was dissolved in water (20 mL) and quenched with saturated $NaHCO_3$ solution (20 mL). The mixture was extracted with ethyl acetate (25 mL*3). The organic layers were combined and dried over $MgSO_4$. The solvent was removed under reduce pressure to afford the desired product (2-hydroxy-4-[(5-methyl-2-oxo-1,3-benzoxazol-3(2H)-yl) methyl]phenoxy acetic acid (compound 7) (200 mg, yield 40%) as a light yellow solid. The crude product was used in the next step without purification.

Scheme 6

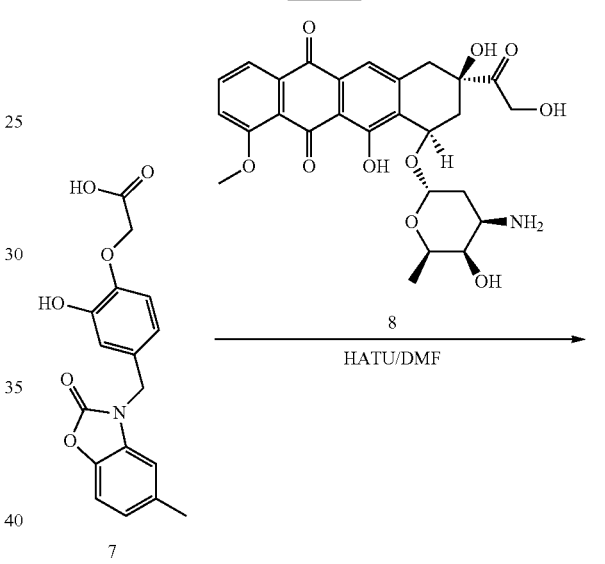

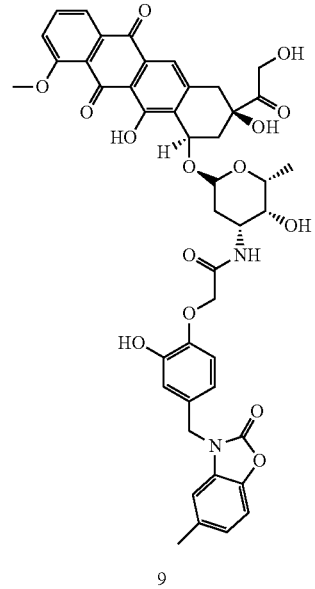

To a mixture of Compound 7 (1 eq), doxorubicin (compound 8) (1 eq) and DIEA (3 eq) in DMF was added HATU (1 eq) in one portion. The mixture was stirred at 25° C. for 2 h. The reaction mixture was purified by preparative HPLC to give the desired product amine tethered Doxorubicin/N-((2R,3R,4R,6R)-6-(((1R,3R)-3,12-DIHYDROXY-3-(2-HY-DROXYACETYL)-10-METHOXY-6,11-DIOXO-1,2,3,4,6,11-HEXAHYDROTETRACEN-1-YL)OXY)-3-HYDROXY-2-METHYLTETRAHYDRO-2H-PYRAN-4-YL)-2-(2-HYDROXY-4-((5-METHYL-2-OXOBENZO[D]OXAZOL-3(2H)-YL)METHYL)PHENOXY) ACETAMIDE (compound 9).

Synthesis Example 2

This example illustrates the covalent linkage of {2-hydroxy-4-[(5-methyl-2-oxo-1,3-benzoxazol-3(2H)-yl)methyl]phenoxy}acetic acid (compound 7) to artemisinyl propylamine (compound 10) to form teathered artemisinin.

washed with $CH_2Cl_2$. The filtrate and washings were combined, and the solvent was removed by Rotavap to yield the crude product. The product, tethered artemisinin 2-(2-hydroxy-4-((5-methyl-2-oxobenzo[d]oxazol-3(2H)-yl)methyl)phenoxy)-N-(3-((3R,5aS,6R,8aS,9R,10S,12R,12aR)-3,6,9-trimethyldecahydro-12H-3,12-epoxy[1,2]dioxepino[4,3-i]isochromen-10-yl)propyl)acetamide (compound 11) was further purified by silica gel chromatography, using $CH_2Cl_2$-methanol as an eluent. Yield 0.5 gram (75%). White powder, MALDI-MS: 635 [M+H]$^+$.

Synthesis Example 3

This example illustrates the covalent linkage of 2-{2-hydroxy-4-[(5-methyl-2-oxo-1,3-benzoxazol-3(2H)-yl)methyl]phenoxy}acetohydrazide (compound 17) to doxorubicin to form Hydrzone-tethered doxorubicin (compound 18).

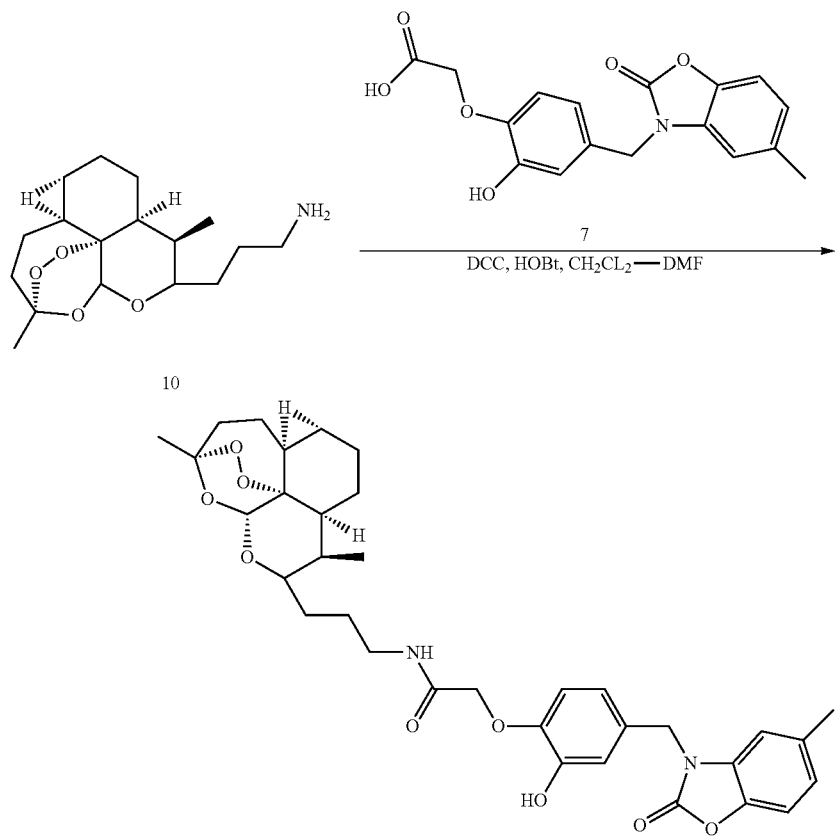

Artemisinyl propylamine (compound 10) (0.32 gram, 1 mmole), {2-hydroxy-4-[(5-methyl-2-oxo-1,3-benzoxazol-3(2H)-yl)methyl]phenoxy}acetic acid (Compound 7), (0.33 gram, 1 mmole) and HOBt-H$_2$O (0.30 gram, 2 mmole) were dissolved in 10 mL of $CH_2Cl_2$-DMF, 1:1 (v/v) mixture. The mixture was cooled to 0° C. in ice-bath, and dicyclohexylcarbodiimide (DCC, 0.22 gram, 1.1 mmole) was added with stirring. The mixture was kept stirring at 0° C. for 2 hr and then at room temperature for overnight. White precipitates, dicyclohexylurea, were removed by suction filtration, and

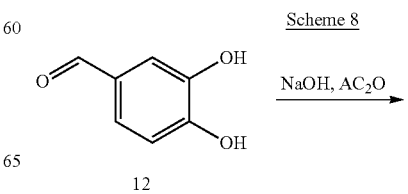

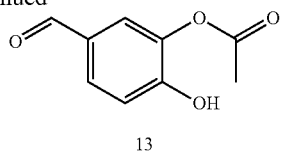

13

3,4-Dihydroxybenzaldehyde (compound 12) (20 g, 152 mmol) was suspended in 200 mL of THF and cooled to 0° C. NaOH solution (12 g in 150 mL of $H_2O$) was added dropwise, followed by a dropwise addition of $Ac_2O$ (18 g, 176 mmol). The reaction mixture was stirred at room temperature for 20 mins then it was diluted with EtOAc (200 mL). The reaction mixture was then acidified to pH=6 with 1N HCl and the organic layer were washed with water. After drying and filtration, 31 g crude product 5-formyl-2-hydroxyphenyl acetate (compound 13) was used in the next step without further purification.

Scheme 9

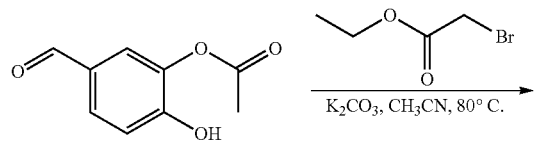

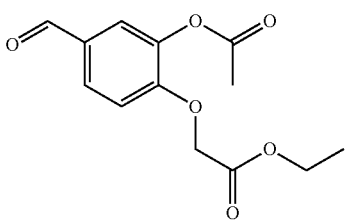

14

The mixture of compound 13 (31 g crude), ethyl 2-bromoacetate (60 g, 359 mmol) and $K_2CO_3$ (42 g, 300 mmol) in $CH_3CN$ (500 mL) was stirred at reflux for 18 h. The reaction mixture was filtered and concentrated. The residue was purified by chromatography on silica gel (petroleum ether to petroleum ether/EtOAc=6/1 as the eluent) to obtain 12 g ethyl[2-(acetyloxy)-4-formylphenoxy]acetate, (compound 14).

$^1$H NMR: H14220-027-1 (CD3CN 400 MHz) 9.853 (s, 1H), 7.759-7.786 (dd, J=2 Hz, 8.4 Hz, 1H), 7.607-7.612 (d, J=2 Hz, 1H), 7.106-7.127 (d, J=8.4 Hz, 1H), 7.766 (s, 2H), 4.191-4.244 (q, 2H), 2.288 (s, 3H), 1.234-1.270 (t, 3H).

Scheme 10

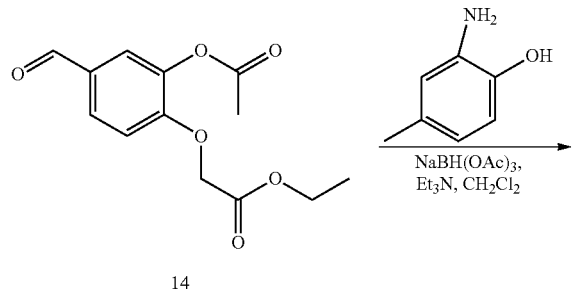

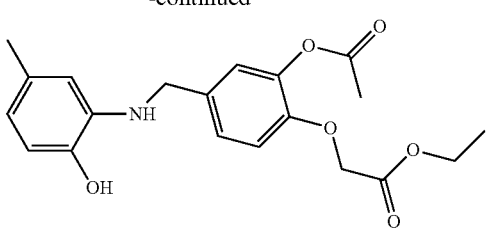

15

The mixture of compound 14 (12 g, 45 mmol), 2-amino-4-methylphenol (5.54 g, 45 mmol), and $Et_3N$ (13.66 g, 135 mmol) in $CH_2Cl_2$ was stirred at 25° C. for 1 h. Then $NaBH(OAc)_3$ (28.6 g, 135 mmol) was added. The resulting mixture was stirred at 25° C. for 18 h. The reaction was diluted with $CH_2Cl_2$ (200 mL), water (400 mL) and $Et_3N$ (40 mL). The organic layer was washed with brine, dried over $MgSO_4$, filtered and concentrated to obtain 19 g crude product ethyl[2-(acetyloxy)-4-{[(2-hydroxy-5-methylphenyl)amino]methyl}phenoxy]acetate (compound 15) which was used in the next step without further purification.

Scheme 11

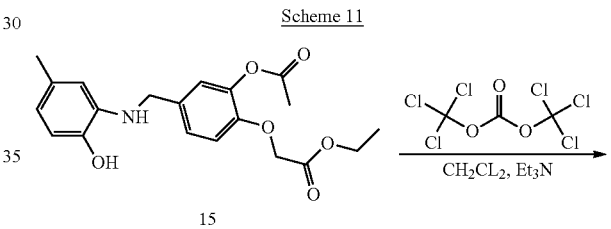

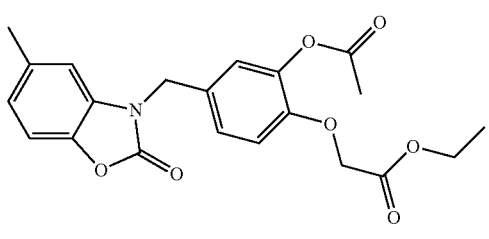

16

To a solution of compound 15 (19 g, crude) in 200 mL of dichloromethane was added $Et_3N$ (15.2 g, 150 mmol), followed by triphosgene (4.98 g, 16.7 mmol) in 50 mL of dichloromethane at 0° C. The resulting mixture was stirred at 25° C. for 18 h. The reaction was diluted with water (400 mL) and extracted with dichloromethane. The combined organic layers were concentrated. The residue was suspended in 50 0 mL (EtOAc/PE=1/10:v/v). The solid was collected by filtration and dried under vacuum to obtain 5 g ethyl {2-(acetyloxy)-4-[(5-methyl-2-oxo-1,3-benzoxazol-3 (2H)-yl)methyl]phenoxy}acetate, (compound 16). LCMS: 14220-029-1E (94.85%, M+23: 421.8)

Scheme 12

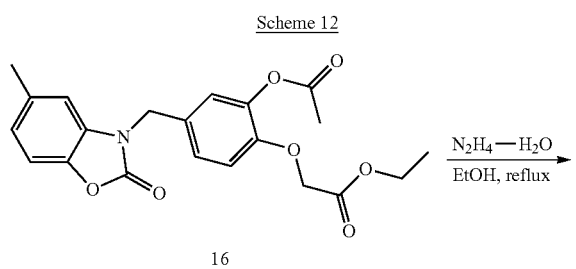

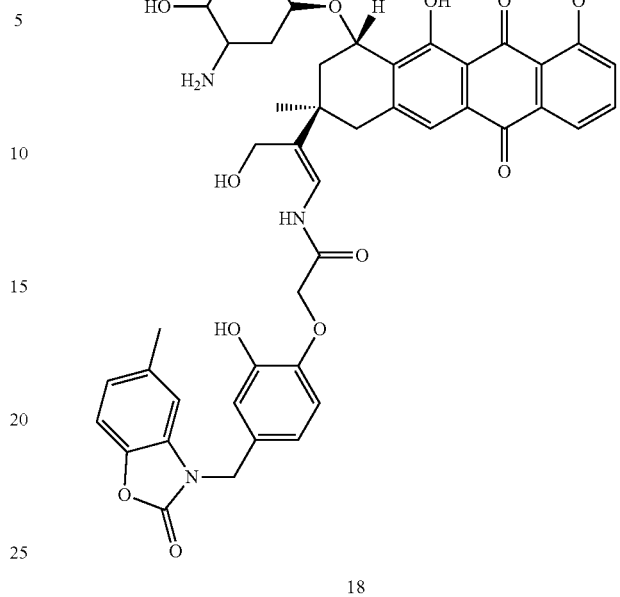

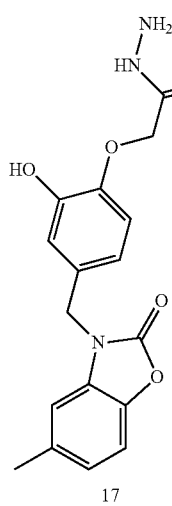

N$_2$H$_4$—H$_2$O (50 mL, 85%) was added to a mixture of compound 16 in 500 mL of EtOH. The reaction mixture was stirred at reflux for 8 h. Solid was collected and dried under vacuum to obtain 3 g 2-{2-hydroxy-4-[(5-methyl-2-oxo-1,3-benzoxazol-3(2H)-yl)methyl]phenoxy}acetohydrazide (compound 17).

Scheme 13

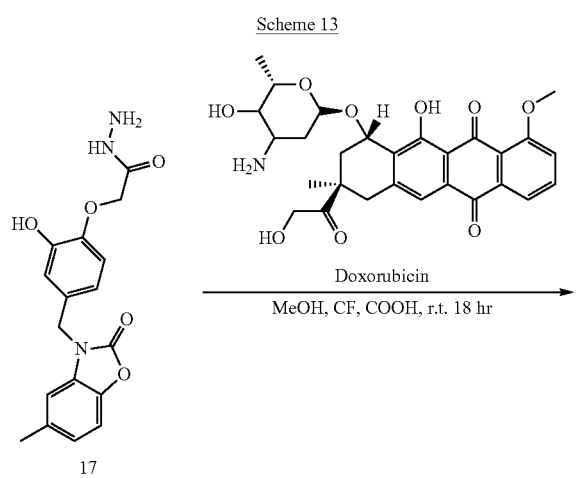

MeOH (500 mL) was bubbled with N$_2$ flow for 30 mins. Then doxorubicin (500 mg, 862 μmol) and compound 17 (444 mg, 1.29 mmol) were added under N$_2$. CF$_3$COOH (0.2 mL) was added. The resulting mixture was stirred at r.t. for 18 h under N$_2$. The reaction mixture was concentrated to about 180 mL, and CH$_3$CN (500 mL) was added. After cooling, the solid was filtrated off. The mother liquid was concentrated to about 50 mL, CH$_3$CN (200 mL) was added. The red solid was purified by HPLC. After lyophilization, 200 mg of Hydrzone-tethered doxorubicin RJS009_1 (compound 18) was obtained.

The analysis of Hydrzone-tethered Doxorubicin RJS009_1 (compound 18) was by preparative HPLC method: Column: YMC 150*30 mm, 5 μm; MPA: H$_2$O (0.08% NH$_4$HCO$_3$, w/w); MPB: CH$_3$CN; 39-49% B, 14 min; 35 mL/Min; HPLC condition for the analysis: Mobile Phase: 20 mmol NH$_3$CH$_2$COOH in water (solvent A) and acetonitrile (solvent B), using the elution gradient 10%-80% (solvent B) over 10 minutes and holding at 80% for 5 minutes at a flow rate of 1.5 ml/minutes; Column: YMC-pack ODS-A 150*4.6 mm, 5 μm. HPLC: 14220-040-1a (96.266%); MS: (M+1: 869.28) $^1$H NMR: H14220-040-1A (DMSO 400 MHz) 7.828-7.915 (m, 2H), 7.624-7.646 (d, J=8.8 Hz, 1H), 7.202-7.222 (d, J=8 Hz, 1H), 6.982-7.038 (d, J=22.4 Hz, 1H), 6.636-6.927 (m, 3H), 6.306-6.516 (m, 1H), 4.391-5.510 (m, 8H), 3.939-4.064 (m, 4H), 2.676-3.009 (m, 3H), 2.116-2.333 (m, 5H), 1.498-1.645 (m, 2H), 1.139-1.154 (m, 3H).

Synthesis Example 4

This example illustrates the covalent linkage of {2-hydroxy-4-[(5-methyl-2-oxo-1,3-benzoxazol-3(2H)-yl) methyl]phenoxy}acetic acid (compound 7) to Doxorubicin using a Amino-PEG4-acid linker (BroadPharm, San Diego, Calif.).

Scheme 14

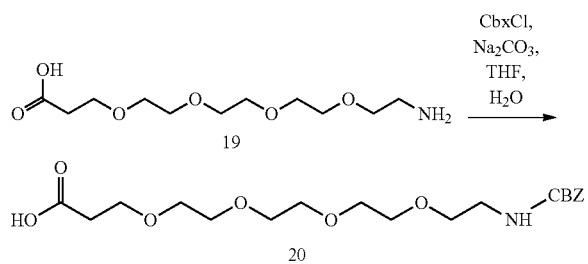

To a solution of 1-amino-3,6,9,12-tetraoxapentadecan-15-oic acid (Compound 19) (320 mg 1.2 mmol) in THF (10 mL) CbzCl was added (248 mg, 1.46 mmol) and saturated aqueous $Na_2CO_3$ (5 mL). The mixture was stirred at 17° C. for 15 hrs. The mixture was then diluted with water and acidified to pH=2. The mixture was extracted with $CH_2Cl_2$ (40 mL). The organic layer was washed with brine, dried over $MgSO_4$, filtered and concentrated to obtain 3-oxo-1-phenyl-2,7,10,13,16-pentaoxa-4-azanonadecan-19-oic acid (compound 20) (380 mg).

Scheme 15

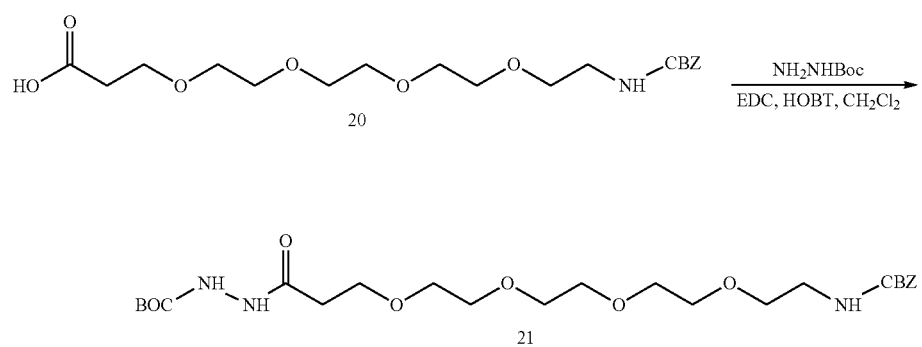

To a solution of compound 20 (380 mg, 951 umol) in DCM (10 mL), EDC (188.5 mg, 1.42 mmol) HOBT (128.5 mg, 0.95 mmol), $NH_2NHBoc$ (271 mg, 1.42 mmol) and DIEA (368 mg, 2.85 mmol) were added. The mixture was stirred at 17° C. for 15 hrs. The mixture was washed with saturated $NaHCO_3$, dried over $MgSO_4$, filtered and concentrated. The residue was purified by flash chromatography on silica gel to obtain 19-benzyl 1-(tert-butyl) 18-amino-4-oxo-7,10,13,16-tetraoxa-2,3-diazanonadecanedioate (compound 21) (260 mg).

Scheme 16

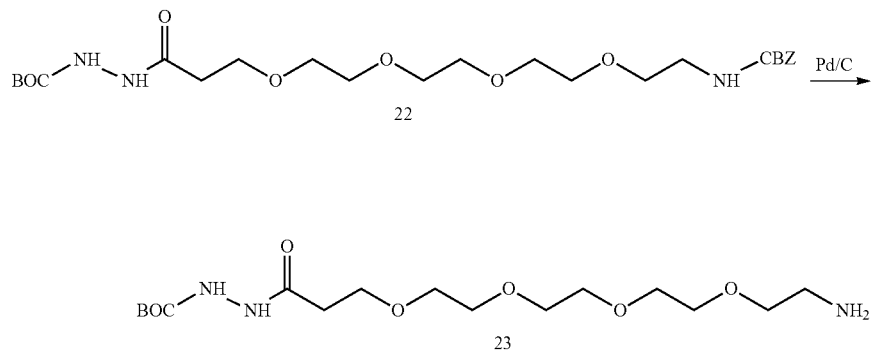

To a solution of 19-benzyl 1-(tert-butyl) 18-amino-4-oxo-7,10,13,16-tetraoxa-2,3-diazanonadecanedioate (compound 22) (100 mg 194 umol) in MeOH (10 mL) 20 mg of Pd/C was added. The mixture was stirred at 20*C for 15 hrs under H2 (40 Psi). The mixture was filtered and concentrated to obtain tert-butyl 18-amino-4-oxo-7,10,13,16-tetraoxa-2,3-diazaoctadecanoate (compound 23) (50 mg).

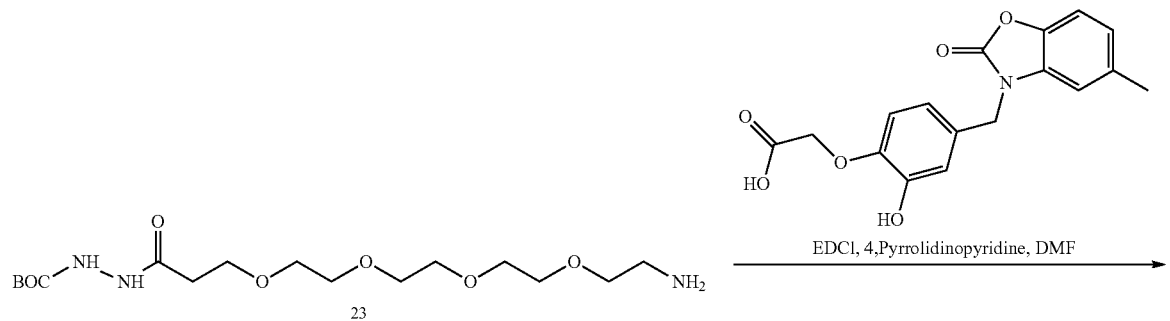
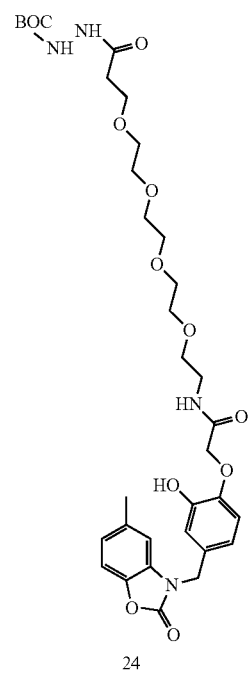

Compound 23—tert-butyl 18-amino-4-oxo-7,10,13,16-tetraoxa-2,3-diazaoctadecanoate; Compound 24—tert-butyl 21-(2-hydroxy-4-((5-methyl-2-oxobenzo[d]oxazol-3(2H)-yl)methyl)phenoxy)-4,20-dioxo-7,10,13,16-tetraoxa-2,3,19-triazahenicosanoate

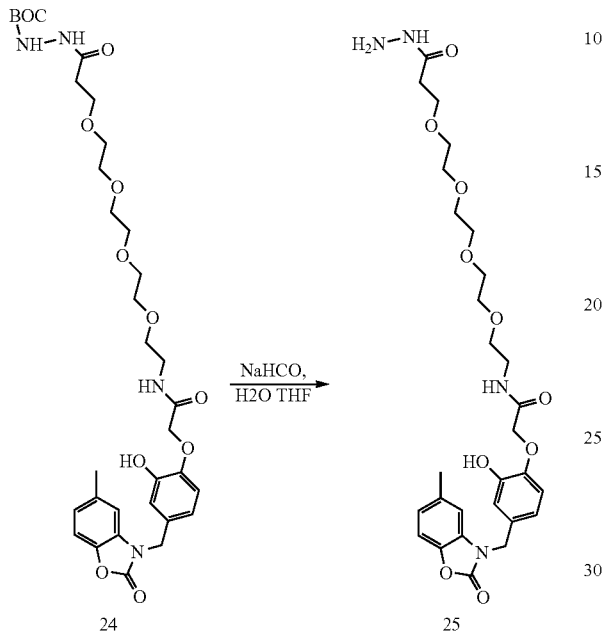

Compound 24—tert-butyl 21-(2-hydroxy-4-((5-methyl-2-oxobenzo[d]oxazol-3(2H)-yl)methyl)phenoxy)-4,20-dioxo-7,10,13,16-tetraoxa-2,3,19-triazahenicosanoate. Compound 25—N-(15-hydrazinyl-15-oxo-3,6,9,12-tetraoxapentadecyl)-2-(2-hydroxy-4-((5-methyl-2-oxobenzo[d]oxazol-3(2H)-yl)methyl)phenoxy)acetamide Scheme 18

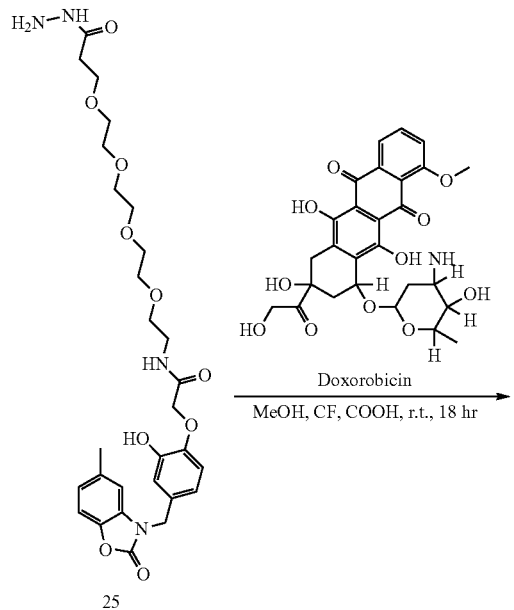

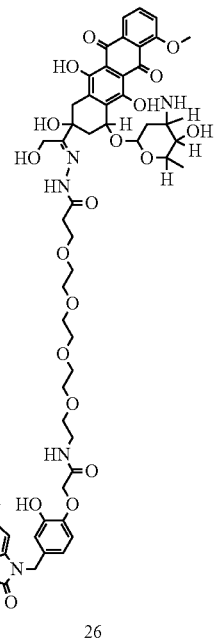

Compound 25—N-(15-hydrazinyl-15-oxo-3,6,9,12-tetraoxapentadecyl)-2-(2-hydroxy-4-((5-methyl-2-oxobenzo[d]oxazol-3(2H)-yl)methyl)phenoxy)acetamide Compound 26—N-((E)-2-((2S,4S)-4-(((4S,5S,6S)-4-amino-5-hydroxy-6-methyltetrahydro-2H-pyran-2-yl)oxy)-2,5,12-trihydroxy-7-methoxy-6,11-dioxo-1,2,3,4,6,11-hexahydrotetracen-2-yl)-1-hydroxy-5-oxo-8,11,14,17-tetraoxa-3,4-diazanonadec-2-en-19-yl)-2-(2-hydroxy-4-((5-methyl-2-oxobenzo[d]oxazol-3(2H)-yl)methyl)phenoxy)acetamide Scheme 19

MeOH (500 mL) is bubbled with $N_2$ flow for 30 mins. Then doxorubicin and N-(15-hydrazinyl-15-oxo-3,6,9,12-tetraoxapentadecyl)-2-(2-hydroxy-4-((5-methyl-2-oxobenzo[d]oxazol-3(2H)-yl)methyl)phenoxy)acetamide (compound 25) is added under $N_2$, with $CF_3COOH$. The resulting mixture is bestirred at r.t. for 18 h under $N_2$ and concentrated to about 180 mL. $CH_3CN$ is added. After cooling, the solid is filtrated off and the mother liquid is concentrated to about 50 mL, $CH_3CN$ (200 mL) is added. The red solid is purified by HPLC to obtain N-((E)-2-((2S,4S)-4-(((4S,5 S,6S)-4-amino-5-hydroxy-6-methyltetrahydro-2H-pyran-2-yl)oxy)-2,5,12-trihydroxy-7-methoxy-6,11-dioxo-1,2,3,4,6,11-hexahydrotetracen-2-yl)-1-hydroxy-5-oxo-8,11,14,17-tetraoxa-3,4-diazanonadec-2-en-19-yl)-2-(2-hydroxy-4-((5-methyl-2-oxobenzo[d]oxazol-3(2H)-yl)methyl)phenoxy)acetamide (Compound 26).

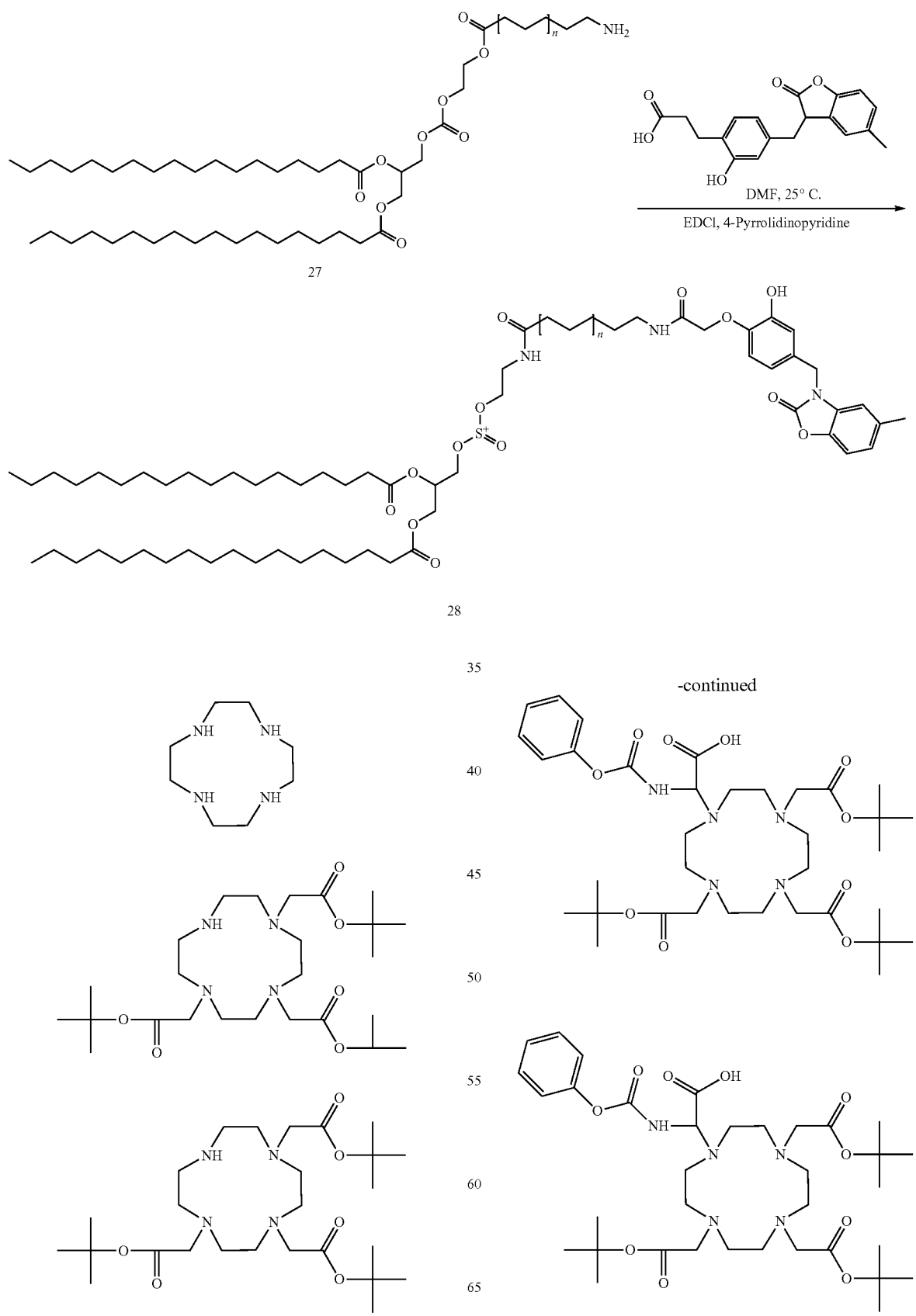

99
-continued
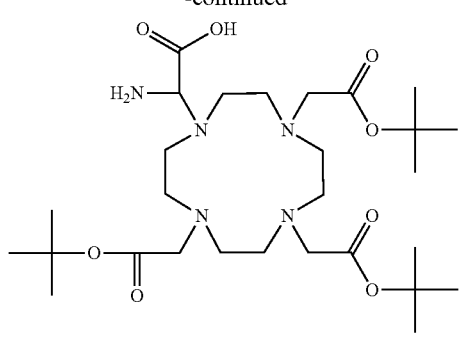
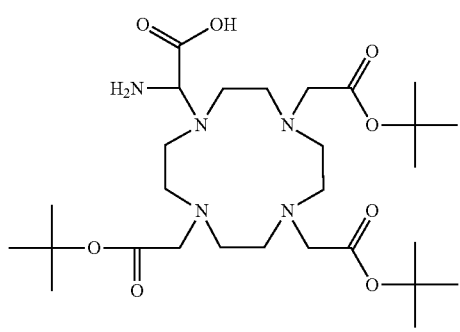
100
-continued
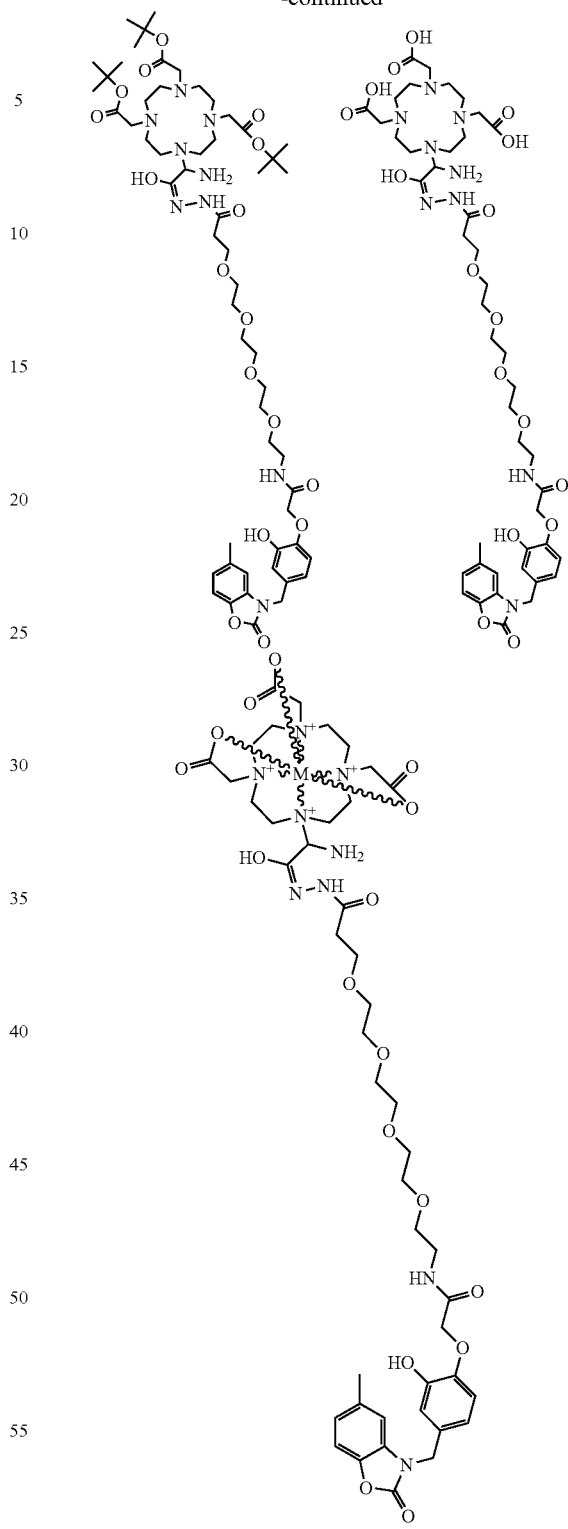
Synthesis of α-amino-DOTA and an affinity-tethered-DOTA MRI contrast agent. (a) tert-butylbromoacetate, K₂CO₃ (6 eq.), acetonitrile, 70° C., 6 hrs, 83%; (b) CBZ-Gly(Br)-OMe, K₂CO₃ (6 eq.), acetonitrile, 70° C., 6 hrs, 83%; (c) H₂, 10-Pd/C, ethanol; 2 hrs, quantitative; (d) Fmoc-Cl, zinc dust, acetonitrile, 87%; (e) 50% TFA in CH₂Cl₂, quantitative; (f) (i) Wang resin, HBTU (4 eq.), HOBt (1 eq.), DIEA (10 eq.), NMP, rt, overnight; (ii) 50% tert-BuOH in CH₂Cl₂, 70%; (g) (i) 20% piperidine, NMP; (ii) SPPS of Z-Gly-Gly-Arg(pbf) following standard Fmoc-chemistry (iii) 95% TFA, CH₂Cl₂, 4 hrs; (iv) Tm-triflate, acetonitrile, 50° C., overnight.

Scheme 21

1,4,7,10-TetraaZaCyClOdOdeCaUe N,N',N",N"'-tetraacetic acid (DOTA) forms kinetically stable chelates With metal ions of lanthanide series (such as yttrium and gadolinium) of the periodic table. DOTA N-hydroxysulfosuccinimide ester is prepared following a known procedure (Lewis et al., *Bioconjugate Chem.,* 5: 565-576, 1994), by mixing 60 mg (128 Mmol) of trisodium DOTA and 27.7 mg. (28 Mmol) of N-hydroxysulfosuccinimide, in 0.96 ml of water, and incubating this solution With 49 #1 of a freshly prepared solution of 'EDC' (50 mg/rnl) at 4° C. for 30 min. 1 ml of this solution. Contains 12.68 yrnol (theoretical) of the mono-activated DOTA sulfosuccinirnide.

An excess of this reagent is reacted with any of the arnine-deprotected biotinylating reagent shown in Table 1, and stirred at 4° C. for a period of 18-24 hours. The biotinylated DOTA product is purified on a reverse phase preparative HPLC Column using acetonitrile-water gradient-elution at a HOW rate of 1 rnl/rnin and monitoring the eluent with a refractive indeX detector. The purified material is analyzed by NMR spectroscopy and mass spectrometry.

-continued

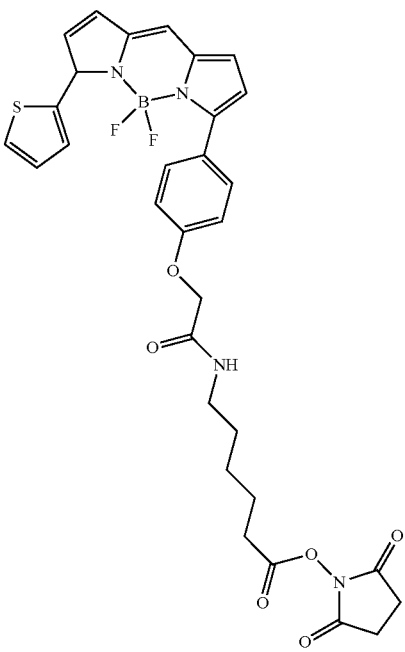

Scheme 22

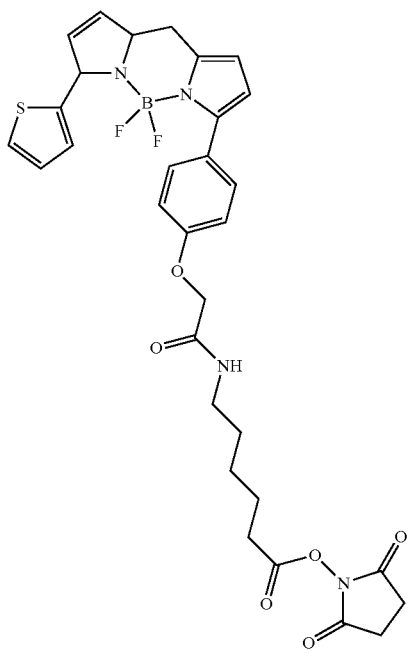

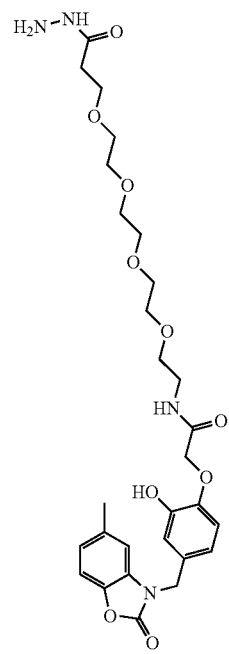

103
-continued
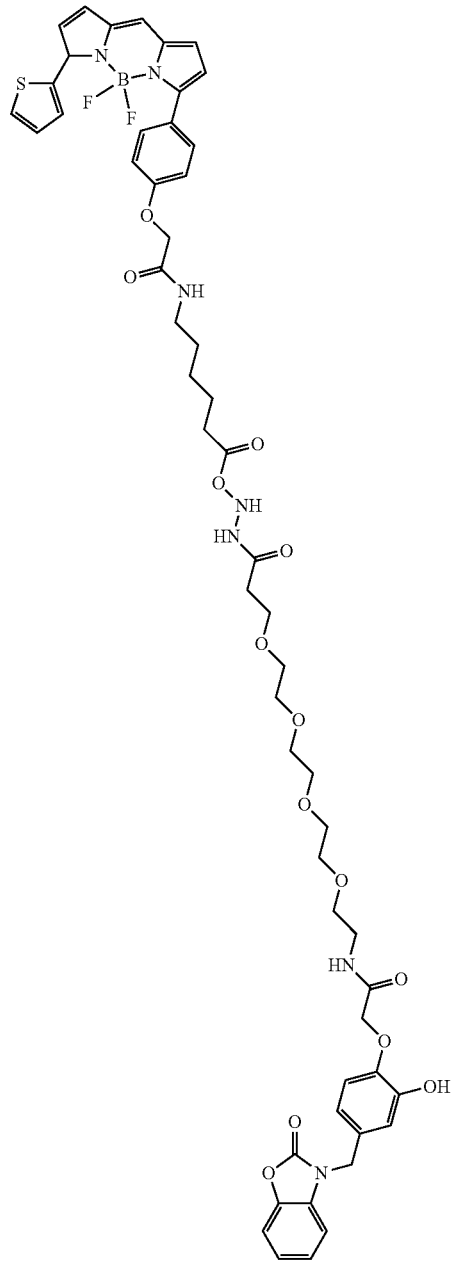
104
-continued
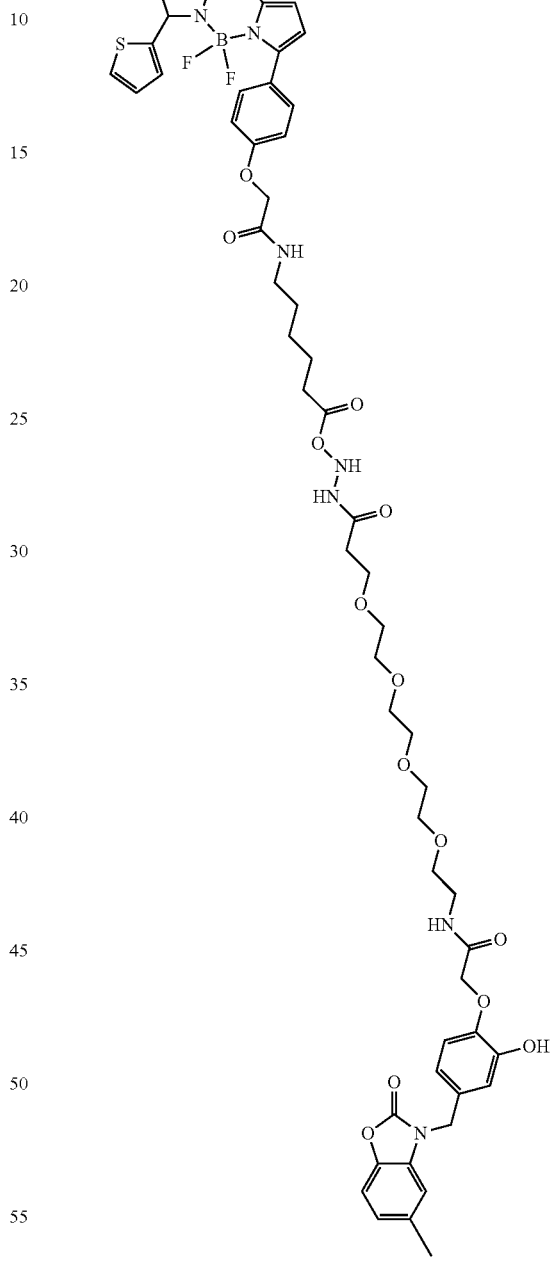

Scheme 22

Synthesis Example 3

Synthesis of RJS012_1

Final Structure—

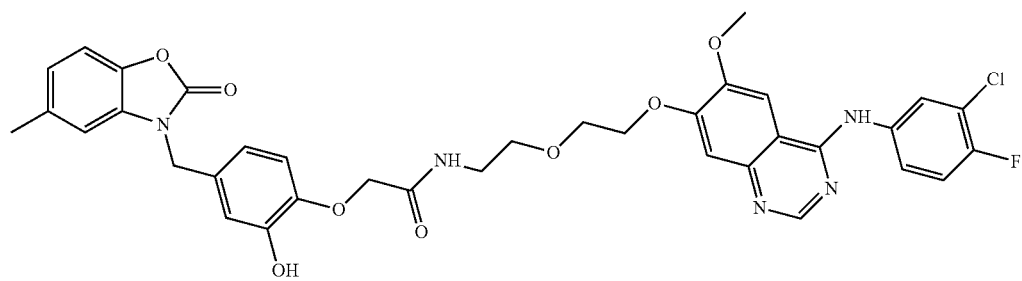 [SMILES: COc1cc2c(Nc3ccc(F)c(Cl)c3)ncnc2cc1OCCOCCNC(=O)COc1ccc(Cn2c(=O)oc3ccc(C)cc32)cc1O]

Synthesis—

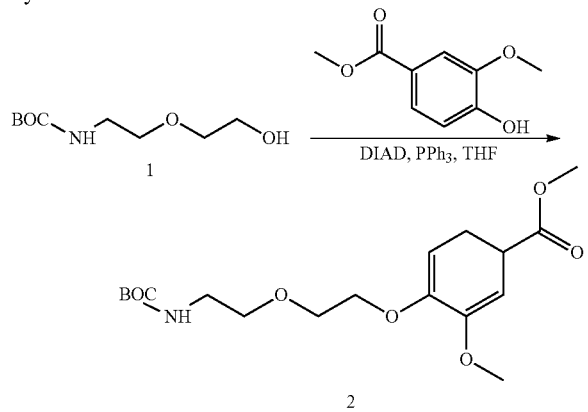

To a solution of Compound 1 (2 g, 9.74 mmol), methyl 4-hydroxy-3-methoxybenzoate (1.95 g, 10.72 mmol) and PPh₃ (3.07 g, 11.69 mmol) in 30 mL of THF was added DIAD (2.36 g, 11.69 mmol) dropwise at 0° C. under N₂. The mixture was stirred overnight and isolated with NaHCO₃ (50 mL) and EtOAc (50 mL), the aqueous layer was extracted with EtOAc (2*50 mL). The combined organic layer was washed with brine (2*50 mL), dried over MgSO₄ and concentrated, the residue was purified by column (Petroleum Ether:EtOAc=2:1) to give Compound 2 as white solid.

2. Synthesis of Compound 3:

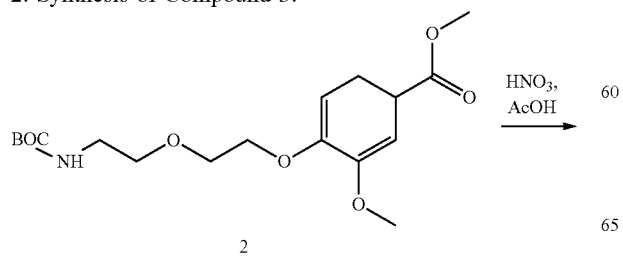

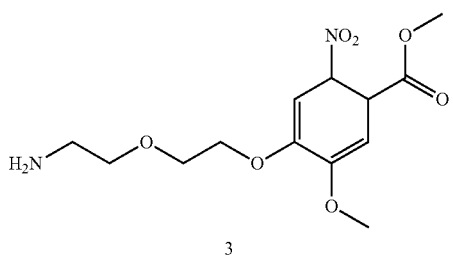

Compound 2 (2.1 g, 5.68 mmol) in 10 mL of AcOH was added HNO₃ (3.58 g, 56.8 mmol) dropwaise at 20° C. and stirred for 3 hrs. The mixture was quenched by adding in portions to ice water (30 mL). The resulting mixture was basified with 1M NaOH to pH=10 and extracted with EtOAc (3*40 mL). The combined organic layer was dried and concentrated. The residue was used to next step without purification.

3. Synthesis of Compound 4:

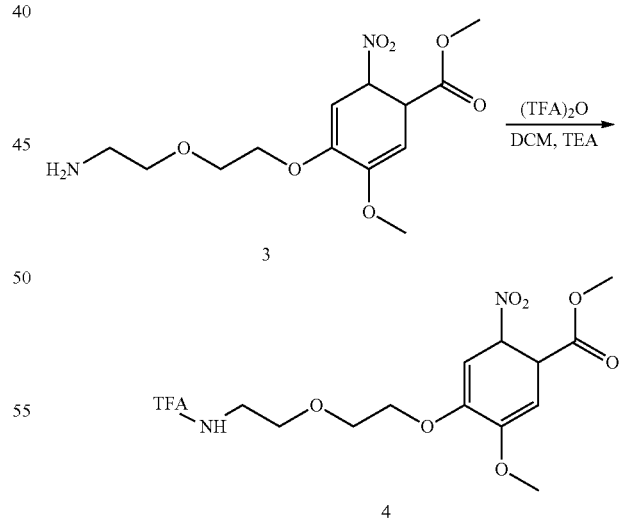

To a solution of Compound 3 (1.9 g crude) in 20 mL of dry CH₂Cl₁₂ was added Et₃N (2.45 g, 24.18 mmol). To the above solution was added TFAA (2.54 mg, 12.09 mmol) dropwise at 0° C. and stirred for 2 hrs. The mixture was concentrated and the residue was purified by column (Petroleum Ether:EtOAc=2:1) to give compound 4 as oil (1.2 g).

4. Synthesis of Compound 5:

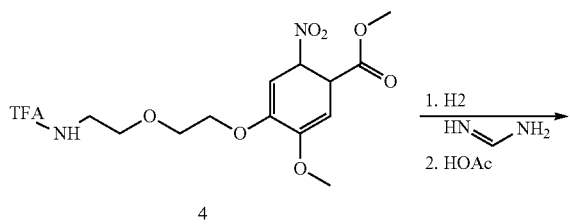

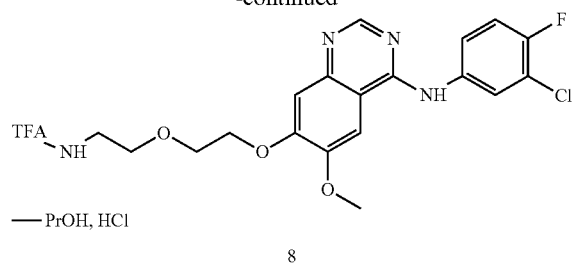

To a solution of compound 5 (1 g, 2.66 mmol) and DMF (1 drop) in 30 mL of CHCl₃ was added (COCl)₂ (676 mg, 5.33 mmol) drop wise and stirred at 80° C. for 3 hrs. The mixture was concentrated. To the residue was added i-PrOH (30 mL) and compound 7 (739.4 mg, 5.08 mmol). To the above mixture was added HCl (1 mL, 12 M) and refluxed for 2 hrs. The residue was isolated with NaHCO₃ (50 mL) and CHCl₃ (90 mL). The organic layer was washed with brine (50 mL), dried over MgSO₄ and concentrated. The residue was purified by column (Petroleum ether:EtOAc=1:3) to give compound 8 as oil (600 mg).

6. Synthesis of Compound 9:

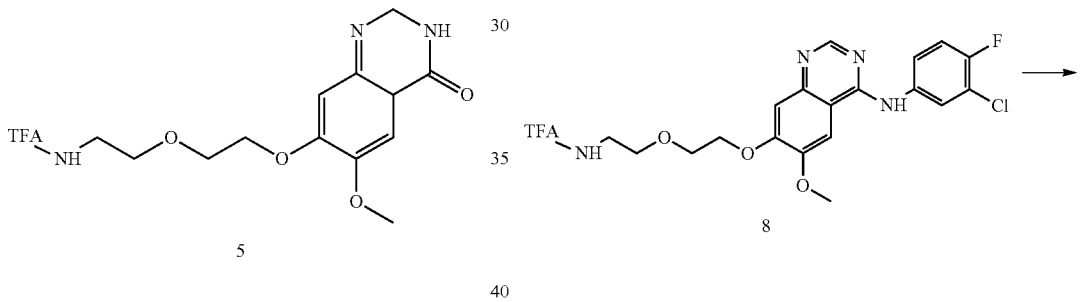

A mixture of compound 4 (1.2 g, 2.92 mmol) and Pd/C (250 mg) in 50 mL of MeOH was stirred at r.t. under 15 psi of H₂ for 3 hrs. The mixture was filtered. To the filtrate, formimidamide acetate was added (3.01 g, 28.92 mmol) and stirred at 90° C. for 3 hrs. The mixture was concentrated, the residue was washed with H₂O (100 mL) to give compound 5 as solid (1 g).

5. Synthesis of Compound 8:

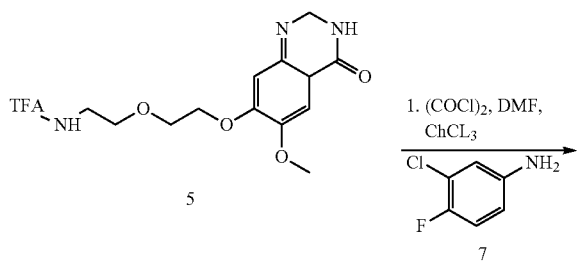

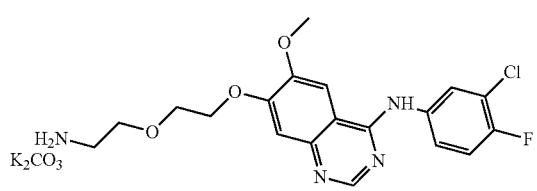

To a solution of compound 8 (30 mg, 59.66 umol) in 1 mL of MeOH was added K₂CO₃ (41.2 mg, 298.3 umol). The mixture was stirred at 80° C. for 6 hrs. The mixture was isolated with EtOAc (10 mL) and H₂O (10 mL). The aqueous layer was extracted with EtOAc (2*10 mL). The combined organic layer was washed with brine (15 mL), dried over MgSO₄ and concentrated to give compound 9 as a solid.

7. Synthesis of RJS012_1:
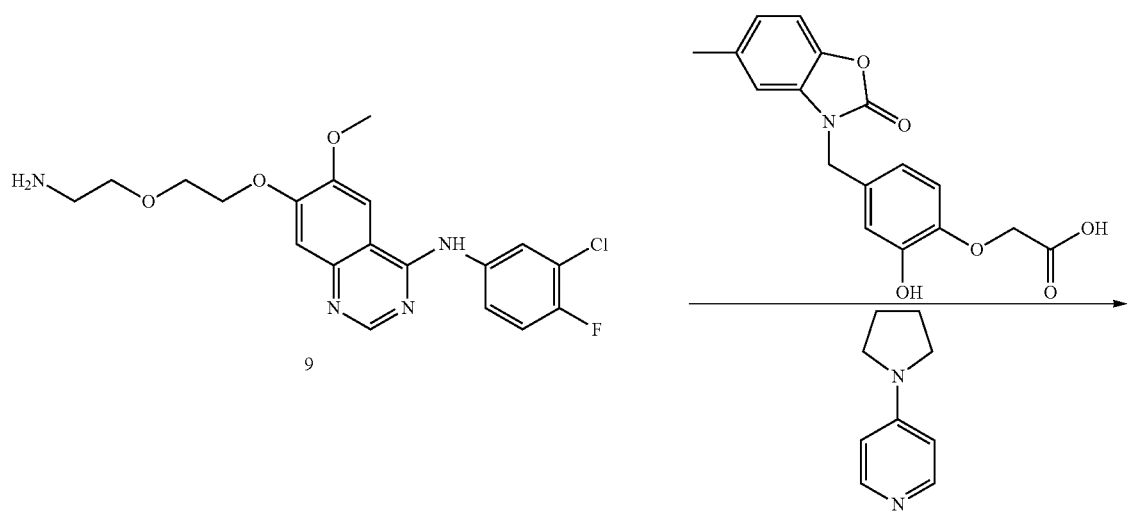
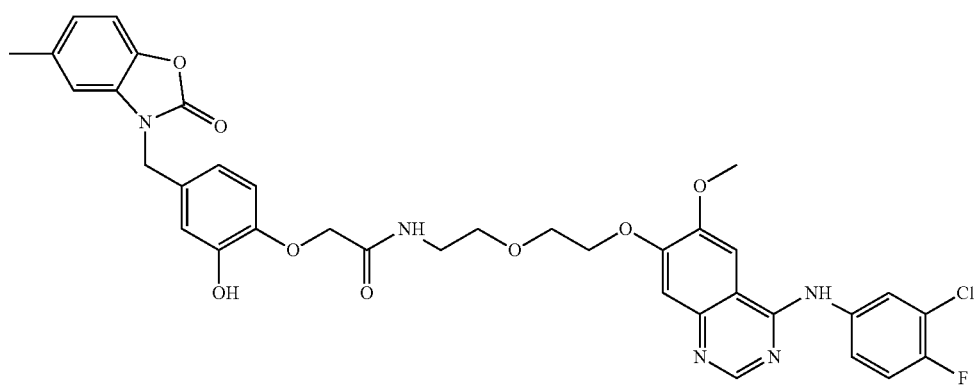
To a solution of compound 9 (110 mg, 270.38 umol), compound 11 (133.55 mg, 405.57 umol) and 4-(pyrrolidin-1-yl)pyridine (80.14 mg, 540.76 umol) in 20 mL of DMF was added EDC HCl (103.66 mg, 540.76 umol). The mixture was stirred overnight and concentrated. The residue was purified by column (EtOAc:MeOH=20:1) to give product as solid. Totally 110 mg was obtained.
Synthesis of RJS012_1
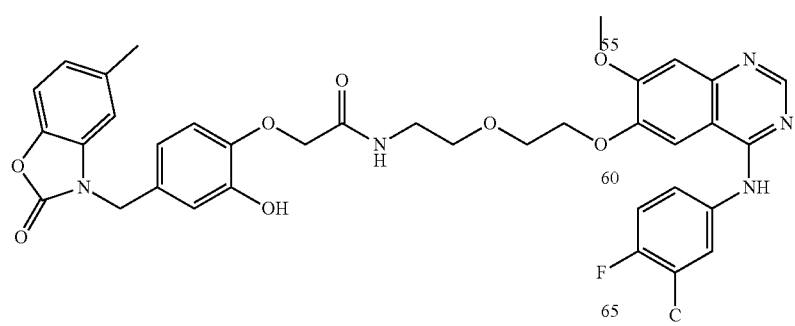 [SMILES: COc1cc2ncnc(Nc3ccc(F)c(C)c3)c2cc1OCCOCCNC(=O)COc1ccc(Cn2c(=O)oc3ccc(C)cc32)cc1O]

Synthesis of RJS012_3
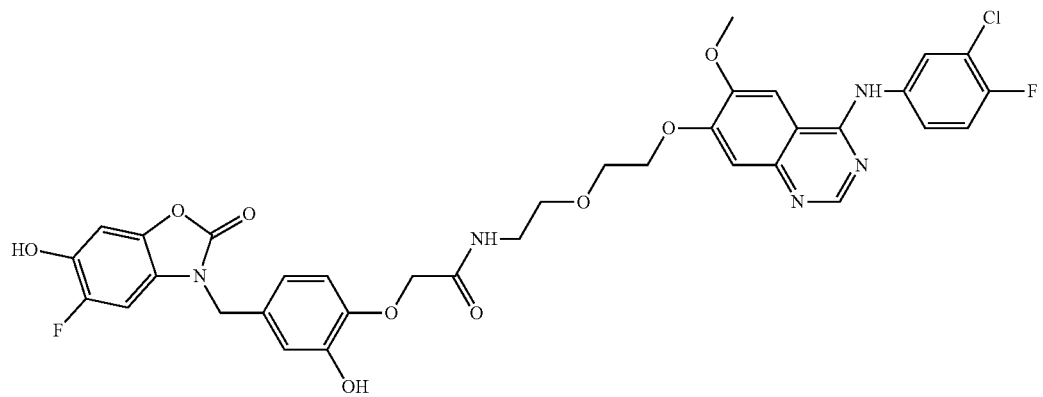 [SMILES: COc1cc2c(Nc3ccc(F)c(Cl)c3)ncnc2cc1OCCOCCNC(=O)COc1ccc(Cn2c(=O)oc3cc(O)c(F)cc32)cc1O]
Synthesis of RJS012_3
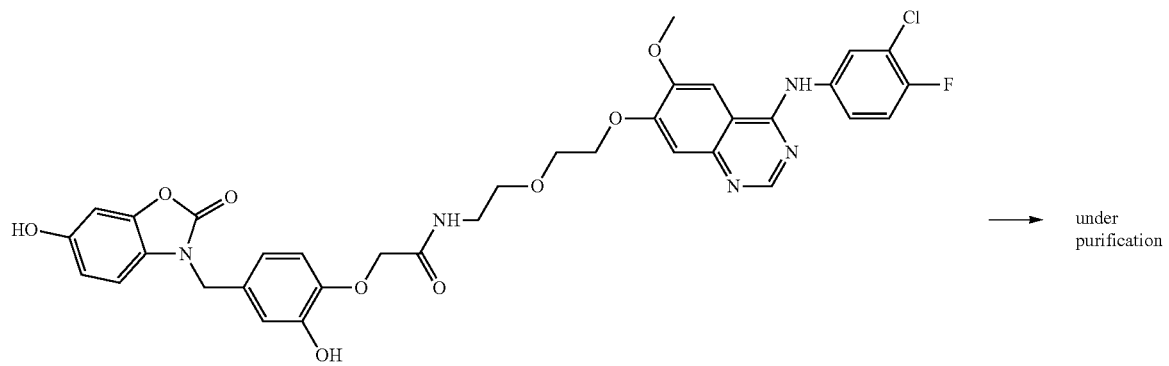
RJS012_3
→ under purification
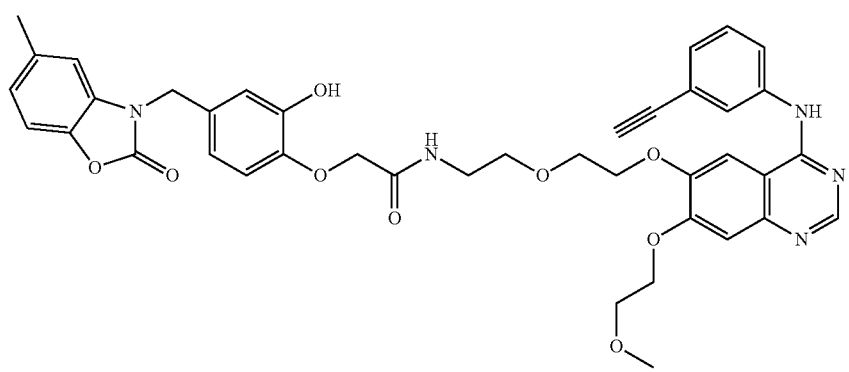
RJS013_1

Synthesis of RJS012_2 (T-Tarceva)

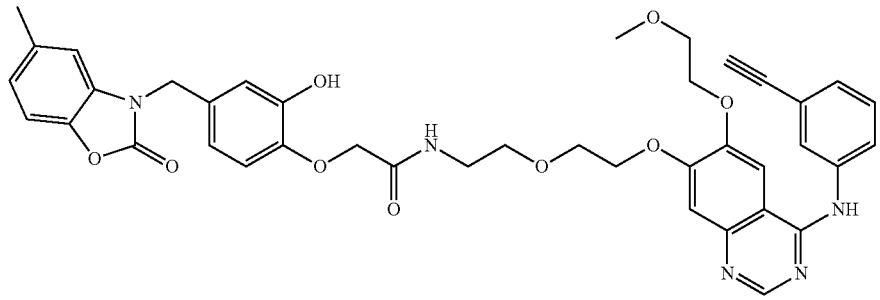 [SMILES: C#Cc1cccc(Nc2ncnc3cc(OCCOCCNC(=O)COc4ccc(Cn5c(=O)oc6ccc(C)cc65)cc4O)c(OCCOC)cc23)c1]
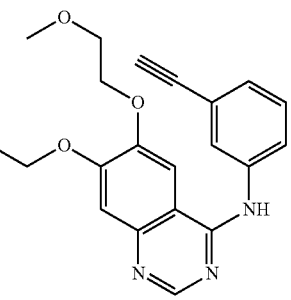

6,7Dihydrozyquinazolinone (2)

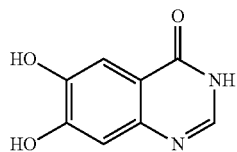

To an excess of stirred molten pyridinium hydrochloride at 180° C. was added portionwise 6-acetoxy-7-methoxy-quinazolone (1) (49.5 g, 211.35 mmol) and the resulting solution was stirred at 180° C. for 4 hours. After cooling to room temperature, water (500 ml) was added and the pH adjusted to 7 with aqueous ammonia. The resulting precipitate was collected by filtration, washed with water (5×20 ml), ether (5×20 ml) and dried to a constant weight in a vacuum oven at 40° C. to afford 6,7-dihydroxyquinazolinone (2) (38 g, 100%) as a beige solid:

LCMS (retention time=0.97 min., purity=98%), ESI+ m/z 179.18 (M+H)+; 1H-NMR (DMSO-$d_6$) δ (ppm) 6.95 (s, 1H), 7.41 (s, 1H), 7.91 (s, 1H), 9.78 (s, 1H), 10.23 (s, 1H), 11.7 (br s, 1H).

4-Oxo-3,4-dihydroquinazoline-6,7-diyl bis(2,2-dimethylpropanoate)

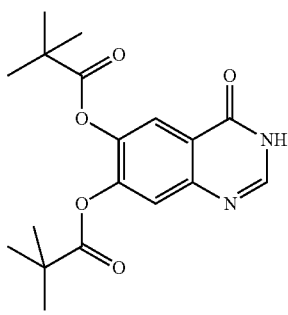 [SMILES: CC(C)(C)C(=O)Oc1cc2nc[nH]c(=O)c2cc1OC(=O)C(C)(C)C]

To a stirred suspension of 6,7-dihydroxyquinazolinone (2) (38.0 g, 213.3 mmol) and TEA (89.1 ml, 640 mmol) in DMF (200 ml), was added dropwise trimethylacetyl chloride (78.8 ml, 640 mmol). The resulting suspension was stirred at room temperature for 1 hour, diluted with EtOAc (500 ml) and washed with water (5×20 ml). The organic phase was concentrated to dryness and the residue triturated with water and the resulting precipitate was collected by filtration, washed with water (5×20 ml) and dried to a constant weight to afford the title compound (52.3 g, 71%) as a pale pink solid: LCMS (retention time=3.65 min., purity=100%), ESI+ m/z 347.33 (M+H)+; 1H-NMR (DMSO-$d_6$) δ (ppm) 1.32 (s, 18H), 7.59 (s, 1H), 7.92 (s, 1H), 8.14 (s, 1H).

4-Chloroquinazoline-6,7-diyl bis(2,2-dimethylpropanoate) (3)

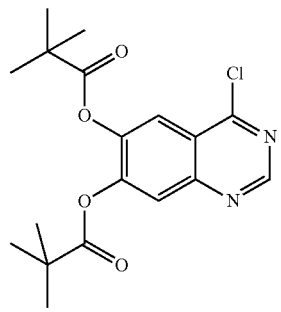 [SMILES: CC(C)(C)C(=O)Oc1cc2ncnc(Cl)c2cc1OC(=O)C(C)(C)C]

To a stirred suspension of 4-oxo-3,4-dihydroquinazoline-6,7-diyl bis(2,2-dimethylpropanoate) (68.5 g, 197.8 mmol) and TEA (110.3 ml, 791 mmol) in toluene (700 ml) at 0° C., was added neat POCl$_3$ (64.5 ml, 692 mmol). The reaction mixture was stirred for 1 h at room temperature, 2 h at 40° C. and concentrated to dryness. The residue was dissolved in DCM (500 ml) and washed with a saturated solution of sodium bicarbonate (50 ml) and water (3×50 ml). The organic phase was dried over magnesium sulfate, filtered and the filtrate concentrated to dryness. The residue was dissolved in dichloromethane and purified by flash chromatography eluting with a mixture of DCM/EtOAc (75/25+3% de DIPEA) to afford 4-chloroquinazoline-6,7-diyl bis(2,2-dimethylpropanoate) (3) (64.7 g, 76%) as a yellow oil, which crystallized upon standing to afford an orange solid: LCMS (retention time=4.32 min., purity=100%), ESI+ m/z 365.37 (M+H)+; 1H-NMR (DMSO-$d_6$) δ (ppm) 1.42 (s, 18H), 7.26 (s, 1H) 7.89 (s, 1H), 8.04 (s, 1H), 9.03 (s, 1H).

4-Chloro-6,7-hydroxyquinazoline (4)

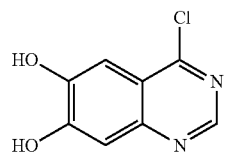

To a stirred slurry of 4-chloroquinazoline-6,7-diyl bis(2,2-dimethylpropanoate) (3) (50.7 g, 139 mmol) at 0° C., was added dropwise a solution of ammonia in methanol (7 N, 500 ml). The reaction mixture was stirred for 1 h at room temperature and evaporated to dryness. The solid was triturated with MeCN (100 ml), collected by filtration and washed with DCM (2×20 ml) and diethyl ether (5×20 ml) to afford 4-chloro-6,7-hydroxyquinazoline (4) (25.4 g, 93%) as a pale yellow solid.

4-Chloro-7-hydroxyquinazolin-6-yl pivalate (5)

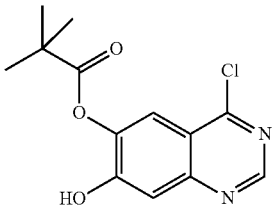 [SMILES: CC(C)(C)C(=O)Oc1cc2c(Cl)ncnc2cc1O]

To a stirred suspension of 4-chloro-6,7-hydroxyquinazoline (4) (10.0 g, 50.9 mmol) and TEA (28.3 ml, 203 mmol) in DCM (100 ml) at −10° C. (acetone/ice bath) was added dropwise trimethylacetyl chloride (8.77 ml, 71.2 mmol). The reaction mixture was stirred at room temperature for 2 hours, diluted with dichloromethane (200 ml) and washed with a 10% aqueous solution of critic acid (2×20 ml). The organic phase was dried over magnesium sulfate and concentrated to dryness at room temperature. The resulting pale yellow residue was dissolved in dichloromethane and purified by flash chromatography on silica gel eluting with a gradient of DCM/EtOAc (100/0 to 50/50) to afford 4-chloro-7-hydroxy-quinazolin-6-yl pivalate (5) (8.2 g, 57%) as a white solid. The material was used without further characterization.

Synthesis of Compound 6

To a stirred suspension of polymer-supported triphenylphosphine (3 eq, 1.2 mmol/g), the first alcohol (3 eq) in DCM (5 ml/g of resin) at 0° C., was added di-tert-azadicarboxylate (DTAD, 3 eq) followed by 5 (0.36 mmol). The reaction mixture was slowly agitated for 1 hour at room temperature, filtered and the filtrate was concentrated. Column purification may be necessary before next step, if the excess alcohol still present by TLC monitoring.

2,2-Dimethyl-propionic acid 4-chloro-7-(2-methoxy-ethoxy)-quinazolin-6-yl ester (6A)

C16H19ClN2O4, Exact Mass: 338.10. ESI⁺ m/z 339.2 (M+H)⁺. The compound is used in the next step without further characterization.

2,2-Dimethyl-propionic acid 7-[2-(2-tert-butoxycarbonylamino-ethoxy)-ethoxy]-4-chloro-quinazolin-6-yl ester (6B)

C22H30ClN3O6, Exact Mass: 467.18. ESI⁺ m/z 468.4 (M+H)⁺. The filtrate was concentrated and purified by column chromatography. The resulting pure compound is used in the next step without further characterization.

Synthesis of Compound 7

The residue (containing 6) was dissolved in methanolic ammonia (7N) and stirred for 5 hours, concentrated to dryness, re-dissolved in THF and re-concentrated to dryness to afford phenol 7.

4-Chloro-7-(2-methoxy-ethoxy)-quinazolin-6-ol (7A)

C11H11ClN2O3, Exact Mass: 254.05. ESI⁺ m/z 255.4 (M+H)⁺. The compound is used directly in the next step without further characterization.

{2-[2-(4-Chloro-6-hydroxy-quinazolin-7-yloxy)-ethoxy]-ethyl}-carbamic acid tert-butyl ester (7B)

C17H22ClN3O5, Exact Mass: 383.12. ESI⁺ m/z 384.2 (M+H)⁺. The compound is used directly in the next step without further characterization.

Synthesis of Compound 8

The phenol 7 was subsequently added to a stirred suspension of polymer-supported triphenylphosphine (4 eq), the second alcohol (4 eq), and DTAD (4 eq) at 0° C. The reaction mixture was slowly agitated for 1 hour at room temperature, filtered and concentrated to dryness. The residue was used directly in the next step without further characterization.

(2-{2-[4-Chloro-7-(2-methoxy-ethoxy)-quinazolin-6-yloxy]-ethoxy}-ethyl)-carbamic acid tert-butyl ester (8A)

C20H28ClN3O6, Exact Mass: 441.17. ESI⁺ m/z 442.3 (M+H)⁺.

(2-{2-[4-Chloro-6-(2-methoxy-ethoxy)-quinazolin-7-yloxy]-ethoxy}-ethyl)-carbamic acid tert-butyl ester (8B)

C20H28ClN3O6, Exact Mass: 441.17. ESI⁺ m/z 442.4 (M+H)⁺.

Synthesis of Compound 9

The resulting residues (8) were taken up in DMF or ACN and treated with 1.5 equivalents of aniline and 4 equivalents of HCl in dry 1,4-dioxane at 80° C. for 2 hours. The resulting mixture was diluted with water and extracted with EtOAc. The organic layer was separated, dried over MgSO₄ and concentrated. The residue was then purified by column chromatography to afford compound 9. The white solid obtained was used directly in the next step without further characterization.

(2-{2-[4-(3-Ethynyl-phenylamino)-7-(2-methoxy-ethoxy)-quinazolin-6-yloxy]-ethoxy}-ethyl)-carbamic acid tert-butyl ester (9A)

C28H34N4O6, Exact Mass: 522.25. ESI⁺ m/z 523.5 (M+H)⁺.

(2-{2-[4-(3-Ethynyl-phenylamino)-6-(2-methoxy-ethoxy)-quinazolin-7-yloxy]-ethoxy}-ethyl)-carbamic acid tert-butyl ester (9B)

C28H34N4O6, Exact Mass: 522.25. ESI⁺ m/z 523.6 (M+H)⁺.

Synthesis of Compound 10

Compound 9 was subsequently completely dissolved in 6N HCl (aq) and stirred further until a white precipitate forms. The precipitate was then filtered and washed with Et₂O and dried to afford the final compounds 10.

117

[6-[2-(2-Amino-ethoxy)-ethoxy]-7-(2-methoxy-ethoxy)-quinazolin-4-yl]-(3-ethynyl-phenyl)-amine dihydrochloride (10A)

C23H26N4O4, Exact Mass: 422.20. ESI m/z 423.6 (M+H)$^+$; $^1$H-NMR (D$_2$O) δ (ppm) 3.23 (t, 5 Hz, 2H), 3.44 (s, 3H), 3.54 (s, 1H), 3.85 (t, 5 Hz, 2H), 3.91-3.93 (m, 2H), 4.01-4.03 (m, 2H), 4.39-4.41 (m, 4H), 7.18-7.25 (m, 1H), 7.37-7.54 (m, 3H), 7.63-7.66 (m, 1H), 7.72-7.78 (m, 1H), 8.51 (s, 1H).

118

[7-[2-(2-Amino-ethoxy)-ethoxy]-6-(2-methoxy-ethoxy)-quinazolin-4-yl]-(3-ethynyl-phenyl)-amine dihydrochloride (10B)

C23H26N4O4, Exact Mass: 422.20. ESI$^+$ m/z 423.5 (M+H)$^+$; $^1$H-NMR (D$_2$O) δ (ppm) 3.21 (t, 5 Hz, 2H), 3.42 (s, 3H), 3.51 (s, 1H), 3.82 (t, 5 Hz, 2H), 3.86-3.88 (m, 2H), 3.93-3.96 (m, 2H), 4.22-4.27 (m, 2H), 4.28-4.32 (m, 2H), 6.98-7.17 (m, 3H), 7.44-7.52 (m, 3H), 8.47 (m, 1H).

Conjugate Assembly

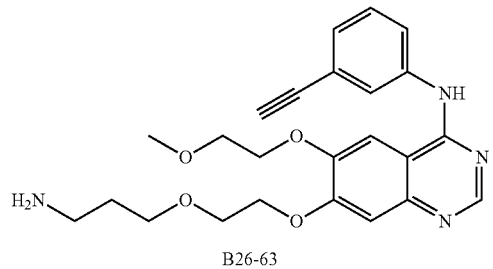

B26-63
3
500 mg provided by RJS

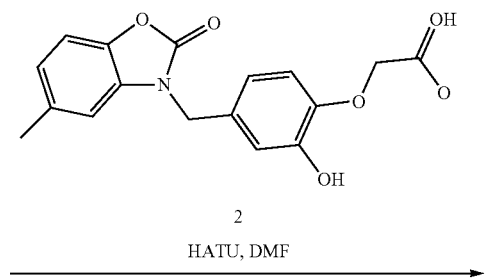

2
HATU, DMF

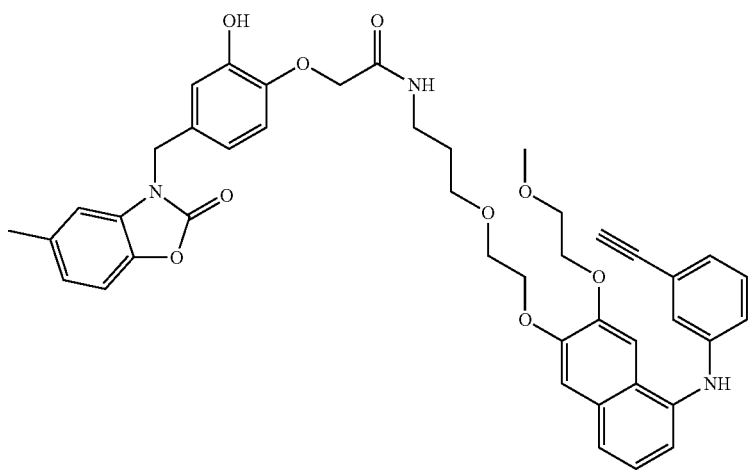

RJS013_2

10 mg  →  EDCl, 4-PYRROLIDINOPYRIDINE, DMF  →  30% product on LCMS
200 mg  →  ⎤
200 mg  →  ⎦ After purification again by HPLC and lyophilization, the solid is under identification

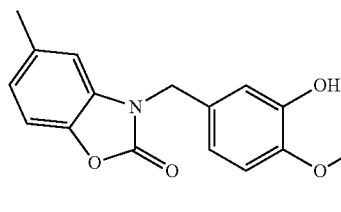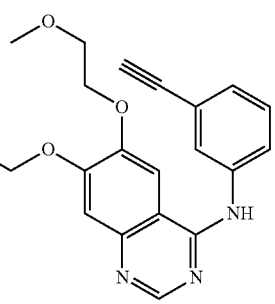

This example illustrates several in vitro experiments in predictive models of cancer to show the potential therapeutic utility of the disclosed compounds. Human tumor cell lines of a cancer screening panel were grown in RPMI 1640 medium containing 5% fetal bovine serum and 2 mM L-glutamine. Cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of experimental drugs.

After 24 h, two plates of each cell line were fixed in situ with trichloroacetic acid (TCA), to represent a measurement of the cell population for each cell line at the time of drug addition (T=zero). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 g/ml gentamicin. Additionally four, 10-fold serial dilutions were made to provide a total of five drug concentrations plus control. Aliquots of 100 μl of these different drug dilutions were added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and were incubated for 60 minutes at 4° C. The supernatant is discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the seven absorbance measurements [time zero, (T=zero), control growth, (C), and test growth in the presence of drug at the five concentration levels (Ti)], the percentage growth was calculated at each of the drug concentrations levels.

Percentage growth inhibition was calculated as:

[(Ti−Tzero)/(C−Tzero)]×100 for concentrations for which Ti>/=Tzero

[(Ti−Tzero)/Tzero]×100 for concentrations for which Ti<Tzero.

Three dose response parameters were calculated for each experimental agent. Growth inhibition of 50% (GI50) was calculated from [(Ti−Tzero)/(C−Tzero)]×100=50, which was the drug concentration resulting in a 50% reduction in the net protein increase (as measured by SRB staining) in control cells during the drug incubation. The drug concentration resulting in total growth inhibition (TGI) was calculated from Ti=Tzero. The LC50 (concentration of drug resulting in a 50% reduction in the measured protein at the end of the drug treatment as compared to that at the beginning) indicating a net loss of cells following treatment was calculated from [(Ti−Tzero)/Tzero]×100=−50. Values were calculated for each of these three parameters if the level of activity was reached; however, if the effect was not reached or was exceeded, the value for that parameter was expressed as greater or less than the maximum or minimum concentration tested. These parameters were used to plot FIG. 1 through FIG. 18. The same procedures were used to create FIGS. 19 and 20 except a single 10 μM data point was recorded for each cell line.

Assay Example 2

This example illustrates an in vitro experiment using predictive models of cancer to show the cellular specificity and potential therapeutic utility of the inventive compounds. The human leukemic cell line THP-1 was grown in RPMI 1640 medium with penicillin, streptomycin, and containing 25 mM Hepes, 0.05 mM 2-mercaptoethanol, 10% fetal bovine serum and 2 mM L-glutamine. Cells washed 2× with Gibco Life Sciences (Grand Island, N.Y.) AIM-V serum free medium and then were inoculated into 96 well microtiter plates in 100 μL at plating densities ranging from 25,000 to 100,000 cells/well. Five to ten million frozen peripheral blood mononuclear cells (PBMCs) (Astarte Biologics, LLC. (Redmond, Wash.)) in a solution of 10% DMSO, 2% human serum albumin in phosphate buffered saline were thawed and immediately washed in AIM-V media. An approximately equal number of these cells (25,000 to 100,000 cells/well) were added to the experimental plate. Doxorubicin was added to a final concentration of 0.8 μM. The microtiter plates were incubated at 37° C., 5% $CO_2$, 95% air and 100% relative humidity for 2-2.5 h then drug uptake was quantified by flow cytometry for example using a BD FACSCanto II (San Jose, Calif.). Doxorubicin uptake was evaluated in the PE channel. Individual cell populations were identified by size, shape and through the use of dye labeled antibodies.

Synthesis of RJS012_1

Final Structure—

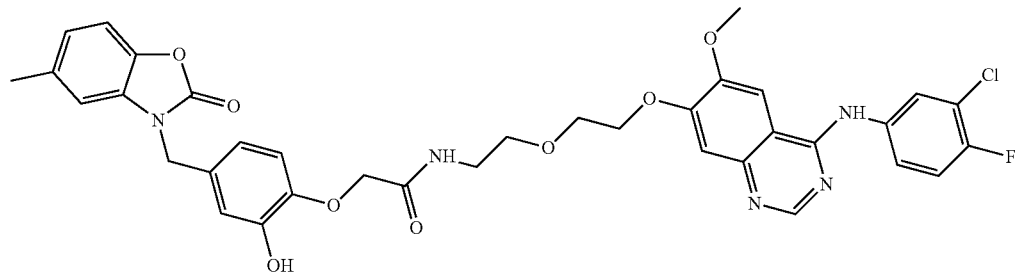 [SMILES: COc1cc2c(Nc3ccc(F)c(Cl)c3)ncnc2cc1OCCOCCNC(=O)COc1ccc(Cn2c(=O)oc3ccc(C)cc32)cc1O]

Synthesis—

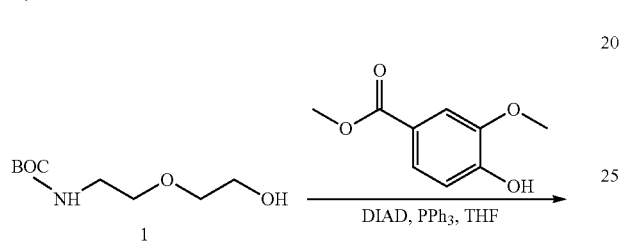

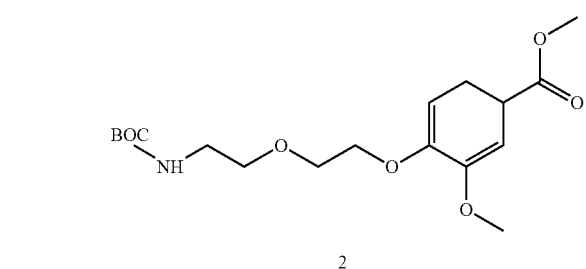

To a solution of Compound 1 (2 g, 9.74 mmol), methyl 4-hydroxy-3-methoxybenzoate (1.95 g, 10.72 mmol) and PPh₃ (3.07 g, 11.69 mmol) in 30 mL of THF was added DIAD (2.36 g, 11.69 mmol) dropwise at 0° C. under N₂. The mixture was stirred overnight and isolated with NaHCO₃ (50 mL) and EtOAc (50 mL), the aqueous layer was extracted with EtOAc (2*50 mL). The combined organic layer was washed with brine (2*50 mL), dried over MgSO₄ and concentrated, the residue was purified by column (Petroleum Ether:EtOAc=2:1) to give Compound 2 as white solid.

2. Synthesis of Compound 3:

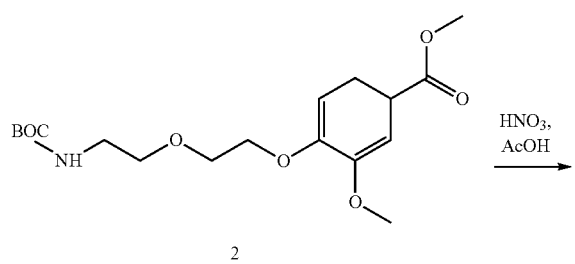

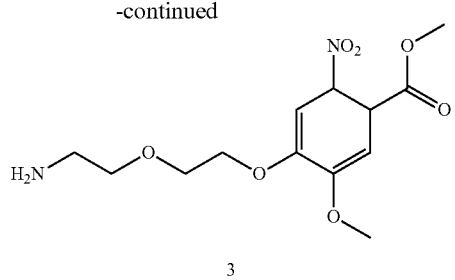

Compound 2 (2.1, 5.68 mmol) in 10 mL of AcOH was added HNO₃ (3.58 g, 56.8 mmol) dropwise at 20° C. and stirred for 3 hrs. The mixture was quenched by adding in portions to ice water (30 mL). The resulting mixture was basified with 1M NaOH to pH=10 and extracted with EtOAc (3*40 mL). The combined organic layer was dried and concentrated. The residue was used to next step without purification.

3. Synthesis of Compound 4:

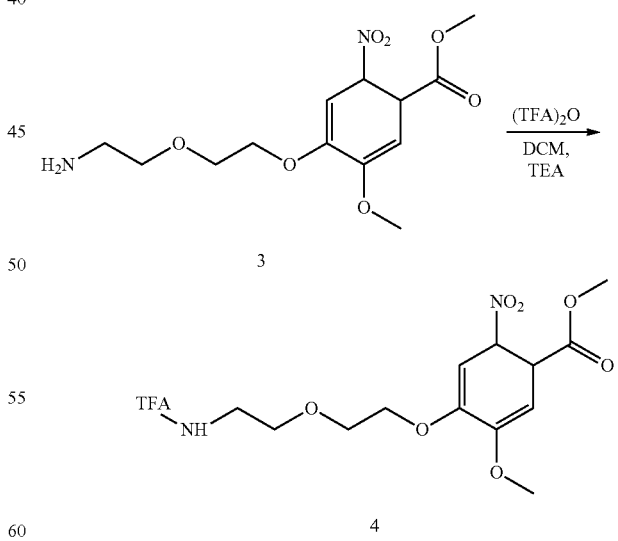

To a solution of Compound 3 (1.9 g crude) in 20 mL of dry CH₂Cl2 was added Et₃N (2.45 g, 24.18 mmol). To the above solution was added TFAA (2.54 mg, 12.09 mmol) dropwise at 0° C. and stirred for 2 hrs. The mixture was concentrated and the residue was purified by column (Petroleum Ether:EtOAc=2:1) to give compound 4 as oil (1.2 g).

4. Synthesis of Compound 5:

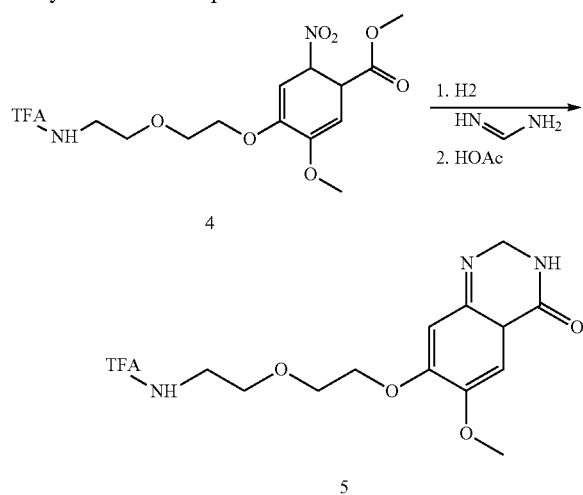

A mixture of compound 4 (1.2 g, 2.92 mmol) and Pd/C (250 mg) in 50 mL of MeOH was stirred at r.t. under 15 psi of H₂ for 3 hrs. The mixture was filtered. To the filtrate, formimidamide acetate was added
(3.01 g, 28.92 mmol) and stirred at 90° C. for 3 hrs. The mixture was concentrated, the residue was washed with H₂O (100 mL) to give compound 5 as solid (1 g).

5. Synthesis of Compound 8:

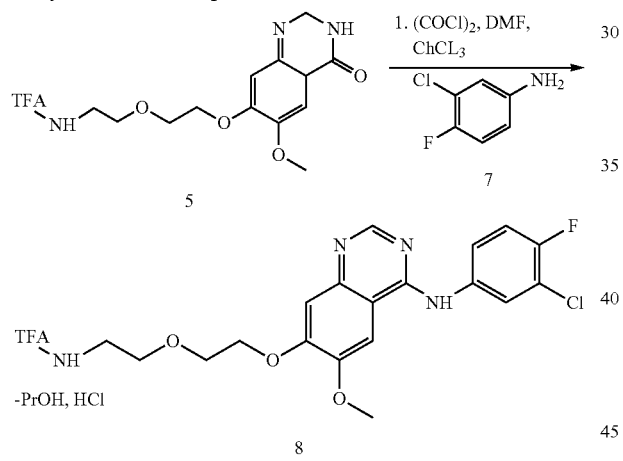

To a solution of compound 5 (1 g, 2.66 mmol) and DMF (1 drop) in 30 mL of CHCl₃ was added (COCl)₂ (676 mg, 5.33 mmol) drop wise and stirred at 80° C. for 3 hrs. The mixture was concentrated. To the residue was added i-PrOH (30 mL) and compound 7 (739.4 mg, 5.08 mmol). To the above mixture was added HCl (1 mL, 12M) and refluxed for 2 hrs. The residue was isolated with NaHCO₃ (50 mL) and CHCl₃ (90 mL). The organic layer was washed with brine (50 mL), dried over MgSO₄ and concentrated. The residue was purified by column (Petroleum ether:EtOAc=1:3) to give compound 8 as oil (600 mg).

6. Synthesis of Compound 9:

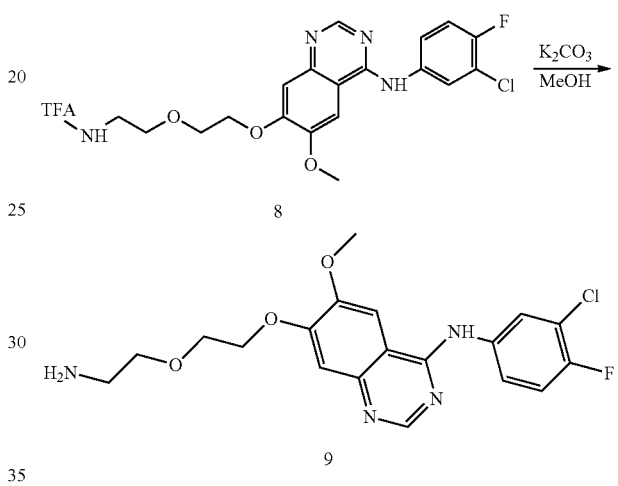

To a solution of compound 8 (30 mg, 59.66 umol) in 1 mL of MeOH was added K₂CO₃ (41.2 mg, 298.3 umol). The mixture was stirred at 80° C. for 6 hrs. The mixture was isolated with EtOAc (10 mL) and H₂O (10 mL). The aqueous layer was extracted with EtOAc (2*10 mL). The combined organic layer was washed with brine (15 mL), dried over MgSO₄ and concentrated to give compound 9 as solid.

7. Synthesis of RJS012_1:

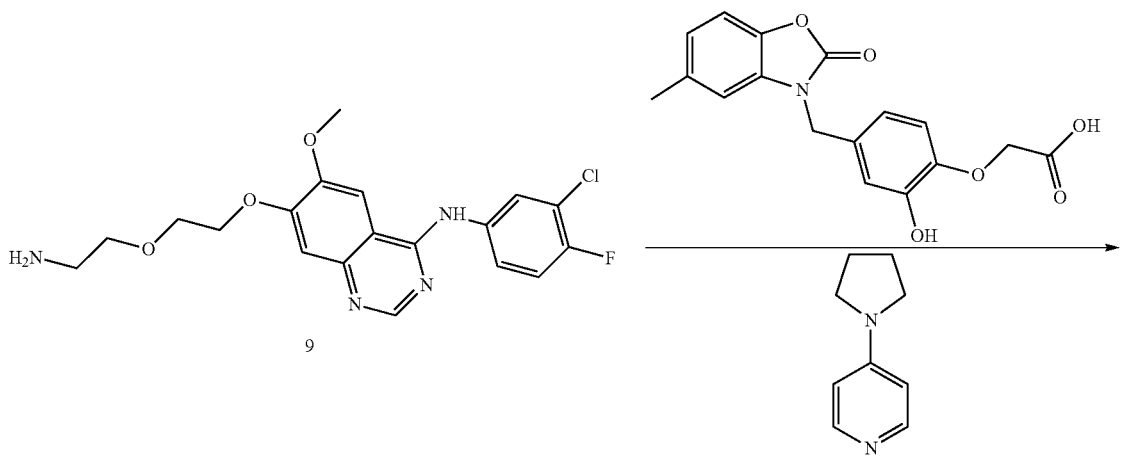

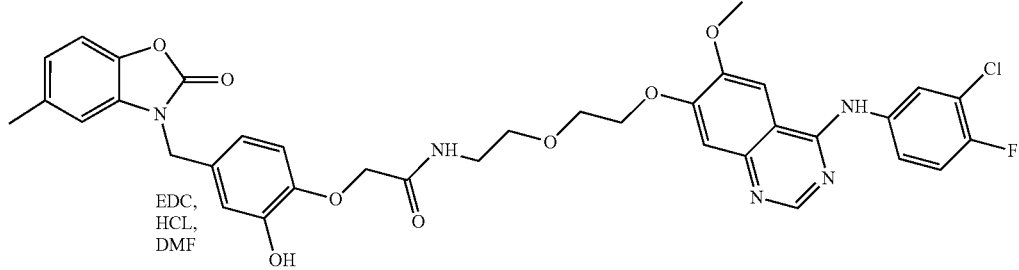

RJS012_1

To a solution of compound 9 (110 mg, 270.38 umol), compound 11 (133.55 mg, 405.57 umol) and 4-(pyrrolidin-1-yl)pyridine (80.14 mg, 540.76 umol) in 20 mL of DMF was added EDC HCl (103.66 mg, 540.76 umol). The mixture was stirred overnight and concentrated. The residue was purified by column (EtOAc:MeOH=20:1) to give product as solid. Totally 110 mg was obtained.

Synthesis of RJS012_3

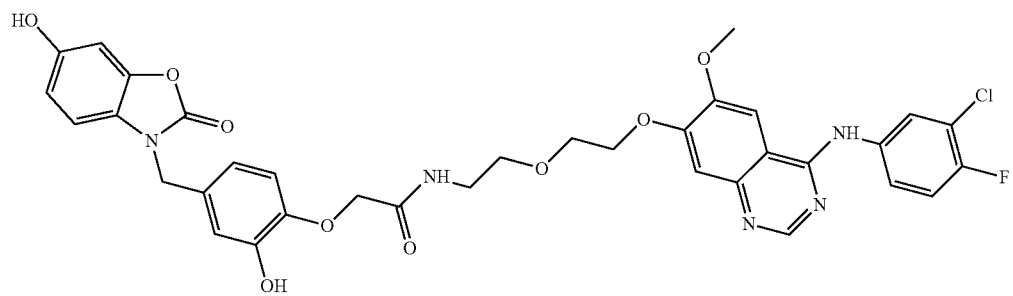 [SMILES: COc1cc2c(Nc3ccc(F)c(Cl)c3)ncnc2cc1OCCOCCNC(=O)COc1ccc(Cn2c(=O)oc3cc(O)ccc32)cc1O]

1. Synthesis of Compound 2

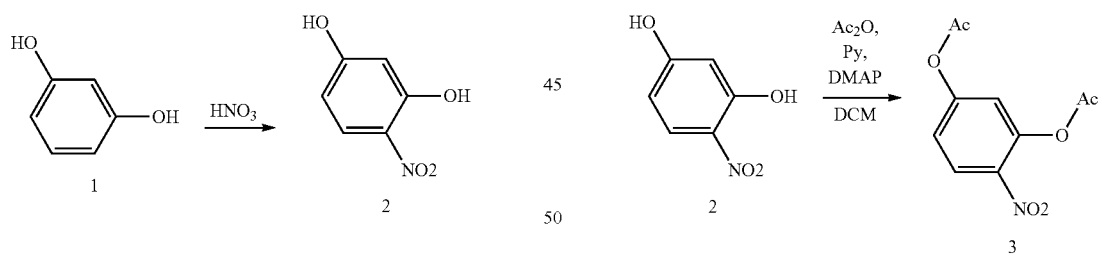

To a solution of resorcinol (20.0 g, 181.64 mmol) in a mixture (2:1, 900 mL) of chloroform and acetic acid was slowly added a solution of nitric acid (20 mL) in acetic acid (100 mL). After being stirred for 1 h, the reaction mixture was quenched with water (1 L) and extracted with $CH_2Cl_2$ (1 L*3). The organic layer was dried over $MgSO_4$ and concentrated under reduced pressure. The residue was purified by column chromatography on silica gel (EtOAc/Petroleum Ether=1:4 to 1:2) to afford of nitroresorcinol 2 as yellow solid (6 g, 21.3%).

2. Synthesis of Compound 3

$Ac_2O$ (9.87 g, 96.70 mmol, 2.50 Eq) was added to the mixture of 4-nitrobenzene-1,3-diol (6.00 g, 38.68 mmol, 1.00 Eq), PYRIDINE (6.70 g, 84.70 mmol, 2.19 Eq) and DMAP (472.55 mg, 3.87 mmol, 0.10 Eq) in $CH_2Cl_2$ (100 mL) at 0° C. The temperature of the reaction was raised to 15° C., followed by stirring for 1 hour. The reaction solution was washed with 50 ml of water, 100 ml of 1N-hydrochloric acid, 100 ml of saturated aqueous sodium bicarbonate, and 100 ml of saturated brine sequentially, dehydrated with anhydrous $MgSO_4$, and subsequently concentrated under reduced pressure to afford (3-acetoxy-4-nitro-phenyl)acetate (8.00 g, 33.45 mmol, 86.47% yield) as yellow solid.

3. Synthesis of Compound 4

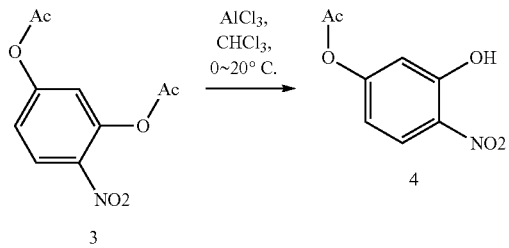 [SMILES: CC(=O)Oc1ccc([N+](=O)[O-])c(OC(C)=O)c1 ; CC(=O)Oc1ccc([N+](=O)[O-])c(O)c1]

AlCl₃ (15.61 g, 117.07 mmol, 4.00 Eq) was added to the solution of (3-acetoxy-4-nitro-phenyl)acetate (7.00 g, 29.27 mmol, 1.00 Eq) in CHCl3 (300 mL) at 0° C. under N₂. The reaction mixture was stirred at 0° C. for 0.5 h and 25° C. for 3 h. The reaction mixture was poured into ice-water, and extracted with CH₂Cl₂ (100 mL*2). The combined organic layers were washed with 1N HCl and brine. After drying over MgSO₄ and filtering, the filtrate was concentrated. The residue was purified by flash chromatography on silica gel (0-30% EtOAc in petroleum ether) to obtain (3-hydroxy-4-nitro-phenyl)acetate (4.50 g, 22.83 mmol, 77.99% yield) as light yellow solid.

4. Synthesis of Compound 5

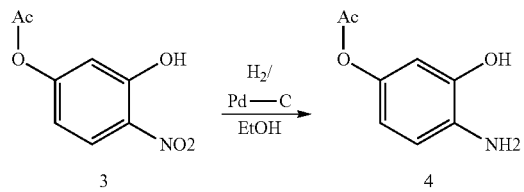

The mixture of (3-hydroxy-4-nitro-phenyl)acetate (4.50 g, 22.83 mmol, 1.00 Eq) and Pd/C (100.00 mg, 22.83 mmol, 1.00 Eq) in EtOAc (500 mL) was stirred at 20° C. for 18 under H₂(30 Psi). After filtration through Celite, the filtrate was concentrated to obtain (4-amino-3-hydroxy-phenyl)acetate (3.44 g, 20.58 mmol, 90.16% yield) which was used in the next step without further purification.

5. Synthesis of Compound 7

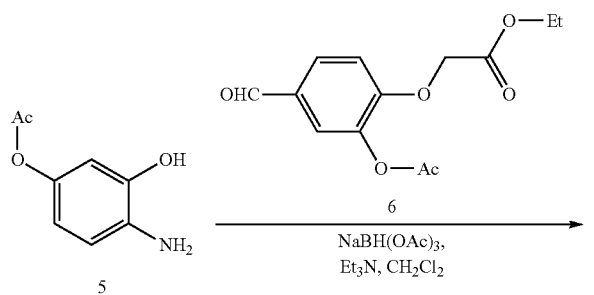

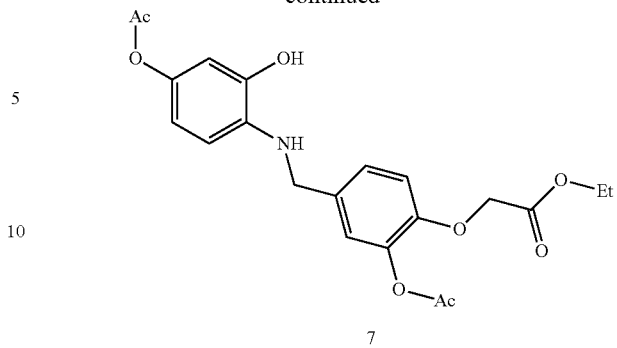

A mixture of (4-amino-3-hydroxy-phenyl)acetate (4.33 g, 25.90 mmol, 1.00 Eq), ethyl 2-(2-acetoxy-4-formyl-phenoxy)acetate (6.90 g, 25.90 mmol, 1.00 Eq) and Et₃N (7.86 g, 77.71 mmol, 3.00 Eq) in CH₂Cl₂ (100 mL) was stirred at 20° C. for 0.5 h. NaBH(OAc)₃ (16.47 g, 77.71 mmol, 3.00 Eq) was added. The resulting mixture was stirred at 20° C. for 18 h. The reaction was washed by NH₄Cl (saturated aqueous solution), a CO3 (saturated aqueous solution), brine, dried over MgSO4, filtered and concentrated to obtain ethyl 2-[2-acetoxy-4-[(4-acetoxy-2-hydroxy-anilino)methyl]phenoxy]acetate (11.50 g, 25.35 mmol, 97.86% yield, 92% purity) which was used in the next step without further purification.

6. Synthesis of Compound 8

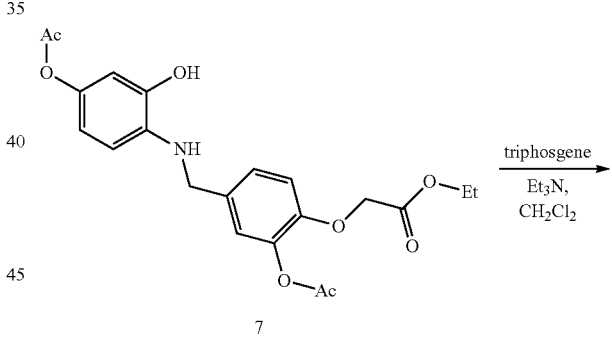

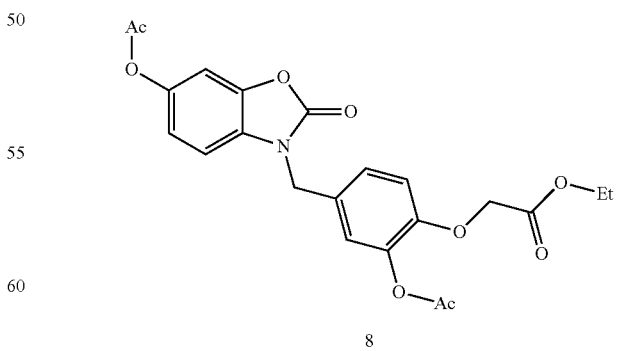

TRIPHOSGENE (2.35 g, 7.91 mmol, 0.33 Eq) in 200 mL of CH₂Cl₂ was added dropwise to the solution of ethyl 2-[2-acetoxy-4-[(4-acetoxy-2-hydroxy-anilino)methyl]phenoxy]

acetate (10.00 g, 23.96 mmol, 1.00 Eq) and Et₃N (7.27 g, 71.88 mmol, 3.00 Eq) in CH₂Cl₂ (500 mL) at 0° C. under N₂. The resulting mixture was stirred at 25° C. for 18 h. The reaction was washed with brine, dried over MgSO₄, filtered and concentrated. The residue was purified by flash chromatography on silica gel (10-30% EtOAc in petroleum ether) to obtain ethyl 2-[2-acetoxy-4-[(6-acetoxy-2-oxo-1,3-benzoxazol-3-yl)methyl]phenoxy]acetate (7.00 g, 15.79 mmol, 65.89% yield) as orange solid.

7. Synthesis of Compound 9

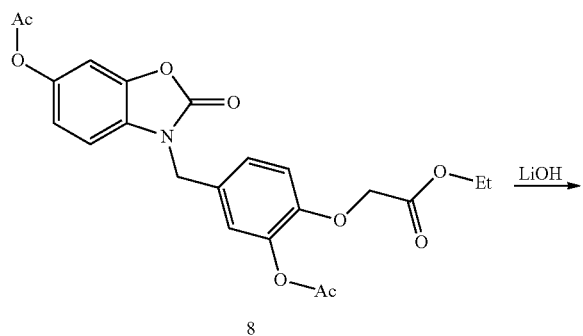

LiOH (216.06 mg, 9.02 mmol, 4.00 Eq) in Water (5 mL) was added to the solution of ethyl 2-[2-acetoxy-4-[(6-acetoxy-2-oxo-1,3-benzoxazol-3-yl)methyl]phenoxy]acetate (1.00 g, 2.26 mmol, 1.00 Eq) in THF (10 mL) acidified to pH=3. The mixture was extracted with EtOAc (500 mL*3). The combined organic layers were dried over MgSO₄, filtered and concentrated to obtain 2-[2-hydroxy-4-[(6-hydroxy-2-oxo-1,3-benzoxazol-3-yl)methyl]phenoxy]acetic acid (500.00 mg, 1.50 mmol, 66.55% yield, 99.65% purity) which was used in the next step without further purification.

8. Synthesis of Compound RJS012_3

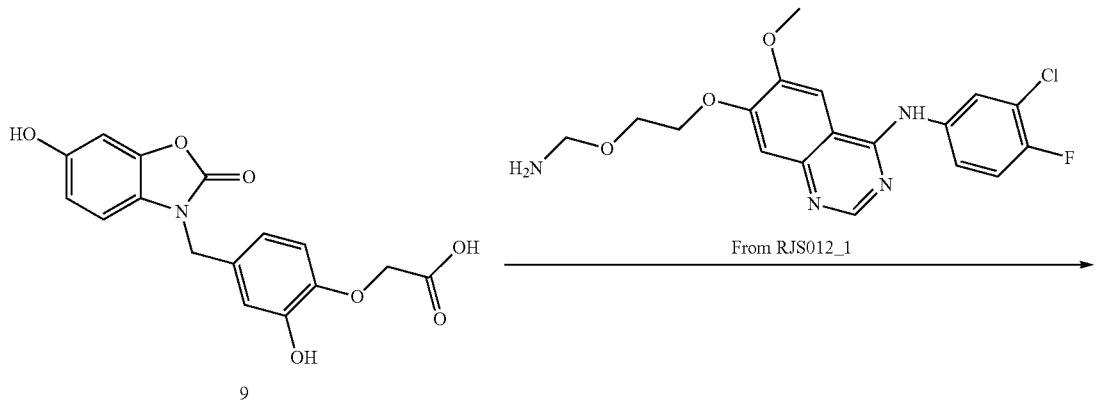

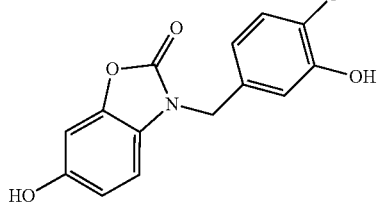

EDCI (231.47 mg, 1.21 mmol, 2.00 Eq) was added to the mixture of 7-[2-(2-aminoethoxyl)ethoxy]-N-(3-chloro-4-fluoro-phenyl)-6-methoxy-quinazolin-4-amine (245.62 mg, 603.72 umol, 1.00 Eq) and 2-[2-hydroxy-4-[(6-hydroxy-2-oxo-1,3-benzoxazol-3-yl)methyl]phenoxy]acetic acid (200.00 mg, 603.72 umol, 1.00 Eq) in DMF (50 mL). 4-pyrrolidin-1-ylpyridine (178.94 mg, 1.21 mmol, 2.00 Eq) was added. The reaction was stirred at 25° C. for 18 hr. The reaction was diluted with EtOAc (100 mL) and washed with NH$_4$Cl (saturated), brine, dried over MgSO$_4$, filtered and concentrated. The residue was purified by HPLC (TFA condition) to obtain N-[2-[2-[4-(3-chloro-4-fluoro-anilino)-6-methoxy-quinazolin-7-yl]oxyethoxy]ethyl]-2-[2-hydroxy-4-[(6-hydroxy-2-oxo-1,3-benzoxazol-3-yl)methyl]phenoxy]acetamide (113.00 mg, 152.91 umol, 25.33% yield, 97.44% purity) as white solid.

TABLE 2

Selectivity of affinity-tethered Doxorubicin derivatives

| Drug | IC$_{50}$ Cancer Cells ATCC SR (µM) | IC$_{50}$ 1° Fibroblasts (µM) | Selectivity |
|---|---|---|---|
| Doxorubicin | 0.007 ± 7% | 0.185 ± 0.5% | 26 |
| RJS04_5 | 0.263 ± 7.6% | >80 | >304 |
| RJS09_1 | 0.066 ± 12% | 4.38 ± 4% | 68 |
| RJS010_2 | 0.033 ± 24% | 3.55 ± 0.56% | 107 |

Table 2—

The IC50's of Doxorubicin and Doxorubicin conjugates in large cell immunoblastic lymphoma cell lines (ATCC SR) and Normal Human Adult Dermal Fibroblasts (ATCC PCS-201-012) were compared using a WST-8 cellular proliferation assay (Cayman Chemical Co. (Ann Arbor, Mich.). Large Cell Immunoblastic Lymphoma cells (SR) were grown in TCC-formulated RPMI-1640 Medium plus 10% fetal bovine serum. Primary dermal fibroblasts were grown in Fibroblast Basal Medium (ATCC) plus the contents of the ATCC fibroblast growth kit low serum (rh FGF b, L-glutamine, Ascorbic acid, Hydrocortisone, rh Insulin hemisuccinate, Fetal Bovine Serum). Assays were performed according to the manufactures instructions.

TABLE 3

Selectivity of affinity-tethered Artemisinin derivatives

| Drug | IC$_{50}$ Cancer Cells ATCC SR (µM) | IC$_{50}$ 1° Fibroblasts (µM) | Selectivity |
|---|---|---|---|
| ART-OH | 28.6 | >100 | >3.8 |
| RJS05_1 | 1.0 | 51.3 | 51.3 |
| RJS05_2 | 4.6 | 119 | 26 |
| RJS05_3 | 8.5 | 103 | 12 |

Table 3—The IC50's of Artemisinin and Artemisinin conjugates in large cell immunoblastic lymphoma cell lines (ATCC SR) and Normal Human Adult Dermal Fibroblasts (ATCC PCS-201-012) were compared using a WST-8 cellular proliferation assay (Cayman Chemical Co. (Ann Arbor, Mich.). Large Cell Immunoblastic Lymphoma cells (SR) were grown in TCC-formulated RPMI-1640 Medium plus 10% fetal bovine serum. Primary dermal fibroblasts were grown in Fibroblast Basal Medium (ATCC) plus the contents of the ATCC fibroblast growth kit low serum (rh FGF b, L-glutamine, Ascorbic acid, Hydrocortisone, rh Insulin hemisuccinate, Fetal Bovine Serum). Assays were performed according to the manufactures instructions.

TABLE 4

Selectivity of affinity-tethered EGFRi derivatives

| Drug | IC$_{50}$ Cancer Cells ATCC NCI-H460 (µM) | IC$_{50}$ 1° Fibroblasts (µM) | Selectivity |
|---|---|---|---|
| Iressa ® (gefitinib) | 29.2 | 7.4 | 0.25 |
| Tarceva ® (Erlotinib) | 12.6 | 4.7 | 0.37 |
| Docomitinib (PF-00299804) | 10.6 | 0.89 | 0.08 |
| RJS012_1 | 3.6 | 6.7 | 1.9 |
| RJS013-2 | 6.0 | 3.9 | 0.65 |

Table 4—

The IC50's of EGFRi's and EGFRi conjugates in large cell lung cancer cell lines (NCI-H460) and normal human adult dermal fibroblasts were compared using a WST-8 cellular proliferation assay (Cayman Chemical Co. (Ann Arbor, Mich.). NCI-H460 lung cancer cells were grown in TCC-formulated RPMI-1640 Medium plus 10% fetal bovine serum. Primary dermal fibroblasts were grown in Fibroblast Basal Medium (ATCC) plus the contents of the ATCC fibroblast growth kit low serum (rh FGF b, L-glutamine, Ascorbic acid, Hydrocortisone, rh Insulin hemisuccinate, Fetal Bovine Serum). Assays were performed according to the manufactures instructions.

Assay Example 3

This example illustrates an in vitro experiment using predictive models of cancer to show the cellular specificity and potential therapeutic utility of the inventive compounds. The human leukemic cell line THP-1 was grown AIM-V serum free medium Gibco Life Sciences (Grand Island, N.Y.). Doxorubicin or compound 9 were added to the medium (AIM-V serum free media) and used for ISO-1 dilution. ISO-1 was diluted in Doxorubicin or compound 9, also called "tethered-doxorubicin," to the desired ISO-1 concentration (120 µl per well 96 well dish). Then the washed THP-1 cells were added to the drug dilutions to start the experiment ~75,000 cells per well. Test compounds were incubated 2 hrs at 37° C., then the plate was read by flow cytometry BD Canto 2 (80 µl~25,000 cells). A population of Single Round "average" cells was selected by FSC and SSC—constituting %70 of the total cell population examined. The amount of doxorubicin uptake was evaluated for this population in the PE channel. FIG. 22 shows that a known MIF tautomerase inhibitor (ISO-1) interferes with the selective uptake of doxorubicin covalently bound to a tethering moiety described herein (compound 9) but not doxorubicin.

Assay Example 4

This example illustrates an in vitro experiment using predictive models of cancer to show the altered intracellular compartmentalization and potential therapeutic utility. THP-1 monocytes were cultured in RPMI-1640 Medium, 2-mercaptoethanol to a final concentration of 0.05 mM and fetal bovine serum to a final concentration of 10%. A549 cells were cultured in F-12K Medium with fetal bovine serum to a final concentration of 10%.

Cancer cell lines were treated with 0.8 µM compound 9 or doxorubicin for 2 hrs at 37° C. The cells were then treated with the nuclear stain Hoechst trihydrochloride, trihydrate, (Invitrogen, Grand Island, N.Y.) for 30'. Images were recorded using a Zeiss LSM 510 meta confocal microscope 40×. Data shown in FIGS. 23 and 24 demonstrate efficient transport of (compound 9), into the cytoplasm of treated cancer cell lines.

I claim:

1. A tether molecule comprising a compound from formula (1)

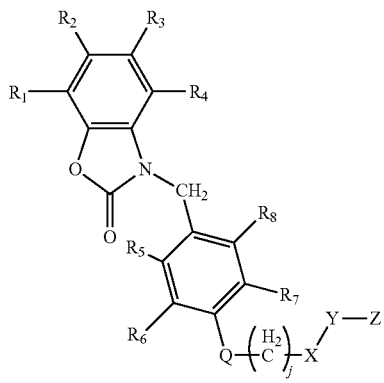

(1)

wherein Q is selected from the group consisting of O, S, N(R9), and C(R9)R10;

X is selected from the group consisting of nothing, O, S, N(R9), N(R9)N(R10), (CH$_2$)k-(OCH$_2$CH$_2$)l, CR9R10-CR11R12, and C(O);

Y is selected from the group consisting of nothing, O, S, N(R11), N(R11)N(R12), —NC(O), C(O)O—, C(O)N(R9)-, C(O)N(R9)N(R10)-, C(O)N(R9)N=, C(O)(CH$_2$)m-S—, and C(O)(CH$_2$)m-S—S—;

R1, R2, R3, R4, R5, R6, R7 and R8 are each independently selected from the group consisting of H, hydroxyl, substituted C1-C8 alkyl, substituted C1-C8 alkyl, alkenyl, alkynyl, C1-C8 acyl, substituted C1-C8 acyl, C1-C8 alkoxy, substituted C1-C8 alkoxy, C1-C8 ester, substituted C1-C8 ester, (CH$_2$)n-phenyl, substituted (CH$_2$)n-phenyl, (CH$_2$)n-heterocycle, substituted (CH$_2$)n-heterocycle, halogen, cyano, nitro, amino, (CH$_2$)n-monoalkylamine, substituted (CH2)n-monoalkylamine, (CH$_2$)n-dialkylamine, substituted (CH$_2$)n-dialkylamine, carboxylic acid, (CH$_2$)n-dialkylamine, and substituted (CH$_2$)n-alkylamide j, k, l, m and n are each integers independently from 1 to 8; and Z represents the location for binding a drug or imaging moiety.

2. The tether molecule of claim 1, wherein the tether compound is selected from the group consisting of:

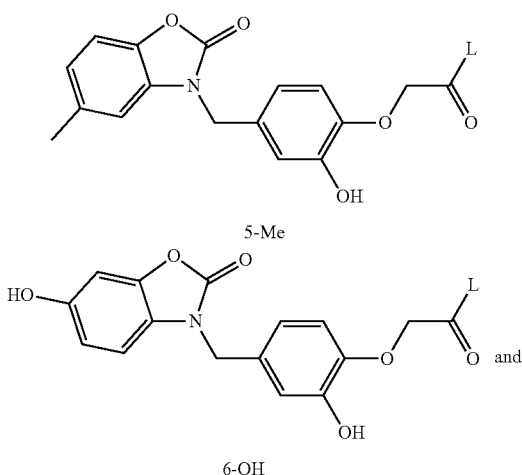

5-Me

6-OH

-continued

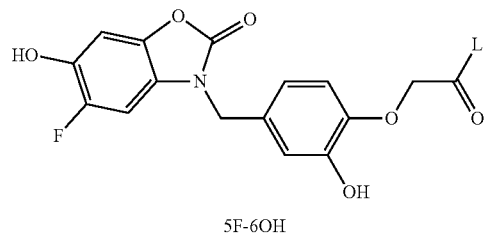

5F-6OH wherein L is a linker or spacer unit is selected from the group consisting of nothing, O, S, N(R11), N(R11)N(R12), —NC(O), C(O)O—, C(O)N(R9)=, C(O)N(R9)N(R10)-, C(O)N(R9)N=, C(O)(CH$_2$)m-S—, and C(O)(CH$_2$)m-S—S—.

3. The tether molecule of claim 1, wherein Q is O; j is 1; X is C(O); Y is nothing; R1, R2, R4, R5, R7, and R8 are hydrogen; R3 is methyl; R6 is hydroxyl and Z is a drug selected from the group consisting of doxorubicin, artemisinin, iressa, tarceba, and combinations thereof is bound to the tethering molecule at location Z.

4. The tether molecule of claim 1, wherein the compound is:

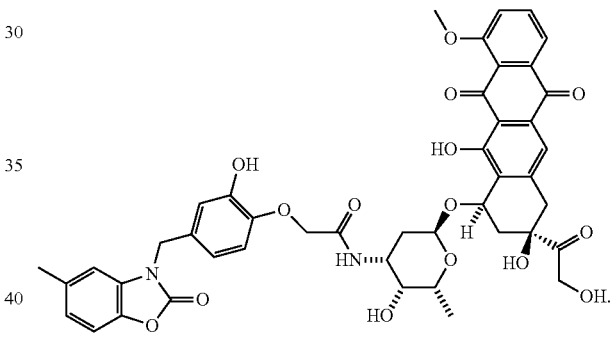

5. The tether molecule of claim 1, wherein Q is O; j is 1; X is nothing; Y is C(O)N(R9)N=; R1, R2, R4, R5, R7, R8, and R9 are hydrogen; R3 is methyl; R6 is hydroxyl; and Z is Doxorubicin hound to the tethering molecule at location Z.

6. The tether molecule of claim 1, wherein the compound is:

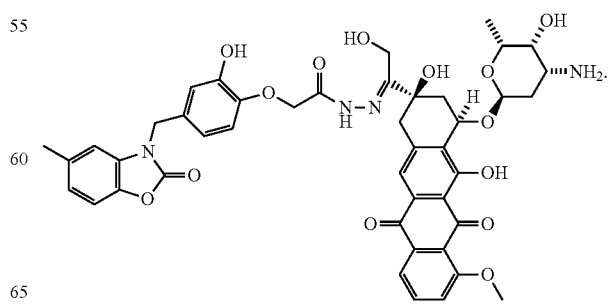

7. The tether molecule of claim 1, wherein the compound is:

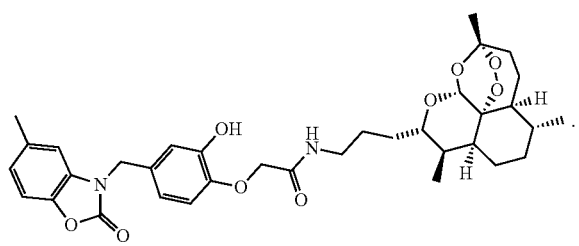

8. A pharmaceutical composition comprising a tether moiety of formula (1)

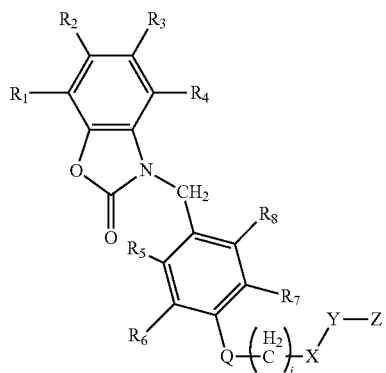

(1)

wherein Q is selected from the group consisting of O, S, N(R9), and C(R9)R10;

X is selected from the group consisting of nothing, O, S, N(R9), N(R9)N(R10), (CH₂)k-(OCH₂CH₂)l, CR9R10-CR11R12, and C(O);

Y is selected from the group consisting of nothing, O, S, N(R11), N(R11)N(R12), —NC(O), C(O)O—, C(O)N(R9)-, C(O)N(R9)N(R10)-, C(O)N(R9)N═, C(O)(CH₂)m-S—, and C(O)(CH₂)m-S—S—;

R1, R2, R3, R4, R5, R6, R7 and R8 are each independently selected from the group consisting of H, hydroxyl, substituted C1-C8 alkyl, substituted C1-C8 alkyl, alkenyl, alkynyl, C1-C8 acyl, substituted C1-C8 acyl, C1-C8 alkoxy, substituted C1-C8 alkoxy, C1-C8 ester, substituted C1-C8 ester, (CH₂)n-phenyl, substituted (CH₂)n-phenyl, (CH₂)n-heterocycle, substituted (CH₂)n-heterocycle, halogen, cyano, nitro, amino, (CH₂)n-monoalkylamine, substituted (CH2)n-monoalkylamine, (CH₂)n-dialkylamine, substituted (CH₂)n-dialkylamine, carboxylic acid, (CH₂)n-dialkylamine, and substituted (CH₂)n-alkylamide j, k, l, m and n are each integers independently from 1 to 8; Y is selected from the group consisting of nothing, O, S, N(R11), N(R11)N(R12), —NC(O), C(O)O—, C(O)N(R9)═, C(O)N(R9)N(R10), C(O)N(R9)N═, C(O)(CH₂)m-S—, and C(O)(CH₂)m-S—S—, and Z represents a drug or an imaging moiety.

9. The pharmaceutical composition of claim 8, wherein the tether moiety is selected from the group consisting of:

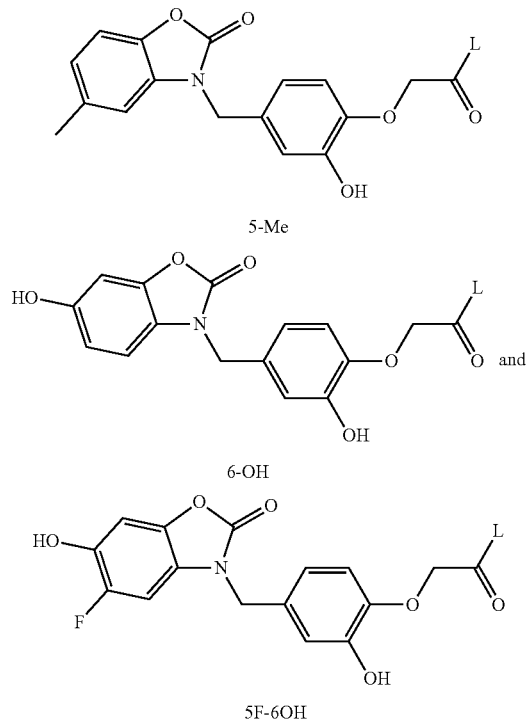

5-Me

6-OH 5F-6OH wherein L is a linker or spacer unit selected from the group consisting of nothing, O, S, N(R11), N(R11)N (R12), —NC(O), C(O)O—, C(O)N(R9)═, C(O)N(R9) N(R10)-, C(O)N(R9)N═, C(O)(CH₂)m-S—, and C(O) (CH₂)m-S—S—, bound to a Z moiety.

10. The pharmaceutical composition of claim 8, wherein Q is O; j is 1; X is C(O); Y is nothing; R1, R2, R4, R5, R7, and R8 are hydrogen; R3 is methyl; R6 is hydroxyl and Z is selected from the group consisting of doxorubicin, artemisinin, iressa, tarceba, and combinations thereof.

11. The pharmaceutical composition of claim 8, wherein the compound is:

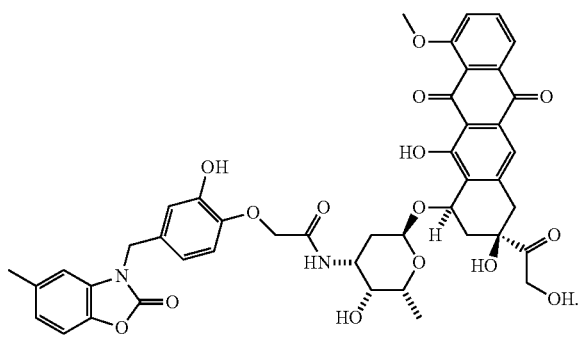

12. The pharmaceutical composition of claim 8, wherein Q is O; j is 1; X is nothing; Y is C(O)N(R9)N═; R1, R2, R4, R5, R7, R8, and R9 are hydrogen; R3 is methyl; R6 is hydroxyl; and Z is Doxorubicin.

13. The pharmaceutical composition of claim 8, wherein the compound is:

14. The pharmaceutical composition of claim 8, wherein the compound is:

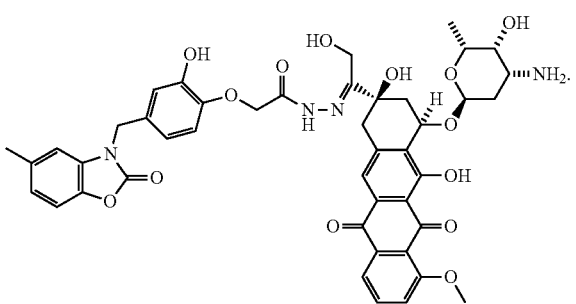 [SMILES: COc1cccc2c1C(=O)c1c(cc3c(c1O)[C@H](O[C@@H]1C[C@@H](N)[C@@H](O)[C@@H](C)O1)C[C@@](O)(/C(CO)=N/NC(=O)COc1ccc(Cn4c(=O)oc5ccc(C)cc54)cc1O)C3)C2=O]

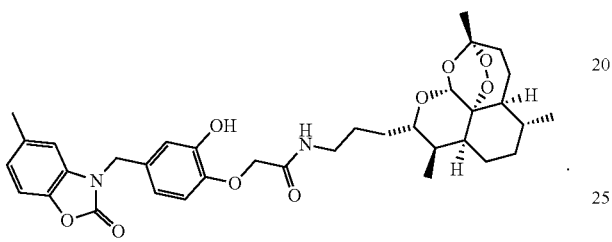

15. A therapeutic compound comprising a compound from formula (1)

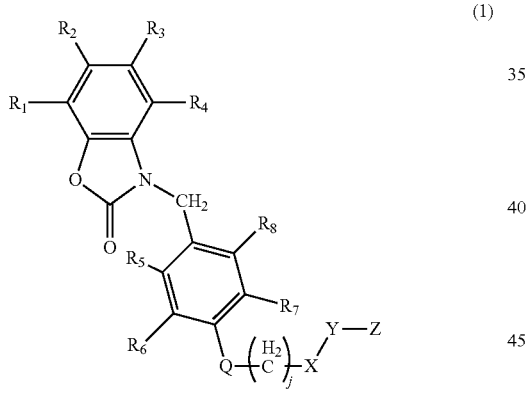

(1)

wherein Q is selected from the group consisting of O, S, N(R9), and C(R9)R10;

X is selected from the group consisting of nothing, O, S, N(R9), N(R9)N(R10), $(CH_2)k$-$(OCH2CH_2)l$, CR9R10-CR11R12, and C(O);

Y is selected from the group consisting of nothing, O, S, N(R11), N(R11)N(R12), —N═, C(O), C(O)O—, C(O)N(R9)-, C(O)N(R9)N(R10)-, C(O)N(R9)N═, C(O)$(CH_2)m$-S—, and C(O)$(CH_2)m$-S—S—;

R1, R2, R3, R4, R5, R6, R7 and R8 are each independently selected from the group consisting of H, hydroxyl, C1-C8 alkyl, alkenyl, alkynyl, substituted C1-C8 alkyl, alkenyl, alkynyl, C1-C8 acyl, substituted C1-C8 acyl, C1-C8 alkoxy, substituted C1-C8 alkoxy, C1-C8 ester, substituted C1-C8 ester, $(CH_2)n$-phenyl, substituted $(CH_2)n$-phenyl, $(CH_2)n$-heterocycle, substituted $(CH_2)n$-heterocycle, halogen, cyano, nitro, amino, $(CH_2)n$-monoalkylamine, substituted $(CH_2)n$-monoalkylamine, $(CH_2)n$-dialkylamine, substituted $(CH_2)n$-dialkylamine, carboxylic acid, $(CH_2)n$-dialkylamine, $(CH_2)n$-monoalkylamide, substituted $(CH_2)n$-monoalkylamide, $(CH_2)n$-dialkylamide, and substituted $(CH_2)n$-dialkylamide; wherein the substitutions are selected from the group consisting of C1-C8 alkyl, C1-C8 alkenyl, halo-substituted aryl, aryl, hydroxyl, hydrogen, C1-C8 alkoxy, and combinations thereof R9, R10, R11, and R12 are each independently selected from the group consisting of H, hydroxyl, C1-C8 alkyl, substituted C1-C8 alkyl, alkenyl, alkynyl, $(CH_2)$-phenyl, substituted $(CH_2)n$-phenyl, $(CH_2)n$-heterocycle, and substituted $(CH_2)_n$-heterocycle; wherein the substitutions are selected from the group consisting of C1-C8 alkyl, C1-C8 alkenyl, halo-substituted aryl, aryl, hydroxyl, hydrogen, C1-C8 alkoxy, and combinations thereof j, m, and n are each integers independently from 0 to 8, k is an integer from 0 to 2, l is an integer from 1 to 8; and Z represents a drug or an imaging moiety.

\* \* \* \* \*